US005705519A

United States Patent [19]
Audia et al.

[11] Patent Number: 5,705,519
[45] Date of Patent: Jan. 6, 1998

[54] METHOD FOR TREATING 5-$HT_{2B}$ RECEPTOR RELATED CONDITIONS

[75] Inventors: James E. Audia, Indianapolis; Marlene Cohen, Carmel; Jaswant S. Gidda, Carmel; David L. Nelson, Carmel, all of Ind.

[73] Assignee: Eli Lilly and Company, Indianapolis, Ind.

[21] Appl. No.: 440,013

[22] Filed: May 12, 1995

Related U.S. Application Data

[60] Division of Ser. No. 380,566, Feb. 6, 1995, which is a continuation-in-part of Ser. No. 212,622, Mar. 11, 1994, abandoned.

[51] Int. Cl.$^6$ .................................................. A01N 43/38
[52] U.S. Cl. ............................................................ 514/415
[58] Field of Search ............................ 514/415; 548/469, 548/509

[56] References Cited

U.S. PATENT DOCUMENTS

| | | |
|---|---|---|
| 4,520,024 | 5/1985 | Cohen et al. |
| 4,563,461 | 1/1986 | Cohen et al. |
| 4,902,691 | 2/1990 | Cohen et al. |
| 4,931,447 | 6/1990 | Foreman et al. |
| 4,981,859 | 1/1991 | Foreman et al. |
| 5,141,944 | 8/1992 | Cohen et al. |

OTHER PUBLICATIONS

D. Hoyer et al., Pharmacological Reviews 1994, vol. 46, pp. 157–179 and 191–203, Feb. 1994.
Forbes, Ian T., et al., *J. Med. Chem.*, 36:1104–1107 (1993).
Leonard, B.E., *International Clinical Psychopharmacology*, 7:13–21 (1992).
Fludzinski, P., *Journal of Medicinal Chemistry*, 29:2415–2418 (1986).
Kalkman, H.O., *Life Sciences*, 54:641–644 (1994).
Wainscott David B., *Molecular Pharmacology*, 43:419–426 (1993).
Foguet M., et al., *NeuroReport*, 3:345–348 (1992).
Cohen, Marlene L., et al., *The Journal of Pharmacology and Experimental Therapeutics*, 233:75–79, 770–774 (1985).
Clineschmidt, Bradley V., et al., *The Journal of Pharmacology and Experimental Therapeutics*, 235:696–708 (1985).
Cohen, Marlene L., et al., *Life Sciences*, 38:1–5 (1986).
Talley, N. J., Alimentary Pharmacology and Therapeutics, Jun. 1992, vol. 6, p. 273.
Saxena, P. R., et al., Archives Internationales de Pharmacodynamie et de Therapie, Feb. 1985, vol. 277, p. 2.
Woelfel, R. et al., Naunyn–Schmiedeberg's Archives of Pharmacology, Jan. 1992, vol. 345 p. 129.
Snape, M. F., et al., Pharmacology and Toxicology, Jan. 1994, vol. 74, p. 40.
Born, G. V. R., et al., British Journal of Pharmacology, Jan. 1972, vol. 44, p. 117.
Bjorklund, A., et al., Acta Physiologica Scandinavica Supplementum 429, 1975, p. 29, Jun. 1976.
Lessin, A. W., et al., British Journal of Pharmacology and Chemotherapy, Jan. 1967, vol. 29, p. 70.
Kumbar, M., et al., journal of Pharmaceutical Sciences, Jul. 1976, vol. 65, p. 1014.

*Primary Examiner*—Charles T. Jordan
*Assistant Examiner*—John R. Hardee
*Attorney, Agent, or Firm*—MaCharri Vorndran-Jones; David E. Boone

[57] ABSTRACT

The present invention provides methods for binding a 5-$HT_{2B}$ receptor in mammals using a both known and novel compounds. Further, the invention provides a method for treating or preventing 5-$HT_{2B}$ related conditions. Finally, the invention provides an article of manufacture.

13 Claims, No Drawings

METHOD FOR TREATING 5-HT$_{2B}$ RECEPTOR RELATED CONDITIONS

CROSS REFERENCE

This application is a division of application Ser. No. 08/380,566, filed Feb. 6, 1995, now abandoned, which is a continuation-in-part of application Ser. No. 08/212,622, filed Mar. 11, 1994, which is now abandoned.

FIELD OF THE INVENTION

The present invention relates to a method for treating 5HT$_{2B}$ receptor related conditions. Further, this application discloses new compounds of Formulas XI and XII infra.

BACKGROUND OF THE INVENTION

This invention is directed to a method for treating a mammal suffering from or susceptible to a condition associated with modulation of a 5-HT$_{2B}$ receptor.

Blocking serotonin receptors has been shown to result in a number of beneficial pharmacological effects, including reduction in disease states such as hypertension, depression, anxiety, and the like; see U.S. Pat. No. 5,141,944. Nelson et al., *Psychopharmacology and Biochemistry of Neurotransmitter Receptors*, eds. H. I. Yamamura et al., Elsevier/North Holland Inc., p 325, have confirmed that there are multiple serotonin recognition sites. The general class of serotonin receptors are referred to as the 5-HT receptors. Specific 5-HT receptor sites include 5-HT$_{1A}$, 5-HT$_{1B}$, 5-HT$_{1D}$, 5-HT$_{2A}$, 5-HT$_{2B}$, 5-HT$_{2C}$, 5-HT$_3$, and 5-HT$_4$ sites. Each of these receptors mediates certain physiological effects. See Leonard, B. E., *International Clinical Psychopharmacology*, 7:13–21 (1992).

This invention provides a method for using compounds which are active at the 5-HT$_{2B}$ receptor to treat or prevent 5-HT$_{2B}$ related conditions. Further, this invention provides a method for selectively blocking the 5-HT$_{2B}$ receptor. Additionally, this invention provides a method for blocking human 5-HT$_{2B}$ receptors. The 5-HT$_{2B}$ receptor active compounds provide a useful tool for characterizing the 5-HT$_{2B}$ receptor.

This invention provides a group of compounds which are 5HT$_{2B}$ receptor antagonists. Applicants have discovered that such compounds are potent competitive inhibitors of serotonin-induced contraction of the colon. Thus, this invention provides compounds which can act to normalize gastrointestinal motility and be useful in the treatment of Functional Bowel Disorders.

Further, it has been discovered the 5-HT$_{2B}$ receptor is localized in the rat lung, stomach fundus, uterus, bladder, and colon. Interesting areas of 5-HT$_{2B}$ receptor localization in the human include but are not limited to the brain and blood vessels. Thus, conditions which can be treated using a compound which modulates a 5-HT$_{2B}$ receptor includes, for example, psychosis, depression, anxiety disorders, uterine diseases such as endometriosis, fibrosis, and other abnormal uterine contractivity, panic attack, migraine, eating disorders, seasonal affective disorder, consumption disorders, cardiovascular conditions, such as thrombosis, hypertension, angina, vasospasm, and other vascular occlusive diseases, incontinence, bladder dysfunction, respiratory/airway disorders including asthma, and the like.

SUMMARY OF THE INVENTION

This invention provides a method for treating a mammal suffering from or susceptible to a condition associated with dysfunctional or abnormal 5-HT$_{2B}$ receptor stimulation, comprising administering an effective amount of a compound interacting with the 5HT$_{2B}$ receptor as an agonist, partial agonist or antagonist selected from the group consisting of a compound of the Formula I

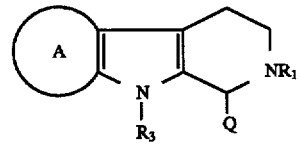

wherein:

Q is hydrogen or (CHR$_2$)R$_4$

R$_1$ is hydrogen or C$_1$–C$_3$ alkyl;

R$_2$ is hydrogen or C$_1$–C$_3$ alkyl;

R$_3$ is hydrogen or C$_1$–C$_3$ alkyl;

R$_4$ is C$_5$–C$_8$ cycloalkyl, substituted C$_5$–C$_8$ cycloalkyl, C$_5$–C$_8$ cycloalkenyl, substituted C$_5$–C$_8$ cycloalkenyl, bicyclic or substituted bicyclic;

A is selected from the group consisting of

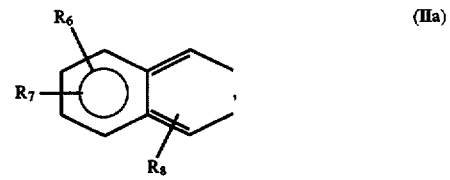

(IIa)

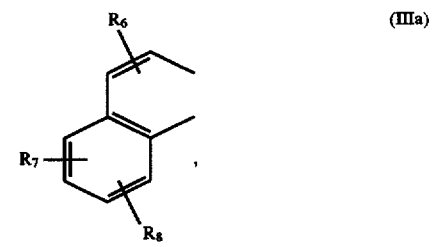

(IIIa)

and

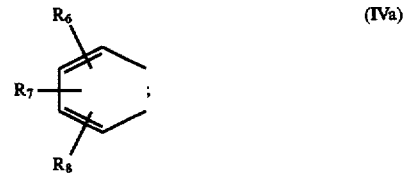

(IVa)

wherein

R$_6$ and R$_7$ are, independently, hydrogen, C$_1$–C$_6$ alkyl, C$_2$–C$_6$ alkenyl, halo, halo(C$_1$–C$_6$)alkyl, halo(C$_2$–C$_6$)alkenyl, COR$_5$, C$_1$–C$_{10}$ alkanoyl, CO$_2$R$_5$·, (C$_1$–C$_6$ alkyl)$_m$amino, NO$_2$, —SR$_5$, or OR$_5$;

m is 1 or 2;

R$_5$ is independently hydrogen or C$_1$–C$_4$ alkyl;

R$_{5'}$ is C$_1$–C$_4$ alkyl;

R$_8$ is independently selected from the group consisting of an R$_6$ group, substituted C$_3$–C$_8$ cycloalkyl, C$_3$–C$_8$ cycloalkyl, C$_3$–C$_8$ cycloalkyl-(C$_1$–C$_3$)alkyl, C$_5$–C$_8$ cycloalkenyl, substituted C$_5$–C$_8$ cycloalkenyl, C$_5$–C$_8$ cycloalkenyl-(C$_1$–C$_3$)alkyl, C$_7$–C$_{20}$ arylalkyl; or R$_6$ and R$_7$ together with the carbon atoms of group A form a 5- to 8-member carbon ring;, a compound of Formula II

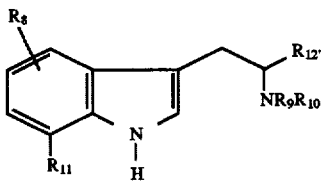

wherein $R_8$ is selected from the group consisting of hydrogen, $C_1$–$C_6$ alkyl, $C_2$–$C_6$ alkenyl, halo, halo($C_2$–$C_6$)alkyl, halo($C_1$–$C_6$)alkenyl, $COR_5$, $C_1$–$C_{10}$ alkanoyl, $CO_2R_5$, ($C_1$–$C_6$ alkyl)$_m$amino, $NO_2$, —$SR_5$, $OR_5$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, and $C_7$–$C_{20}$ arylalkyl;

$R_5$ is independently hydrogen or $C_1$–$C_4$ alkyl;

$R_{5'}$ is $C_1$–$C_4$ alkyl;

$R_9$ and $R_{10}$ are independently selected from the group consisting of hydrogen, $C_1$–$C_6$ alkyl, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, $C_7$–$C_{20}$ arylalkyl;

$R_{11}$ is selected from the group consisting of $C_1$–$C_4$ alkyl, $OR_{5'}$, fluoro, bromo, iodo, and chloro;

$R_{12'}$ is selected from the group consisting of hydrogen and $C_1$–$C_4$ alkyl;

a compound of Formula III

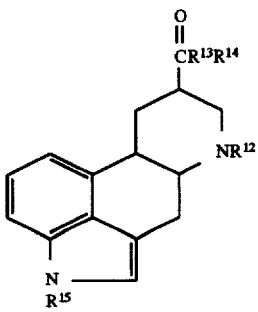

wherein:

$R^{12}$ is $C_1$–$C_4$ alkyl or allyl;

$R^{13}$ is —O— or —N($R^{15}$)—;

$R^{15}$ is hydrogen or $C_1$–$C_4$ alkyl;

$R^{14}$ is $C_1$–$C_4$ alkyl, hydroxy $C_1$–$C_4$ alkyl, $C_3$–$C_7$ cycloalkyl, and $C_3$–$C_7$ cycloalkyl substituted with hydroxy or methoxy;

a compound of Formula IV

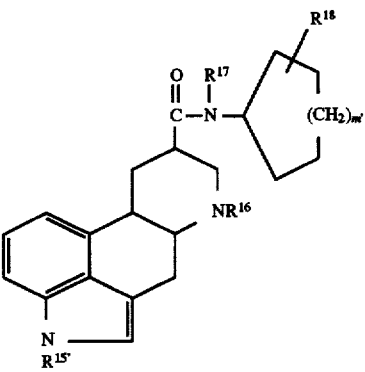

wherein:

$R^{15'}$ is $C_1$–$C_4$ alkyl;

$R^{16}$ is allyl or $C_1$–$C_4$ straight chain alkyl;

$R^{17}$ is hydrogen or $C_1$–$C_4$ straight chain alkyl;

$R^{18}$ is hydrogen, $C_1$–$C_4$ alkyl, hydroxy, or $C_1$–$C_4$ alkyloxy;

m' is 0, 1, 2, or 3;

a compound of Formula V

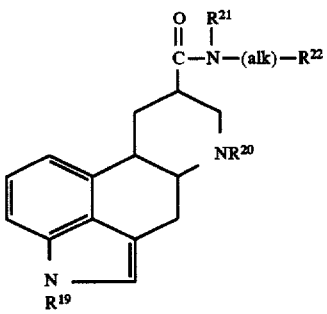

wherein:

$R^{19}$ is $C_1$–$C_4$ alkyl;

$R^{20}$ is allyl or $C_1$–$C_4$ straight chain alkyl;

$R^{21}$ is hydrogen or $C_1$–$C_4$ straight chain alkyl;

$R^{22}$ is pyridinyl or imidazolyl;

alk is a divalent organic radical derived from a straight or branched $C_1$–$C_5$ alkane;

a compound of Formula VI

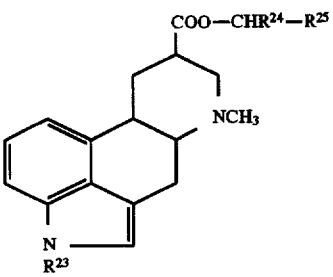

wherein:

$R^{23}$ is $C_1$–$C_3$ alkyl or allyl;

$R^{24}$ is $C_1$–$C_3$ hydroxyalkyl or $C_1$–$C_3$ dihydroxyalkyl;

$R^{25}$ is hydrogen or $CH_3$;

a compound of Formula VII

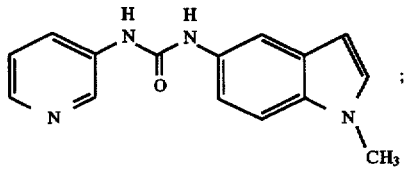

a compound of Formula VIII

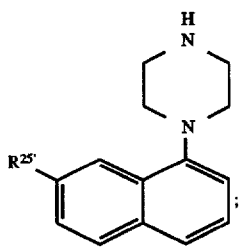

$R^{25'}$ is hydrogen or methoxy;

a compound of Formula IX

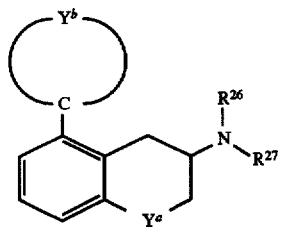

wherein:

$Y^b$, in combination with the carbon atom to which it is joined, defines a substituted or unsubtituted aromatic heterocyclic 5-membered ring selected from the group consisting of

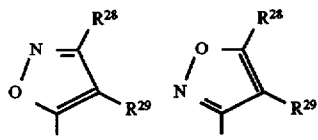

$R^{26}$ is hydrogen, $C_1$–$C_3$ alkyl, allyl, or

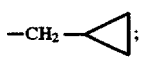

$R^{27}$ is hydrogen, $C_1$–$C_3$ alkyl, allyl,

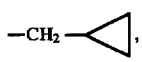

or $(CH_2)_{n'}$—X";

n' is 1 to 5;

X" is an optionally substituted phenyl, $C_1$–$C_3$ alkoxy, or $C_1$–$C_3$ alkylthio;

$R^{28}$ and $R^{29}$ are independently hydrogen, $C_1$–$C_3$ alkyl, $C_1$–$C_3$ alkoxy, hydroxy, $C_1$–$C_3$ alkylthio, halo, CN, phenyl; or together are —$(CH_2)_{p''}$—;

p" is 3 to 6;

$Y^a$ is —$CH_2$—, —O—, —$S(O)_{m''}$—;

m" is 0, 1, or 2; and a compound of the Formula X

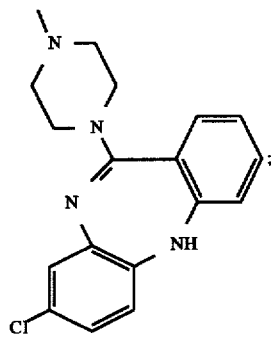

or a pharmaceutically acceptable salt or solvate thereof.

This invention provides a method for treating a mammal suffering from or susceptible to a condition associated with dysfunctional or abnormal 5-$HT_{2B}$ receptor stimulation, comprising administering an effective amount of a compound interacting with the 5$HT_{2B}$ receptor as an agonist, partial agonist or antagonist selected from the group consisting of a compound of the Formula XI

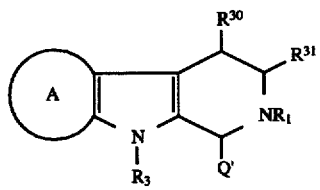

wherein

Q' is selected from the group consisting of hydrogen, $R_{34}$, and $(CHR_2)R_4$;

$R_{34}$ is selected from the group consisting of spiro-bicyclic, substituted spiro-bicyclic, bicyclic or substituted bicyclic;

$R_1$ is hydrogen or $C_1$–$C_3$ alkyl;

$R_2$ is hydrogen or $C_1$–$C_6$ alkyl;

$R_3$ is hydrogen or $C_1$–$C_3$ alkyl;

$R_4$ is $C_5$–$C_8$ cycloalkyl, substituted $C_5$–$C_8$ cycloalkyl, $C_5$–$C_8$ cycloalkenyl, substituted $C_5$–$C_8$ cycloalkenyl, bicyclic or substituted bicyclic;

A is selected from the group consisting of

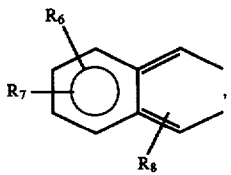

(IIa)

-continued

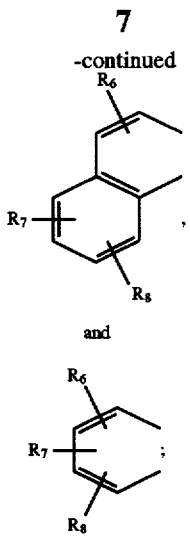

(IIIa)

and (IVa)

wherein

R$_6$ and R$_7$ are, independently, hydrogen, C$_1$–C$_6$ alkyl, C$_2$–C$_6$ alkenyl, halo, halo(C$_1$–C$_6$)alkyl, halo(C$_2$–C$_6$) alkenyl, COR$_5$, C$_1$–C$_{10}$ alkanoyl, CO$_2$R$_5'$, (C$_1$–C$_6$ alkyl)$_m$amino, NO$_2$, —SR$_5$, or OR$_5$;

m is 1 or 2;

R$_5$ is independently hydrogen or C$_1$–C$_4$ alkyl;

R$_{5'}$ is C$_1$–C$_4$ alkyl;

R$_8$ is independently selected from the group consisting of an R$_6$ group, substituted C$_3$–C$_8$ cycloalkyl, C$_3$–C$_8$ cycloalkyl, C$_3$–C$_8$ cycloalkyl-(C$_1$–C$_3$)alkyl, C$_5$–C$_8$ cycloalkenyl, substituted C$_5$–C$_8$ cycloalkenyl, C$_5$–C$_8$ cycloalkenyl-(C$_1$–C$_3$)alkyl, C$_7$–C$_{20}$ arylalkyl; or R$_6$ and R$_7$ together with the carbon atoms of group A form a 5- to 8-member carbon ring;

R$^{30}$ and R$^{31}$ join to form a 3 to 8 member carbon ring; or

R$^{30}$ and R$^{31}$ are independently selected from the group consisting of C$_1$–C$_6$ alkyl and C$_2$–C$_6$ alkenyl; or a pharmaceutically acceptable salt or solvate thereof.

This invention provides a method for treating a mammal suffering from or susceptible to a condition associated with dysfunctional or abnormal 5-HT$_{2B}$ receptor stimulation, comprising administering an effective amount of a compound interacting with the 5HT$_{2B}$ receptor as an agonist, partial agonist or antagonist selected from the group consisting of a compound of the Formula XII

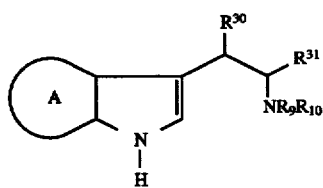

XII

A is selected from the group consisting of

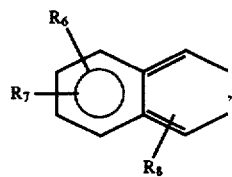

(IIa)

-continued

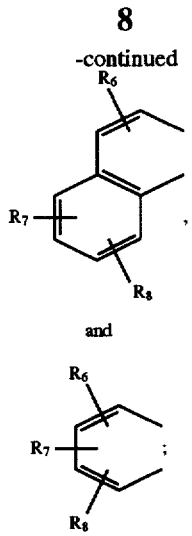

(IIIa)

and (IVa)

wherein

R$_6$ and R$_7$ are, independently, hydrogen, C$_1$–C$_6$ alkyl, C$_2$–C$_6$ alkenyl, halo, halo(C$_1$–C$_6$)alkyl, halo(C$_2$–C$_6$) alkenyl, COR$_5$, C$_1$–C$_{10}$ alkanoyl, CO$_2$R$_5'$, (C$_1$–C$_6$ alkyl)$_m$amino, NO$_2$, —SR$_5$, or OR$_5$;

m is 1 or 2;

R$_8$ is selected from the group consisting of hydrogen, C$_1$–C$_6$ alkyl, C$_2$–C$_6$ alkenyl, halo, halo(C$_2$–C$_6$)alkyl, halo(C$_1$–C$_6$)alkenyl, COR$_5$, C$_1$–C$_{10}$ alkanoyl, CO$_2$R$_5'$, (C$_1$–C$_6$ alkyl)$_m$amino, NO$_2$, —SR$_5$, OR$_5$, substituted C$_3$–C$_8$ cycloalkyl, C$_3$–C$_8$ cycloalkyl, C$_3$–C$_8$ cycloalkyl-(C$_1$–C$_3$)alkyl, C$_5$–C$_8$ cycloalkenyl, substituted C$_5$–C$_8$ cycloalkenyl, C$_5$–C$_8$ cycloalkenyl-(C$_1$–C$_3$)alkyl, and C$_7$–C$_{20}$ arylalkyl;

R$_5$ is independently hydrogen or C$_1$–C$_4$ alkyl;

R$_{5'}$ is C$_1$–C$_4$ alkyl;

R$_6$ and R$_7$ together with the carbon atoms of group A form a 5- to 8-member carbon ring;

R$_9$ and R$_{10}$ are independently selected from the group consisting of hydrogen, C$_1$–C$_6$ alkyl, substituted C$_3$–C$_8$ cycloalkyl, C$_3$–C$_8$ cycloalkyl, C$_3$–C$_8$ cycloalkyl-(C$_1$–C$_3$)alkyl, C$_5$–C$_8$ cycloalkenyl-(C$_1$–C$_3$)alkyl, C$_7$–C$_{20}$ arylalkyl;

R$_{11}$ is selected from the group consisting of C$_1$–C$_4$ alkyl, OR$_5'$, fluoro, bromo, iodo, and chloro;

R$^{30}$ and R$^{31}$ join to form a 3 to 8 member carbon ring; or

R$^{30}$ and R$^{31}$ are independently selected from the group consisting of C$_1$–C$_6$ alkyl and C$_2$–C$_6$ alkenyl; or a pharmaceutically acceptable salt or solvate thereof.

Second, this invention provides a method for blocking a 5HT$_{2B}$ receptor in a mammal, comprising administering a 5HT$_{2B}$ receptor occupying dose of a compound selected from the group consisting of Formula I, II, III, IV, V, VI, VII, VIII, IX, and X supra.; or a pharmaceutically acceptable salt or solvate thereof.

This invention provides a method for blocking a 5HT$_{2B}$ receptor in a mammal, comprising administering a 5HT$_{2B}$ receptor occupying dose of a compound selected from the group consisting of Formula XI, and XII supra.; or a pharmaceutically acceptable salt or solvate thereof.

Third, this invention provides a method for selectively interacting with the 5-HT$_{2B}$ receptor in a mammal, comprising administering a 5-HT$_{2B}$ selective compound selected from the group consisting of Formula I, II, III, IV, V, VI, VII, VIII, IX, and X supra.; or a pharmaceutically acceptable salt or solvate thereof to a mammal.

This invention provides a method for selectively interacting with the 5-HT$_{2B}$ receptor in a mammal, comprising administering a 5-HT$_{2B}$ selective compound selected from the group consisting of of Formula XI and XII; or a pharmaceutically acceptable salt or solvate thereof to a mammal.

The present invention provides compounds of the Formula XI

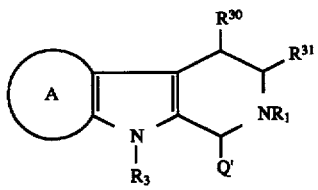

XI wherein

Q' is selected from the group consisting of hydrogen, $R_{34}$, and $(CHR_2)R_4$;

$R_{34}$ is selected from the group consisting of spiro-bicyclic, substituted spiro-bicyclic, bicyclic or substituted bicyclic;

$R_1$ is hydrogen or $C_1$–$C_3$ alkyl;

$R_2$ is hydrogen or $C_1$–$C_6$ alkyl;

$R_3$ is hydrogen or $C_1$–$C_3$ alkyl;

$R_4$ is $C_5$–$C_8$ cycloalkyl, substituted $C_5$–$C_8$ cycloalkyl, $C_5$–$C_8$ cycloalkenyl, substituted $C_5$–$C_8$ cycloalkenyl, bicyclic or substituted bicyclic;

A is selected from the group consisting of

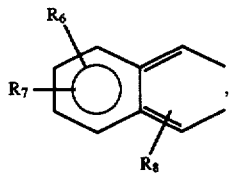

(IIa)

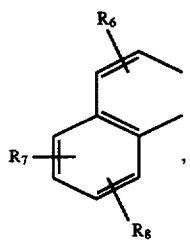

(IIIa)

and

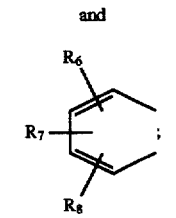

(IVa)

wherein $R_6$ and $R_7$ are, independently, hydrogen, $C_1$–$C_6$ alkyl, $C_2$–$C_6$ alkenyl, halo, halo($C_1$–$C_6$)alkyl, halo($C_2$–$C_6$) alkenyl, $COR_5$, $C_1$–$C_{10}$ alkanoyl, $CO_2R_{5'}$, ($C_1$–$C_6$ alkyl)$_m$amino, $NO_2$, —$SR_5$, or $OR_5$;

m is 1 or 2;

$R_5$ is independently hydrogen or $C_1$–$C_4$ alkyl;

$R_{5'}$ is $C_1$–$C_4$ alkyl;

$R_8$ is independently selected from the group consisting of an $R_6$ group, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$) alkyl, $C_7$–$C_{20}$ arylalkyl; or $R_6$ and $R_7$ together with the carbon atoms of group A form a 5- to 8-member carbon ring;

$R^{30}$ and $R^{31}$ join to form a 3 to 8 member carbon ring; or $R^{30}$ and $R^{31}$ are independently selected from the group consisting of $C_1$–$C_6$ alkyl and $C_2$–$C_6$ alkenyl; or a pharmaceutically acceptable salt or solvate thereof.

This invention provides compounds of Formula

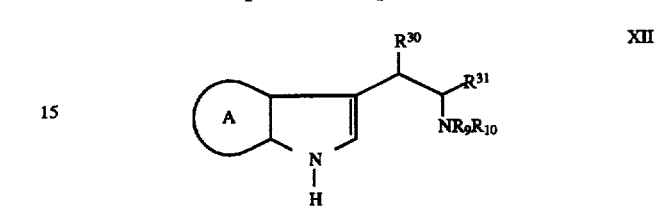

XII

A is selected from the group consisting of

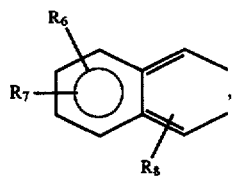

(IIa)

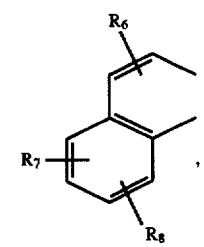

(IIIa)

and

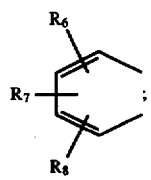

(IVa)

wherein $R_6$ and $R_7$ are, independently, hydrogen, $C_1$–$C_6$ alkyl, $C_2$–$C_6$ alkenyl, halo, halo($C_1$–$C_6$)alkyl, halo($C_2$–$C_6$) alkenyl, $COR_5$, $C_1$–$C_{10}$ alkanoyl, $CO_2R_{5'}$, ($C_1$–$C_6$ alkyl)$_m$amino, $NO_2$, —$SR_5$, or $OR_5$;

m is 1 or 2;

$R_8$ is selected from the group consisting of hydrogen, $C_1$–$C_6$ alkyl, $C_2$–$C_6$ alkenyl, halo, halo($C_2$–$C_6$)alkyl, halo($C_1$–$C_6$)alkenyl, $COR_5$, $C_1$–$C_{10}$ alkanoyl, $CO_2R_{5'}$, ($C_1$–$C_6$ alkyl)$_m$amino, $NO_2$, —$SR_5$, $OR_5$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, and $C_7$–$C_{20}$ arylalkyl;

$R_5$ is independently hydrogen or $C_1$–$C_4$ alkyl;

$R_{5'}$ is $C_1$–$C_4$ alkyl;

$R_6$ and $R_7$ together with the carbon atoms of group A form a 5- to 8-member carbon ring;

$R_9$ and $R_{10}$ are independently selected from the group consisting of hydrogen, $C_1$–$C_6$ alkyl, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, $C_7$–$C_{20}$ arylalkyl;

$R_{11}$ is selected from the group consisting of $C_1$–$C_4$ alkyl, $OR_5$, fluoro, bromo, iodo, and chloro;

$R^{30}$ and $R^{31}$ join to form a 3 to 8 member carbon ring; or $R^{30}$ and $R^{31}$ are independently selected from the group consisting of $C_1$–$C_6$ alkyl and $C_2$–$C_6$ alkenyl; or a pharmaceutically acceptable salt or solvate thereof.

Finally this invention provides a method for interacting with a human 5-$HT_{2B}$ receptor in a human, comprising administering a 5-$HT_{2B}$ blocking dose of a compound selected from the group consisting of Formula I, II, III, IV, V, VI, VII, VIII, IX, and X supra.; or a pharmaceutically acceptable salt or solvate thereof to a human.

This invention provides a method for interacting with a human 5-$HT_{2B}$ receptor in a human, comprising administering a 5-$HT_{2B}$ blocking dose of a compound selected from the group consisting of Formula XI and XII; or a pharmaceutically acceptable salt or solvate thereof.

A further embodiment of this invention is an article of manufacture comprising packaging material and one or more pharmaceutical agents contained within said packaging material, wherein said pharmaceutical agent is effective for the treatment of a condition requiring 5-$HT_{2B}$ receptor occupation and is selected from the group consisting of a compound of Formula I, II, III, IV, V, VI, VII, VIII, IX, and X supra.; or a pharmaceutically acceptable salt or solvate thereof; and said packaging material comprises a label which indicates that said pharmaceutical agent can be used for the treatment of a condition requiring 5-$HT_{2B}$ receptor modulation.

Another embodiment of this invention is an article of manufacture comprising packaging material and one or more pharmaceutical agents contained within said packaging material, wherein said pharmaceutical agent is effective for the treatment of a condition requiring 5-$HT_{2B}$ receptor occupation and is selected from the group consisting of a compound of Formula XI, and XII supra.; or a pharmaceutically acceptable salt or solvate thereof; and said packaging material comprises a label which indicates that said pharmaceutical agent can be used for the treatment of a condition requiring 5-$HT_{2B}$ receptor modulation.

DETAILED DESCRIPTION OF THE INVENTION

The term "treating" as used herein includes prophylaxis of the named physical and/or mental condition or amelioration or elimination of the developed physical and/or mental condition once it has been established.

The terms "$C_1$–$C_n$ alkyl" wherein n=2–10, as used herein, represent a branched or linear alkyl group having from one to the specified number of carbon atoms. Typical $C_1$–$C_6$ alkyl groups include methyl, ethyl, n-propyl, iso-propyl, butyl, iso-butyl, sec-butyl, tert-butyl, pentyl, hexyl and the like.

As used herein, the term "$R^{30}$ and $R^{31}$ join to form a 3 to 8 member carbon ring" shall mean that $R^{30}$ and $R^{31}$ are most preferably independently selected from the group consisting of $C_1$–$C_6$ alkyl and $C_2$–$C_6$ alkenyl. The carbon ring thus formed may be saturated or unsaturated. As used herein, such ring may be illustrated as:

wherein $n^{30}$ shall refer to the total number of carbon atoms in the ring thus formed. Such carbon ring may be substituted with from one to four substituents independently selected from the group consisting of hydrogen, $C_1$–$C_6$ alkyl, $NO_2$, halo, halo($C_1$–$C_6$)alkyl, halo($C_2$–$C_6$)alkenyl, $C_2$–$C_6$ alkenyl, $CO_2R_5$, ($C_1$–$C_6$ alkyl)$_m$amino, —$SR_5$, and $OR_5$. A preferred embodiment is when $R^{30}$ and $R^{31}$ join to form a $C_3$–$C_6$ member saturated carbon ring. It is another preferred embodiment that $R^{30}$ and $R^{31}$ join to form a $C_3$–$C_5$ member saturated carbon ring.

When $R^{30}$ and $R^{31}$ do not join to form a carbon ring, it is a preferred embodiment that $R^{30}$ and $R^{31}$ are independently selected from the group consisting of $C_1$–$C_3$ alkyl.

The terms "$C_2$–$C_n$ alkenyl" wherein n=3–10, as used herein, represents an olefinically unsaturated branched or linear group having from 2 to 10 carbon atoms and at least one double bond. The groups can be branched or straight chain. Examples of such groups include 1-propenyl, 2-propenyl (—$CH_2$—CH=$CH_2$), 1,3-butadienyl (—CH=CHCH=$CH_2$), 1-butenyl (—CH=CHCH$_2$CH$_3$), hexenyl, pentenyl, and the like.

The terms "halide", "halogen", and "halo" include fluorine, chlorine, bromine, and iodine. The preferred halogen is chlorine.

The terms "halo($C_1$–$C_6$)alkyl" and "halo($C_2$–$C_6$)alkenyl" refer to alkyl or alkenyl substituents having one or more independently selected halo atoms attached at one or more available carbon atoms. These terms include chloromethyl, bromoethyl, trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, chloroethylenyl, 5-fluoro-3-pentenyl, 3-chloro-2-bromo-5-hexenyl, 3-chloro-2-bromo-butyl, trichloromethyl, dichloroethyl, 1,4-dichlorobutyl, 3-bromopentyl, 1,3-dichlorobutyl, 1,1-dichloropropyl, and the like. More preferred halo-($C_1$–$C_6$) alkyl groups are trichloromethyl, trichloroethyl, and trifluoromethyl. The most preferred halo-($C_1$–$C_6$)alkyl is trifluoromethyl.

The term "$C_1$–$C_{10}$ alkanoyl" represents a group of the formula C(O)($C_1$–$C_9$) alkyl. Typical $C_1$–$C_{10}$ alkanoyl groups include acetyl, propanoyl, butanoyl, and the like.

The term "($C_1$–$C_6$ alkyl)$_m$amino" wherein m=1–2; refers to either a mono- or a dialkylamino group in which the alkyl portion of the group may be straight or branched. Examples of such groups are methylamino, dimethylamino, ethylamino, diethylamino, 2-propylamino, 1-propylamino, di(n-propyl)amino, di(iso-propyl)amino, methyl-n-propylamino, t-butylamino, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "substituted($C_5$–$C_n$) cycloalkyl" refers to a cycloalkyl group as described supra wherein the cycloalkyl group may be substituted with from one to four substituents independently selected from the group consisting of hydrogen, $C_1$–$C_6$ alkyl, $NO_2$, halo, halo($C_1$–$C_6$)alkyl, halo ($C_2$–$C_6$)alkenyl, $C_2$–$C_6$ alkenyl, $CO_2R_5$, ($C_1$–$C_6$ alkyl)$_m$ amino, —$SR_5$, and $OR_5$.

The term "$C_3$–$C_8$ cycloalkyl-($C_1$–$C_3$)alkyl" represents a linear alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl" represents an olefinically unsaturated ring having five to eight carbon atoms, e.g., phenyl, cyclohexadienyl, cyclohexenyl, cyclopentenyl, cycloheptenyl, cyclooctenyl, cyclohexadienyl, cycloheptadienyl, cyclooctatrienyl and the like.

The term "substituted ($C_5$–$C_8$) cycloalkenyl" refers to a cycloalkenyl group as described supra wherein the cycloalkenyl group may be substituted with from one to four substituents independently selected from the group consisting of hydrogen, $C_1$–$C_6$ alkyl, $NO_2$, halo, halo($C_1$–$C_6$)alkyl, halo($C_2$–$C_6$)alkenyl, $C_2$–$C_6$ alkenyl, $COR_5$, $C_1$–$C_{10}$ alkanoyl, $C_7$–$C_{20}$ arylalkyl, $CO_2R_5$, ($C_1$–$C_6$ alkyl)$_m$amino, —$SR_5$, and $OR_5$.

The term "$C_5$–$C_8$ cycloalkenyl-($C_1$–$C_3$)alkyl" represents a linear $C_1$–$C_3$ alkyl group substituted at a terminal carbon with a $C_5$–$C_8$ cycloalkenyl group.

The term "aryl" represents phenyl or naphthyl. The aryl group can be unsubstituted or can have one or two substituents independently selected from the group consisting of $C_1$–$C_6$ alkyl, $C_3$–$C_8$ cycloalkyl, substituted $C_3$–$C_8$ cycloalkyl, $C_2$–$C_6$ alkenyl, $C_3$–$C_8$ cycloalkyl-($C_1$–$C_3$)alkyl, phenyl, $C_5$–$C_8$ cycloalkenyl, substituted $C_5$–$C_8$ cycloalkenyl, $C_5$–$C_8$ cycloalkenyl-($C_1$–$C_3$)alkyl, $COR_5$, $C_1$–$C_{10}$ alkanoyl, $OR_5$, and $C_7$–$C_{16}$ arylalkyl. The substituents may be located at any available position on the aryl ring.

The term "$C_7$–$C_{20}$ arylalkyl" represents an aryl-($C_1$–$C_{10}$) alkyl substituent wherein the alkyl group is linear, such as benzyl, phenethyl, 3-phenylpropyl, or phenyl-t-butyl; or branched.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "unsaturated bicyclic" represents a stable bicyclic ring of 7 to 12 carbon atoms. The unsaturated bicyclic ring may be attached at any carbon atom which affords a stable structure. The unsaturated bicyclic ring may be substituted with from one to four substituents as defined for "substituted bicyclic" infra.

The general term "substituted bicyclic" refers to a bicyclic ring system with up to 4 substituents attached at any desired positions on the bicyclic ring system. The bicyclic substituents may be independently selected from the group consisting of hydrogen, $C_1$–$C_6$ alkyl, $NO_2$, halo, halo($C_1$–$C_6$)alkyl, halo($C_2$–$C_6$)alkenyl, $C_2$–$C_6$ alkenyl, $COR_5$, $C_1$–$C_{10}$ alkanoyl, $C_7$–$C_{20}$ arylalkyl, $CO_2R_5$, ($C_1$–$C_6$ alkyl)$_m$amino, —$SR_5$, and $OR_5$; wherein $R_5$ is defined supra. It is intended that the substituted bicyclic substituent may bond to the $CHR_2$ group through any available carbon atom in the bicyclic ring system. The term includes, but is not limited to compounds such as, 2-methyldicyclohexyl, 3-hydroxydicyclohexyl, benzocyclohexyl, benzocyclohexenyl, 2-methoxybenzocyclohexyl, 6-chlorobenzocyclohexenyl, 8-ethenylbenzocyclohexyl, and the like.

The term "spiro-bicyclic" and "substituted spiro-bicyclic" refer to a bicyclic or substituted bicyclic (as defined supra.) directly attached to the carbon of the parent ring at substituent Q'. For illustration purposes, a spiro-bicyclic is attached as shown:

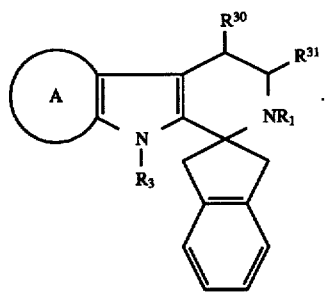

The term "naphthyl" refers to a naphthalene ring system substituent, as commonly used in organic chemistry. The naphthyl substituent may bond to the $CHR_2$ group through any available carbon atom in the naphthyl ring system. The term "substituted naphthyl" refers to a naphthyl ring system with up to 4 substituents attached at any desired positions on the naphthyl ring system. The naphthyl substituents may be independently selected from the "substituted bicyclic" group supra.

The term "phenyl" as used herein refers to an unsubstituted benzene ring system. The term "substituted phenyl" refers to a benzene ring system with from one to three substituents independently selected from the group of bicyclic substituents defined supra; $R_5$ is defined supra.

The term "$C_1$–$C_4$ alkoxy" represents a straight or branched alkoxy chain having from one to four carbon atoms. $C_1$–$C_4$ alkoxy groups include methoxy, ethoxy, n-propoxy, isopropoxy, n-butoxy, and the like.

In a compound of Formula IV when m' is 0, the ring attached to the amide nitrogen atom is cyclopentyl; when m is 1, the ring is cyclohexyl; when m' is 2, the ring is cycloheptyl; and when m' is 3, the ring is cyclooctyl. If the cycloalkyl ring is substituted, the substituent may be at an available position on the ring.

The term "pyridinyl" refers to 2-, 3-, or 4-pyridinyl. The term "imidazolyl" refers to 1-, 2-, or 4-imidazolyl.

The term "alk" refers to a divalent organic radical derived from a straight or branched $C_1$–$C_5$ alkane. Such groups include but are not limited to —$CH_2$—, —$CH(CH_3)$—, —$C(CH_3)_2$—, —$CH(C_2H_5)$—, —$CH_2CH_2$—, —$CH_2CH(CH_3)$—, —$CH_2C(CH_3)_2$—, —$CH_2CH(CH_3)CH_2$—, —$CH(CH_3)CH(CH_3)$—, —$CH(CH_3)CH_2CH(CH_3)$—, and the like.

The term "optionally substituted phenyl" refers to a phenyl ring which may contain one or two substituents selected from the group consisting of $C_1$–$C_3$ alkyl, $C_1$–$C_3$ alkoxy, $C_1$–$C_3$ alkylthio, halo, $NO_2$, and CN.

The term "selective interaction with a 5-$HT_{2B}$ receptor" refers to a method of interacting with the 5-$HT_{2B}$ receptor to a greater extent than the 5-$HT_{2A}$ or 5-$HT_{2C}$ receptor.

The term "protic acid" refers to an acid having an acidic hydrogen. Preferred protic acids include hydrochloric acid, formic acid, perchloric acid, sulfuric acid, and phosphoric acid in an aqueous medium. The most preferred protic acids are hydrochloric acid, sulfuric acid, and formic acid.

The term "organic solvent" includes solvents containing carbon, such as halogenated hydrocarbons, ether, toluene, xylene, benzene, and tetrahydrofuran.

The term "agitate" includes such techniques as stirring, centrifugation, mixing, and other similar methods.

The term "aprotic solvent" refers to polar solvents of moderately high dielectric constant which do not contain an acidic hydrogen. Examples of common aprotic solvents are dimethyl sulfoxide (DMSO), dimethylformamide, sulfolane, tetrahydrofuran, diethylether, methyl-t-butyl ether, or 1,2-dimethoxyethane.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

Abbreviations used herein have their accepted meaning, unless stated otherwise. For example, "Me" and "Et" refer to methyl, ethyl respectively, and "t-Bu" refers to tertiary-butyl. The abbreviation "RT" refers to room temperature or ambient conditions unless indicated otherwise.

The term "ligand" refers to compounds that are bound by the indicated receptor. Compounds useful as selective ligands may be used to selectively occupy the specific receptor site or may act as a selective agonist at the specific receptor site.

The term "substantially pure" is intended to mean at least about 90 mole percent, more preferably at least about 95 mole percent, and most preferably at least about 98 mole percent of the desired enantiomer or stereoisomer is present compared to other possible configurations.

Compounds which are contemplated for use in modulating a $5\text{-HT}_{2B}$ receptor include, but are not limited to 7-bromo-8-methyl-1,2,3,4-tetrahydro-9H-pyrido[3,4b]-indole, 6-isopropyl-8-methoxy-1,2,3,4-tetrahydro-9H-pyrido[3,4b]-indole, 5-chloro-8-ethoxy-1,2,3,4-tetrahydro-9H-pyrido[3,4b]-indole, 6-chloro-7-methyl-8-fluoro-1,2,3,4-tetrahydro-9H-pyrido[3,4b]-indole, 5-dimethylamino-8-hydroxy-1,2,3,4-tetrahydro-9H-pyrido[3,4b]-indole, 6-nitro-8-butyl-1,2,3,4-tetrahydro-9H-pyrido[3,4b]-indole, 7-cyclohexyl-8-hydroxy-1,2,3,4-tetrahydro-9H-pyrido[3,4b]-indole, 6-[3-methyl-cyclohexyl]-8-methyl-1,2,3,4-tetrahydro-9H-pyrido[3,4b]-indole, 6-benzyl-8-fluoro-1,2,3,4-tetrahydro-9H-pyrido[3,4b]-indole, 5-cyclohexylmethyl-8-chloro-1,2,3,4-tetrahydro-9H-pyrido[3,4b]-indole, 6-carboxyl-8-bromo-1,2,3,4-tetrahydro-9H-pyrido[3,4b]-indole, 6-ethoxy-8-isopropyl-3-methyl-1,2,3,4-tetrahydro-9H-pyrido[3,4b]-indole, 6,8-dichloro-4-naphthylmethyl-1,2,3,4-tetrahydro-9H-pyrido[3,4b]-indole, 6,8-dimethyl-3,4-dimethyl-1,2,3,4-tetrahydro-9H-pyrido[3,4b]-indole, 7,8-difluoro-2(N)-methyl-1,2,3,4-tetrahydro-9H-pyrido[3,4b]-indole, 6,8-dibutyl-2(N)-cyclopropylmethyl-1,2,3,4-tetrahydro-9H-pyrido[3,4b]-indole, 6,8-dibromo-2(N)-cyclohexenylmethyl-1,2,3,4-tetrahydro-9H-pyrido[3,4b]-indole, 8-chloro-2(N)-benzyl-1,2,3,4-tetrahydro-9H-pyrido[3,4b]-indole, 8-fluoro-4-methyl-2(N)-cyclohexyl-1,2,3,4-tetrahydro-9H-pyrido[3,4b]-indole, 6-methylamine-8-chloro-1,2,3,4-tetrahydro-9H-pyrido[3,4b]-indole, 6-chloromethyl-8-chloro-1,2,3,4-tetrahydro-9H-pyrido[3,4b]-indole, 7-methoxy-1-naphthylpiperazine, 1-naphthylpiperazine, 7-bromo-1H-indole-3-ethanamine, 7-fluoro-1H-indole-3-ethanamine, 7-methoxy-1H-indole-3-ethanamine, 7-chloro-1H-indole-3-ethanamine, 5-methyl-7-chloro-1H-indole-3-ethanamine, 1-H-Benz(G)indole-3-ethanamine, 6-methyl-7-chloro-1H-indole-3-ethanamine, 6-bromo-7-methyl-1H-indole-3-ethanamine, 6-methyl-1H-indole-3-ethanamine, 5-methyl-7-bromo-1H-indole-3-ethanamine, 6,7-dimethyl-1H-indole-3-ethanamine, 6-methyl-7-bromo-1H-indole-3-ethanamine, (8β)-N-cyclohexyl-1-isopropyl-6-n-butyl-ergoline-8-carboxamide, (8β)-N-cyclohexyl-N-ethyl-1-isopropyl-6-methylergoline-8-carboxamide, other (8β)-1-alkyl-6-(substituted)ergolines described in U.S. Pat. No. 4,931,447, cycloalkylamides of (8β)-alkyl-6-(substituted)ergolines described in U.S. Pat. No. 4,981,859, compounds described in U.S. Pat. No. 4,563,461, compounds described in U.S. Pat. No. 4,902,691, wherein the four aforementioned U.S. Patents are herein incorporated by reference. 1,2-dimethyl-3-ethyl-5-(dimethylamino)-indole, 2-(di-n-propylamino)-8-(isothiazol-3-yl)-1,2,3,4-tetrahydronaphthalene, 2-ethylamino-8-(isoxazol-3-yl)-1,2,3,4-tetrahydronaphthalene, 2-(N-methyl-N-benzylamino)-8-(5-n-propyl-1,2,3-oxadiazol-4-yl)-1,2,3,4-tetrahydronaphthalene, 2-diallylamino-8-(pyrazol-3-yl)-1,2,3,4-tetrahydronaphthalene, 2-diethylamino-8-(1,3,4-oxadiazol-2-yl)-1,2,3,4-tetrahydronaphthalene, 2-(di-n-propylamino)-8-(3-methoxypyrid-2-yl)-1,2,3,4-tetrahydronaphthalene, 2-benzylmethylamino-8-(3-methoxypyrid-2-yl)-1,2,3,4-tetrahydronaphthalene, 2-benzylmethylamino-8-(benzofuran-2-yl)-1,2,3,4-tetrahydronaphthalene, 2-dimethylamino-8-(1,3,5-triazin-2-yl)-1,2,3,4-tetrahydronaphthalene, 2-(dicyclopropylmethylamino)-8-(oxazol-4-yl)-1,2,3,4-tetrahydronaphthalene, 2-ethylamino-8-(1,2,3-oxadiazol-4-yl)-thio-1,2,3,4-tetrahydronaphthalene, 2-n-butylamino-8-(5-methoxypyrimidin-2-yl)-1,2,3,4-tetrahydronaphthalene, 2-(di-n-propylamino)-8-(5-chlorooxazol-2-yl)-1,2,3,4-tetrahydronaphthalene, 2-(di-n-propylamino)-8-(pyrimidin-2-yl)-1,2,3,4-tetrahydronaphthalene, 2-(di-n-propylamino)-8-(2-aminopyrimidin-4-yl)-1,2,3,4-tetrahydronaphthalene, 2-(di-n-propylamino)-8-(3-phenyl-1,2,4-oxadiazol-5-yl)-1,2,3,4-tetrahydronaphthalene, 2-(di-n-propylamino)-8-(3-methyl-1,2,4-oxadiazol-5-yl)-1,2,3,4-tetrahydronaphthalene, 2-(di-n-propylamino)-8-(pyrazin-2-yl)-1,2,3,4-tetrahydronaphthalene, 2-(di-n-propylamino)-6-(bromopyrazin-2-yl)-1,2,3,4-tetrahydronaphthalene, 2-(di-n-propylamino)-8-(benzothiazol-2-yl)-1,2,3,4-tetrahydronaphthalene, 2-(di-n-propylamino)-8-(benzoxazol-2-yl)-1,2,3,4-tetrahydronaphthalene, 2-(di-n-propylamino)-8-(indol-3-yl)-1,2,3,4-tetrahydronaphthalene, 3-(di-n-propylamino)-5-(isoxazol-2-yl)-1,2,3,4-tetrahydronaphthalene, 3-(di-n-propylamino)-5-(isoxazol-2-yl)-chromane, 5-(isoxazol-5-yl)-3-(dipropylamino)chromane, 5-(3-methylisoxazol-5-yl)-3-(dipropylamino)chromane, 5-(4-methylisoxazol-5-yl)-3-(dipropylamino)chromane, 5-(3,4-dimethylisoxazol-5-yl)-3-(dipropylamino)chromane, 5-(3-methylisoxazol-5-yl)-3-(dipropylamino)thiochromane, 5-(4-methylisoxazol-5-yl)-3-(dipropylamino)thiochromane, 5-(3,4-dimethylisoxazol-5-yl)-3-(dipropylamino)thiochromane, 8-(4,5,6,7-tetrahydrobenz[c]isoxazol-1-yl)-2-(dimethylamino) tetrahydronaphthalene, and the like.

Especially preferred compounds for use in modulating a $5\text{-HT}_{2B}$ receptor include 7-bromo-8-methyl-1,2,3,4-tetrahydro-9H-pyrido[3,4b]-indole, 6-isopropyl-8-methoxy-1,2,3,4-tetrahydro-9H-pyrido[3,4b]-indole, 5-chloro-8-ethoxy-1,2,3,4-tetrahydro-9H-pyrido[3,4b]-indole, 6-chloro-7-methyl-8-fluoro-1,2,3,4-tetrahydro-9H-pyrido[3,4b]-indole, 5-dimethylamino-8-hydroxy-1,2,3,4-tetrahydro-9H-pyrido[3,4b]-indole, 6-nitro-8-butyl-1,2,3,4-tetrahydro-9H-pyrido[3,4b]-indole, 7-cyclohexyl-8-hydroxy-1,2,3,4-tetrahydro-9H-pyrido[3,4b]-indole, 6-[3-methyl-cyclohexyl]-8-methyl-1,2,3,4-tetrahydro-9H-pyrido[3,4b]-indole, 6-benzyl-8-fluoro-1,2,3,4-tetrahydro-9H-pyrido[3,4b]-indole, 5-cyclohexylmethyl-8-chloro-1,2,3,4-tetrahydro-9H-pyrido[3,4b]-indole, 6-carboxyl-8-bromo-1,2,3,4-tetrahydro-9H-pyrido[3,4b]-indole, 6-ethoxy-8-isopropyl-1,2,3,4-tetrahydro-9H-pyrido[3,4b]-indole, 6,8-dichloro-4-naphthylmethyl-1,2,3,4-tetrahydro-9H-pyrido[3,4b]-indole, 6,8-dimethyl-3,4-dimethyl-1,2,3,4-tetrahydro-9H-pyrido[3,4b]-indole, 7,8-difluoro-2(N)-methyl-1,2,3,4- tetrahydro-9H-pyrido[3,4b]-indole, 6,8-dibutyl-2(N)-cyclopropylmethyl-1,2,3,4-tetrahydro-9H-pyrido[3,4b]-indole, 6,8-dibromo-2(N)-cyclohexenylmethyl-1,2,3,4-tetrahydro-9H-pyrido[3,4b]-indole, 8-chloro-2(N)-benzyl-1,2,3,4-tetrahydro-9H-pyrido[3,4b]-indole, 8-fluoro-4-methyl-2(N)-cyclohexyl-1,2,3,4-tetrahydro-9H-pyrido[3,4b]-indole, 6-methylamine-8-chloro-3-isopropyl-1,2,3,4-tetrahydro-9H-pyrido[3,4b]-indole, 6-chloromethyl-8-chloro-1,2,3,4-tetrahydro-9H-pyrido[3,4b]-indole, 7-methoxy-1-naphthylpiperazine, 1-naphthylpiperazine, 7-bromo-1H-indole-3-ethanamine, 7-fluoro-1H-indole-3-ethanamine, 7-methoxy-1H-indole-3-ethanamine, 7-chloro-1H-indole-3-ethanamine, 5-methyl-7-chloro-1H-indole-3-ethanamine, 1-H-Benz(G)indole-3-ethanamine, 6-methyl-7-chloro-1H-indole-3-ethanamine, 6-bromo-7-methyl-1H-indole-3-ethanamine, 6-methyl-1H-indole-3-ethanamine, 5-methyl-7-bromo-1H-indole-3-ethanamine, 6,7-dimethyl-1H-indole-3-ethanamine, 6-methyl-7-bromo-1H-indole-3-ethanamine, 1,2-dimethyl-3-ethyl-5-(dimethylamino)-indole, 2-(di-n-propylamino)-8-(isothiazol-3-yl)-1,2,3,4-tetrahydronaphthalene, 2-ethylamino-8-(isoxazol-3-yl)-1,2,3,4-tetrahydronaphthalene, 2-(N-methyl-N-benzylamino)-8-(5-n-propyl-1,2,3-oxadiazol-4-yl)-1,2,3,4-tetrahydronaphthalene, 2-diallylamino-8-(pyrazol-3-yl)-1,2,3,4-tetrahydronaphthalene, 2-diethylamino-8-(1,3,4-oxadiazol-2-yl)-1,2,3,4-tetrahydronaphthalene, 2-(di-n-propylamino)-8-(3-methoxypyrid-2-yl)-1,2,3,4-tetrahydronaphthalene, 2-benzylmethylamino-8-(3-methoxypyrid-2-yl)-1,2,3,4-tetrahydronaphthalene, 2-benzylmethylamino-8-(benzofuran-2-yl)-1,2,3,4-tetrahydronaphthalene, 2-dimethylamino-8-(1,3,5-triazin-2-yl)-1,2,3,4-tetrahydronaphthalene, 2-(dicyclopropylmethylamino)-8-(oxazol-4-yl)-1,2,3,4-tetrahydronaphthalene, 2-ethylamino-8-(1,2,3-oxadiazol-4-yl)-thio-1,2,3,4-tetrahydronaphthalene, 2-n-butylamino-8-(5-methoxypyrimidin-2-yl)-1,2,3,4-tetrahydronaphthalene, 2-(di-n-propylamino)-8-(5-chlorooxazol-2-yl)-1,2,3,4-tetrahydronaphthalene, 2-(di-n-propylamino)-8-(pyrimidin-2-yl)-1,2,3,4-tetrahydronaphthalene, 2-(di-n-propylamino)-8-(2-aminopyrimidin-4-yl)-1,2,3,4-tetrahydronaphthalene, 2-(di-n-propylamino)-8-(3-phenyl-1,2,4-oxadiazol-5-yl)-1,2,3,4-tetrahydronaphthalene, 2-(di-n-propylamino)-8-(3-methyl-1,2,4-oxadiazol-5-yl)-1,2,3,4-tetrahydronaphthalene, 2-(di-n-propylamino)-8-(pyrazin-2-yl)-1,2,3,4-tetrahydronaphthalene, 2-(di-n-propylamino)-6-(bromopyrazin-2-yl)-1,2,3,4-tetrahydronaphthalene, 2-(di-n-propylamino)-8-(benzothiazol-2-yl)-1,2,3,4-tetrahydronaphthalene, 2-(di-n-propylamino)-8-(benzoxazol-2-yl)-1,2,3,4-tetrahydronaphthalene, 2-(di-n-propylamino)-8-(indol-3-yl)-1,2,3,4-tetrahydronaphthalene, 5-(isoxazol-5-yl)-3-(dipropylamino)chromane, 5-(3-methylisoxazol-5-yl)-3-(dipropylamino)chromane, 5-(4-methylisoxazol-5-yl)-3-(dipropylamino)chromane, 5-(3,4-dimethylisoxazol-5-yl)-3-(dipropylamino)chromane, 5-(3-methylisoxazol-5-yl)-3-(dipropylamino)thiochromane, 5-(4-methylisoxazol-5-yl)-3-(dipropylamino)thiochromane, 5-(3,4-dimethylisoxazol-5-yl)-3-(dipropylamino)thiochromane, 8-(4,5,6,7-tetrahydrobenz[c]isoxazol-1-yl)-2-(dimethylamino)tetrahydronaphthalene, and 3-(di-n-propylamino)-5-(isoxazol-2-yl)-1,2,3,4-tetrahydronaphthalene.

A preferred compound of Formula IX has the following structure:

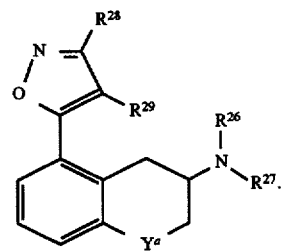

Wherein $R^{26}$, $R^{27}$, $R^{28}$, $R^{29}$, and $Y^a$ are as defined supra.

When Q is hydrogen, preferred compounds of Formula I have the following structure:

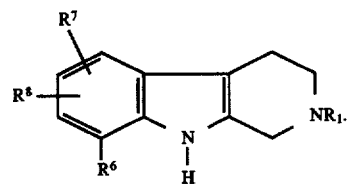

Wherein $R^6$ is selected from the group consisting of $C_1$–$C_4$ alkyl, $OR_5$, fluoro, bromo, and chloro;

$R_5$ is $C_1$–$C_4$ alkyl; and $R_1$, $R_7$, and $R_8$ are as defined supra.

The 5-$HT_{2B}$ receptor has been identified in various tissues and organs in the rat. The primary areas of 5-$HT_{2B}$ receptor localization in the rat include lung, uterus, bladder, stomach, and colon. Further, the 5-$HT_{2B}$ receptor has been identified in various tissues and organs in the human. Interesting areas of 5-$HT_{2B}$ receptor localization in the human include but are not limited to the brain and blood vessels.

In light of the receptor localization, physiological conditions which can be mediated by the 5-$HT_{2B}$ receptor include incontinence, bladder dysfunction, Functional Bowel Disorders, stomach emptying disorders, respirator/disorders including astra, uterine dysfunction including endometriosis, fibrosis, and motility disorders such as but not limited to induction of labor, sleeping disorders, eating disorders, including bulimia and obesity, consumption disorders, thermoregulation, sexual disorders, hyperactivity, excessive aggression, alcoholism, anxiety, obsessive-compulsive disorders, depression, psychosis, schizophrenia and schizophreniform disorders, panic disorders, Gilles de la Tourette syndrome, and Alzheimer's disease and cardiovascular diseases such as thrombosis, hypertension, vasospasm (peripheral and/or central) such as stroke, angina, and other vascular occlusive diseases. Further, migraine headaches can be treated using 5-$HT_{2B}$ receptor stimulating compounds of this invention. Preferred examples of such conditions which may be treated using 5-$HT_{2B}$ modulators include cardiovascular disorders, uterine dysfunction, sleep disorders, hallucinogenic activity, psychosis, anxiety, depression, thermoregulation, feeding disorders, and hypotension. See Leonard, B. E., *International Clinical Psychopharmacology*, 7, 13–21 (1992). It is particularly preferred to use a 5-$HT_{2B}$ antagonist for treating a Functional Bowel Disorder.

Several examples of more specific CNS disorders which may be treated using 5-$HT_{2B}$ modulating compounds of this invention include, but are not limited to: (numerals in parenthesis refer to the DSM-III-R Classification Codes) Attention-deficit hyperactivity disorder (314.01), conduct disorders (312.20, 312.00, 312.90), primary degenerative dementia of the Alzheimer type, senile onset (290.30, 290.20, 290.21, 290.00), primary degenerative dementia of the Alzheimer type, presenile onset (290.11, 290.12, 290.13, 290.10), alcohol withdrawal delirium (291.00), alcohol hallucinosis (291.30), alcohol, dementia associated with alcoholism (291.20), cannabis, delusional disorder (292.11), cocaine, intoxication (305.60), hallucinogen, mood disorder (292.84), nicotine withdrawal (292.00), phencyclidine or similarly acting arylcyclohexylamine intoxication (305.90), other psychoactive substance intoxication (305.90), delirium (293.00), dementia (294.10), organic delusional disorder (293.81), organic hallucinosis (293.82), organic mood disorder (293.83), organic anxiety disorder (294.80), organic personality disorder (310.10), organic mental disorder (294.80), schizophrenia, catatonic (295.21, 295.22, 295.23, 295.24, 295.25, 295.20), schizophrenia, disorganized (295.11, 295.12, 295.13, 295.14, 295.15, 295.00), schizophrenia, paranoid (295.31, 295.32, 295.33, 295.34, 295.35, 295.00), schizophrenia, undiffertiated (295.91, 295.92, 295.93, 295.94, 295.95, 295.00), schizophrenia, residual (295.61, 295.62, 295.63, 295.64, 295.65, 295.60), delusional (paranoid disorder (297.10), schizophreniform disorder (295.40), schizoaffective disorder (295.70), induced psychotic disorder (297.30), bipolar disorder, mixed (296.61, 296.62, 296.63, 296.64, 296.65, 296.66, 296.60), bipolar disorder, manic (296.41, 296.42, 296.43, 296.44, 296.45, 296.46, 296.40), bipolar disorder, depressed (296.51, 296.52, 296.53, 296.54, 296.55, 296.56, 296.50), major depression, single episode (296.21, 296.22, 296.23, 296.24, 296.25, 296.26, 296.20), major depression, recurrent (296.31, 296.32, 296.33, 296.34, 296.35, 296.36, 296.30), obsessive compulsive disorder (300.30), post-traumatic stress disorder (309.89), generalized anxiety disorder (300.02), hypochondriasis (300.07), somatization disorder (300.81), male erectile disorder (302.72), intermittent explosive disorder (312.34), impulse control disorder (312.39), paranoid (301.00), schizoid (301.20), schizotypal (301.22), antisocial (301.70), and borderline (301.83). *Diagnostic and Statistical Manual of Mental Disorders*, 3rd Ed. Revised, (1980), prepared by the Task Force on Nomenclature and Statistics of the American Psychiatric Association.

Thus, the present invention also provides methods for treating or preventing the above-named conditions.

The skilled artisan will recognize that psychosis or psychotic conditions are characterized by hallucinations, delusions, or grossly disorganized behavior which indicate that the patient suffers from gross impairment in reality testing. Therefore, drugs having antipsychotic activity can be useful for treating a variety of important psychotic conditions.

As used herein the term "Functional Bowel Disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "Functional Bowel Disorder" includes but is not limited to irritable bowel syndrome, hypermotility, ichlasia, hypertonic lower esophogeal sphinctor, tachygastria, constipation, hypermotility associated with irritable bowel syndrome.

Functional Bowel Disorders are characterized by abnormal bowel function without detectable structural abnormalities. Abnormal bowel function includes diarrhea, constipation, mucorrhea, and pain or discomfort over the course of the sigmoid colon. Such disorders are influenced by psychological factors and stressful life situations.

The Functional Bowel Disorder, Irritable Bowel Syndrome (IBS), is one of the most commonly encountered gastrointestinal disorders. Between 20% and 50% of patients referred to gastrointestinal clinics suffer from IBS. Symptoms of IBS occur in approximately 14% of otherwise apparently healthy people. IBS is a complex condition, in part because it is not a disease but a syndrome composed of a number of conditions with similar manifestations.

Current therapy for Functional Bowel Disorders is restricted to drugs which treat only a small proportion of patients. For example, anticholinergic drugs reduce spasticity, thereby relieving some of the abdominal pain. Histamine H2 receptor antagonists inhibit gastric acid secretion and my relieve some dyspeptic symptoms. A therapeutic agent that relieves most of the Functional Bowel Disorder symptoms is currently not available.

The term Functional Bowel Disorder includes conditions such as Irritable Bowel Syndrome, ichlasia, hypertonic lower esophogeal sphincter, tachygastria, hypermotility associated with irritable bowel syndrome, and constipation.

The compounds described herein can form acid addition salts with a wide variety of inorganic and organic acids. Typical acids which can be used include sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like. The pharmaceutically acceptable acid addition salts are especially preferred for the treatment of $5\text{-HT}_{2B}$ receptor related conditions.

Certain compounds are preferred for use in treating conditions related to the modulation of a $5\text{-HT}_{2B}$ receptor. The following invention embodiments and compound characteristics listed in tabular form may be independently combined to produce a variety of preferred compounds and embodiments of the invention. The following list of embodiments of this invention is in no way intended to limit the scope of this invention in any way:

A) $R_1$ is hydrogen;

B) $R_2$ is hydrogen or methyl;

C) $R_3$ is hydrogen or methyl;

D) $R_4$ is $C_5$–$C_8$ cycloalkenyl or substituted $C_5$–$C_8$ cycloalkenyl, bicyclic or substituted bicyclic, wherein the substituents are selected from the group consisting of hydrogen, $C_1$–$C_6$ alkyl, $NO_2$, halo, halo($C_1$–$C_6$) alkyl, $C_2$–$C_6$ alkenyl, $COR_5$, ($C_1$–$C_6$ alkyl)$_m$amino, —$SR_5$, and $OR_5$.

E) A is a group of formula III;

F) A is a group of formula IV wherein $R_6$ and $R_7$ are $C_1$–$C_6$ alkyl or halo, and $R_8$ is hydrogen, $C_1$–$C_5$ alkyl, halo, $C_5$–$C_8$ cycloalkyl, phenyl or substituted-phenyl;

G) The compound interacting with the $5\text{-HT}_{2B}$ receptor is a $5\text{-HT}_{2B}$ receptor antagonist;

H) The compound interacting with the $5\text{-HT}_{2B}$ receptor is a $5\text{-HT}_{2B}$ receptor partial agonist;

I) $R_4$ is substituted $C_5$–$C_8$ cycloalkenyl; wherein the substituents are selected from the group consisting of hydrogen, $NO_2$, halo, ($C_1$–$C_6$ alkyl)$_m$amino, and $OR_5$;

J) A is a group of formula IV wherein $R_6$ is hydrogen, $R_7$ and $R_8$ are independently selected from the group consisting of halo and $C_1$–$C_4$ alkyl;

K) $R_4$ is naphthyl or substituted naphthyl wherein the naphthyl substituents are selected from the group consisting of ($C_1$–$C_6$ alkyl)$_m$amino and $OR_5$;

L) $Y^a$ is $CH_2$, $R^{26}$ and $R^{27}$ are each $C_2$–$C_3$ alkyl; and $R^{28}$ and $R^{29}$ are each hydrogen;

M) Compounds of the Formula I, II, III, IV, and V;

N) Compounds of the Formula II, III, and VIII;

O) Compounds of the Formula VI, VIII, IX, XI, and XII;

P) A compound of the Formula X;

Q) Compounds of wherein $R_6$ is methyl, $R_2$ is methyl, and $R_4$ is substituted alkenyl wherein the alkenyl group is phenyl and there are two substituents which are each methoxy;

R) The 5-$HT_{2B}$ modulated condtion is a Functional Bowel Disorder.

S) The Functional Bowel Disorder is irritable bowel syndrome.

T) The 5-$HT_{2B}$ modulated condition is psychosis.

U) The 5-$HT_{2B}$ selective compound has a greater affinity for 5-$HT_{2B}$ receptors than it has for 5-HT2A receptors.

V) The 5-$HT_{2B}$ selective compound has a greater affinity for 5-$HT_{2B}$ receptors than it has for 5-$HT_{2C}$ receptors.

W) The 5-$HT_{2B}$ modulated condtion is selected from the group consisting of urinary incontinence, bladder dysfunction, uterine dysfunction, cardiovascular disorder, and respiratory disorder.

X) The compound is administered in a unit dosage form.

Y) The label on the article of manufacture states that the compound is useful for treating a condition selected from the group consisting of urinary incontinence, bladder dysfunction, uterine dysfunction, cardiovascular disorder, respiratory disorder, and Functional Bowel Disorder.

Z) A pharmaceutical formulation comprising one or more pharmaceutically acceptable exipients and a 5-$HT_{2B}$ receptor modulating compound;

Z1) A compound wherein $R_4$ is aromatic;

Z2) A compound wherein $R_4$ is an aromatic bicyclic;

Z3) A compound of Formula VII.

Certain compounds of Formula II are useful for modulating 5$HT_{2B}$ receptors. Certain compounds of Formula II within the scope of this invention are preferred for that use. The following invention embodiments and compound characteristics listed in tabular form may be independently combined to produce a variety of preferred compounds and embodiments of the invention. The following list of embodiments of this invention is in no way intended to limit the scope of this invention in any way.

A) $R_9$ and $R_{10}$ are each hydrogen.

B) $R_{11}$ is $C_1$–$C_3$ alkyl.

C) $R_{11}$ is chloro, fluoro, or bromo.

D) $R_{11}$ is —$OCH_3$.

E) $R_6$ is $C_1$–$C_4$ alkyl.

F) $R_6$ is methyl.

G) A method for binding a 5$HT_{2B}$ receptor using one or more compounds of Formula I and/or II.

H) A method of using one or more compounds of Formula I and/or II for treating a functional bowel disorder.

I) A method of using one or more compounds of Formula I and/or II which are useful for stimulation of the 5$HT_{2B}$ receptor for treating a condition selected from the group consisting of urinary incontinence, bladder dysfunction, uterine dysfunction, cardiovascular disorders, and respiratory disorders.

J) A method for using one or more compounds of Formula I and/or II for treating Irritable Bowel Syndrome.

K) A pharmaceutical formulation comprising a compound of Formula I or II and one or more pharmaceutically acceptable excipients.

The compounds of the present invention are useful for modulating or blocking the 5-$HT_2$ receptor. Certain of the present compounds of Formula XI and XII are preferred for that use. The following invention embodiments and compound characteristics listed in tabular form may be independently selected or combined to produce a variety of preferred compounds and embodiments of the invention. The following list of embodiments of this invention is in no way intended to limit the scope of this invention in any way.

A) $R_1$ is hydrogen;

B) $R_2$ is hydrogen or methyl;

C) $R_3$ is hydrogen or methyl;

D) $R_4$ is $C_5$–$C_8$ cycloalkenyl or substituted $C_5$–$C_8$ cycloalkenyl, wherein the substituents are selected from the group consisting of hydrogen, $C_1$–$C_6$ alkyl, $NO_2$, halo, halo($C_1$–$C_6$)alkyl, $C_2$–$C_6$ alkenyl, $COR_5$, ($C_1$–$C_6$ alkyl)$_m$ amino, —$SR_5$, and $OR_5$;

E) A is a group of formula III;

F) A is a group of formula IV wherein $R_6$ and $R_7$ are $C_1$–$C_6$ alkyl or halo, and $R_8$ is hydrogen, $C_1$–$C_5$ alkyl, halo, $C_5$–$C_8$ cycloalkyl, phenyl or substituted-phenyl;

G) $R_2$ is hydrogen;

H) $R_3$ is hydrogen;

I) $R_4$ is substituted $C_5$–$C_8$ cycloalkenyl; wherein the substituents are selected from the group consisting of hydrogen, $NO_2$, halo, ($C_1$–$C_6$ alkyl)$_m$ amino, and $OR_5$;

J) A is a group of formula IV wherein $R_6$ is hydrogen, $R_7$ and $R_8$ are independently selected from the group consisting of halo and $C_1$–$C_4$ alkyl.

K) Q' is (CHR$_2$)R$_4$;

L) $R^{30}$ and $R^{31}$ join to form a 3 to 6 member carbon ring;

M) $R^{30}$ and $R^{31}$ join to form a 3 to 5 member carbon ring;

N) $R^{30}$ and $R^{31}$ are each methyl;

O) $R_4$ is naphthyl;

P) $R_4$ is an optionally substituted bicyclic hydrocarbon ring system having 7 to 12 carbon atoms and 0, 1, 2, or 5 double bonds;

Q) $R_4$ is a 6 to 10 carbon atom unsaturated bicyclic ring system;

R) Q' is bicyclic or substituted bicyclic;

S) $R_{34}$ is

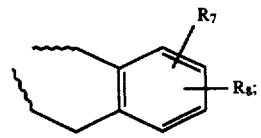

T) $R_{34}$ is an optionally substituted bicyclic ring substituent;

U) $R_9$ and $R_{10}$ are each hydrogen;

V) $R_9$ is selected from the group consisting of $C_1$–$C_6$ alkyl, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, $C_7$–$C_{20}$ arylalkyl;

W) $R_4$ is aromatic;

X) $R_{34}$ is spiro-bicyclic or substituted spiro-bicyclic;

Y) Q' is hydrogen.

The more preferred classes have the following features:

A–C, E or F, I, L, N, P, R, and W.

The most preferred class of compounds has the following features:

A, G–J, M, and Q.

The preferred classes of compounds for use as selective 5-HT$_{2B}$ ligands have the following features:

A–D, E or J, M, and O.

The most preferred class of compounds for use as selective 5-HT$_{2B}$ ligands has the following features:

A, G–J, M, and O.

Compounds of Formulas XI and XII are particularly useful for modulating 5HT$_{2B}$ receptors. Certain compounds within the scope of this invention are preferred for that use. The following invention embodiments and compound characteristics listed in tabular form may be independently selected or combined to produce a variety of preferred compounds and embodiments of the invention. The following list of embodiments of this invention is in no way intended to limit the scope of this invention in any way.

A) R$_9$ and R$_{10}$ are each hydrogen;

B) R$_{11}$ is C$_1$–C$_3$ alkyl;

C) R$_{11}$ is chloro, fluoro, or bromo;

D) R$_{11}$ is —OCH$_3$;

E) R$^{30}$ and R$^{31}$ join to form a 3 to 8 member carbon ring;

F) R$^{30}$ and R$^{31}$ join to form a 3 to 6 member carbon ring;

G) A compound having preferred characteristics described supra.;

H) A method for binding a 5HT$_{2B}$ receptor using one or more compounds of Formula XI and/or XII;

I) A method of using one or more compounds of Formula XI and/or XII for treating a functional bowel disorder.

I) A method of using one or more compounds of Formula XI and/or XII which are useful for modulatation of the 5HT$_{2B}$ receptor for treating a function bowel disorder.

J) A method for using one or more compounds of Formula XI and/or XII for treating Irritable Bowel Syndrome.

K) A pharmaceutical formulation comprising a compound of Formula XI and/or XII and one or more pharmaceutically acceptable excipients.

Examples of compounds of Formula XI include but are not limited to: 10-methyl-2,3,4,4a,5,6,7,11c-octahydro-1H-indolo[2,3-c]quinotine, 8-chloro-2,3,4,4a,5,6,7,11c-octahydro-1H-indolo[2,3-c]quinoline, 6-(2,4-dimethoxybenzyl)-10-methyl-2,3,4,4a,5,6,7,11c-octahydro-1H-indolo[2,3-c]quinoline, 7-fluoro-6-(2,4-dimethoxybenzyl)-10-methyl-2,3,4,4a,5,6,7,11c-octahydro-1H-indolo [2,3-c]quinoline, 8-methoxy-6-(2,4-dimethoxybenzyl)-10-methyl-2,3,4,4a,5,6,7,11c-octahydro-1H-indolo[2,3-c]quinoline, 7-nitro-6-(3,4-dimethoxybenzyl)-10-methyl-2,3,4,4a,5,6,7,11c-octahydro-1H-indolo[2,3-c]quinoline, 5-(2,4-dimethoxybenzyl)-10-methyl-2,3,4,4a,5,6,7,11c-octahydro-1H-indolo[2,3-c]quinoline, 7-bromo-5-(2,4-dimethoxybenzyl)-10-methyl-2,3,4,4a,5,6,7,11c-octahydro-1H-indolo[2,3-c]quinoline, 6-ethoxy-5-(3,4-dimethoxybenzyl)-10-methyl-2,3,4,4a,5,6,7,11c-octahydro-1H-indolo[2,3-c]quinoline, 7-nitro-6-(3,4-dimethoxybenzyl)-10-methyl-2,3,4,4a,5,6,7,10c-octahydro-1H-indolo[2,3-c]quinoline, 7-(3,4-dimethoxybenzyl)-10-methyl-2,3,4,4a,5,6,7,11c-octahydro-1H-indolo[2,3-c]quinoline, 7-nitro-6-(3,4-diethoxybenzyl)-10-methyl-2,3,4,4a,5,6,7,11c-octahydro-1H-indolo[2,3-c]quinoline, 6-methyl-8-bromo-1-[(3,4-dimethoxyphenyl)-10-methyl-2, 3,4,4a,5,6,7,11c-octahydro-1H-indolo[2,3-c]quinoline, 7-(1, 1-dimethylethyl)-5-(1-naphthalenyl-1-ethyl)-1,2,3,4,4a,5,6, 10c-pyrido [3,4-b]indole hydrochloride, 7-methyloxy-1-(2-methylaminonaphthalenyl)-1-ethyl)-1,2,3,4,4a,5,6,10c-octahydrocyclopenta[a]pyrido [3,4-b]indole, (Z)2-butenedioate, 6-(1,1-dimethylethyl)-1-(1-(3-diethylaminonaphthalenyl)-1-ethyl)-1,2,3,4,4a,5,6,10c-octahydrocyclopenta[a]pyrido-[3,4-b]indole hydrochloride, and 6-methyl-5-[(4-dimethylamino-naphthalenyl)-methyl]-1,2,3,4,4a,5,6,10c-octahydrocyclopenta[a]pyrido-[3,4-b] indole dihydrochloride.

Examples of compounds of Formula XII include but are not limited to: 3-(2-amine-cyclopentyl)-6,7-dimethylindole, 3-(2-amine-cyclopentyl)-5-methyl-7-bromoindole, 3-(2-amine-cyclopentyl)-6-methyl-7-chloroindole, 3-(2-amine-cyclopentyl)-6-bromo-7-methylindole, 3-(2-amine-cyclopentyl)-Benz(G)indole, 3-(2-amine-cyclohexyl)-5-methyl-7-chloroindole, 3-(2-amine-cyclohexyl)-7-chloroindole, 3-(2-amine-cyclopropyl)-7-methoxyindole, 3-(2-amine-cycloheptyl)-7-fluoroindole, 3-(2-amine-cyclohexyl)-7-bromoindole, 3-(2-amine-cyclopropyl)-6-methyl-7-bromoindole, 3-(2-amine-cyclopentyl)-5-fluoro-7-methoxyindole, 3-(2-amine-cyclopentyl)-5-nitro-7-chloroindole, 3-(2-amine-cyclooctyl)-2-ethyl-7-fluoroindole, and 3-(2-amine-cycloheptyl)-2-methyl-7-fluoroindole.

The compounds which are useful for blocking 5-HT$_{2B}$ receptors contemplates racemic mixtures as well as the substantially pure stereoisomers of the compounds of Formulas I through XII. The term "enantiomer" is used herein as commonly used in organic chemistry to denote a compound which rotates the plane of polarization. Thus, the "–enantiomer" rotates the plane of polarized light to the left, and contemplates the levorotary compound of Formulas I through XII. The + and − enantiomers can be isolated using well-known classical resolution techniques. One particularly useful reference which describes such methods is JACQUES et. al. ENANTIOMERS, RACEMATES, AND RESOLUTIONS (John Wiley and Sons 1981). Appropriate resolution methods include direct crystallization, entrainment, and crystallization by optically active solvents. Chrisey, L. A. Heterocycles, 267, 30 (1990). A preferred resolution method is crystallization with an optically active acid or by chiral synthesis as described in Example 46 using the method of A. I. Meyers. Loewe, M. F. et al., Tetrahedron Letters, 3291, 26 (1985), Meyers, A. I. et al., J. Am. Chem. Soc., 4778, 110 (1988). Preferred optically active acids include camphorsulfonic and derivatives of tartaric acid.

The present invention encompasses both the R and the S configurations. The terms "R" and "S" are used herein as commonly used in organic chemistry to denote the specific configuration of a chiral center. See, R. T. Morrison and R. N. Boyd, Organic Chemistry, pp 138–139 (4th Ed. Allyn & Bacon, Inc., Boston) and Orchin, et al. The Vocabulary of Organic Chemistry, p. 126, (John Wiley and Sons, Inc.).

For example, the present invention includes, but is not limited to, the use of compounds such as (−)-(S)-7-methyl-8-bromo-1-[(3,4-dimethoxyphenyl)methyl]-1,2,3,4-tetrahydro-9H-pyrido[3,4-b]indole; (−)-(S)-5,7-dimethyl-1, 2,3,4-tetrahydro-1-[(3,4-dimethoxyphenyl)methyl]-9H-pyrido[3,4-b]indole; (−)-(S)-5-fluoro-6-methyl-1-[(2-chloro-3,4-dimethoxyphenyl)methyl]-1,2,3,4-tetrahydro-9H-pyrido[3,4-b]indole; and (−)-(S)-6-methyl-1,2,3,4-tetrahydro-1-[(3,4-dimethylphenyl)methyl]-9H-pyrido[3,4-b]indole. The invention also includes, but is not limited to, the use of (+)-(S)-7-methyl-8-bromo-1-[(3,4-dimethoxyphenyl)methyl]-1,2,3,4-tetrahydro-9H-pyrido[3, 4-b]indole; (+)-(S)-5,7-dimethyl-1,2,3,4-tetrahydro-1-[(3,4-dimethoxyphenyl)methyl]-9H-pyrido[3,4-b]indole; (+)-(S)-5-fluoro-6-methyl-1-[(2-chloro-3,4-dimethoxyphenyl) methyl]-1,2,3,4-tetrahydro-9H-pyrido[3,4-b]indole; (−)-(R)-7-methyl-8-bromo-1-[(3,4-dimethoxyphenyl)methyl]-1,2, 3,4-tetrahydro-9H-pyrido[3,4-b]indole; (−)-(R)-5,7- dimethyl-1,2,3,4-tetrahydro-1-[(3,4-dimethoxyphenyl)
methyl]-9H-pyrido[3,4-b]indole; (−)-(R)-5-fluoro-6-
methyl-1-[(2-chloro-3,4-dimethoxyphenyl)methyl]-1,2,3,4-
tetrahydro-9H-pyrido[3,4-b]indole; and (−)-(R)-6-methyl-1,
2,3,4-tetrahydro-1-[(3,4-dimethylphenyl)methyl]-9H-
pyrido[3,4-b]indole; (+)-(R)-7-methyl-8-bromo-1-[(3,4-
dimethoxyphenyl)methyl]-1,2,3,4-tetrahydro-9H-pyrido[3,
4-b]indole; (+)-(R)-5,7-dimethyl-1,2,3,4-tetrahydro-1-[(3,4-
dimethoxyphenyl)methyl]-9H-pyrido[3,4-b]indole; (+)-(R)-
5-fluoro-6-methyl-1-[(2-chloro-3,4-dimethoxyphenyl)
methyl]-1,2,3,4-tetrahydro-9H-pyrido[3,4-b]indole; and
(+)-(S)-6-methyl-1,2,3,4-tetrahydro-1-[(3,4-
dimethylphenyl)methyl]-9H-pyrido[3,4-b]indole.

The compounds which are useful for interaction with
5-HT$_{2B}$ receptors are known to form hydrates and solvates
with appropriate solvents. Preferred solvents for the preparation of solvate forms include water, alcohols,
tetrahydrofuran, DMF, and DMSO. Preferred alcohols are
methanol and ethanol. Other appropriate solvents may be
selected based on the size of the solvent molecule. Small
solvent molecules are preferred to facilitate the corresponding solvate formation. The solvate or hydrate is typically
formed in the course of recrystallization or in the course of
salt formation. One useful reference concerning solvates is
Sykes, Peter, *A Guidebook to Mechanism in Organic
Chemistry*, 6, 56, (1986, John Wiley & Sons, New York).
The term "solvate" as used herein includes hydrate forms
such as monohydrate and dihydrates.

Some of the compounds which are useful for interaction
with 5-HT$_{2B}$ receptors are either known in the art or readily
available by routine synthetic processes. For example, compounds of Formula III can be prepared using the methods
taught in Semonsky et al., U.K. Patent No. 816,273 (Jul. 8,
1959), U.S. Pat. Nos. 2,736,728 and 2,774,763 which U.S.
Patents are hereby incorporated by reference. Compounds of
Formula IV may be prepared as described in U.S. Pat. Nos.
4,981,859 and 4,931,447 which are hereby incorporated by
reference. A process for preparing compounds of Formula V
is described in U.S. Pat. No. 4,902,691 which is hereby
incorporated by reference. A process for preparing compounds of Formula VI is described in U.S. Pat. No. 4,563,
461 which is hereby incorporated by reference. A compound
of Formula VII can be prepared as described in Forbes, I. T.,
*J. Med. Chem.*, 36:1104–1107 (1993). A compound of
Formula VIII is known in the art and may be purchased or
prepared by recognized methods. A process for preparing
compounds of Formula IX is available to the artisan in the
published European Patent application. The European Publication number is 0498590 A1 (Aug. 12, 1992; Bulliten
92/33) and is readily available to the United States artisan in
the English language. A compound of Formula X is known
in the art and can be prepared by recognized methods.

The compounds of the present invention can be prepared
using chemical processes that are understood in the art;
however, the most preferred method for preparing the formula I compounds of this invention utilizes the process of
Scheme V. The most preferred method for preparing a
compound of Formula II is using the general method illustrated in Scheme II infra. Compounds of Formula II wherein
R$_9$, R$_{12}$, and/or R$_{10}$ are not hydrogen can be prepared using
accepted chemical methods such as reductive alkylation and
direct alkylation of the corresponding tryptamine.

A compound of Formula I, wherein Q is hydrogen, may
be prepared by contacting glyoxylic compound of formula
(i) with an amine of formula (h). This Pictet-Spengler type
reaction is generally applicable, provides desirable yields,
and produces stable intermediates. Further, the product of
the reaction typically may be directly isolated as the desired
salt.

The compounds of formula (a) which may be used as
starting materials for the compounds of the instant invention
can be purchased from art-recognized vendors or may be
prepared using well-known chemical techniques. The compounds of formula (b) which are useful as starting materials
for the compounds of this invention may be prepared as
represented by Scheme I. The R$_4$ group is as defined herein
above.

The process for preparing the compounds of this invention will be discussed in greater detail in the following
paragraphs.

Scheme I

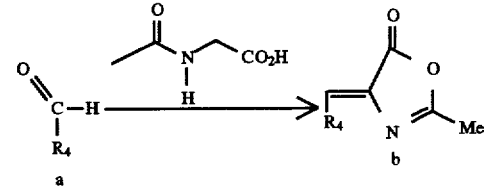

Compound (a) in Scheme I may be substituted or unsubstituted depending on the desired product. Most formula (a)
compounds necessary for the preparation of the azalactone
(b) starting materials are commercially available. Additional
substituted formula (a) compounds may prepared using
common chemical methods. Furniss, B. S. et al., *Vogel's
Textbook of Practical Organic Chemistry* (John Wiley, New
York, N.Y. 1989) see especially pp 989 through 993.

Generally, the Scheme I reaction is begun by preparing a
solution of compound (a), acetylglycine and sodium acetate
in acetic anhydride. The reaction is commonly heated from
about 90° C. to about 110° C. for a period of about 2–15
hours. The reaction mixture is cooled to about ambient
temperature and stirred for a period of about 0–10 hours
under inert conditions. The reaction time will vary depending on the degree of substitution on the R$_4$ group and the
completion of reaction desired.

When the reaction is complete, the mixture is poured onto
ice with stirring. The azalactone (b) may be isolated by
standard isolation techniques such as filtration and may be
dried under reduced pressure.

Compound (d) in Scheme II is used as a starting material
for compounds of Formula I. These compounds are commercially available or may be prepared using the well-
known Fischer indole synthesis applied to tryptamines. The
Fischer synthesis is represented by Scheme II. "A" is as
hereinabove defined.

Scheme II

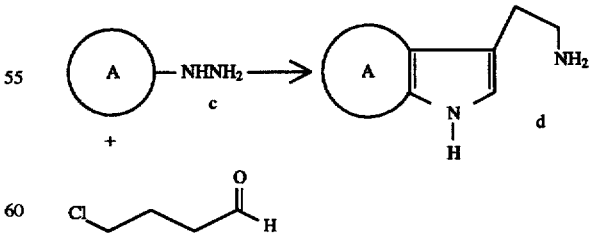

The chlorobutanal compound used in Scheme II may be
prepared through the hydrogenation of chlorobutyryl chloride. The hydrogenation may be facilitated by the use of a
catalyst such as Pd/C. Other halobutanal compounds may be
suitable for the Scheme II process. The starting compounds (c) in Scheme II may be purchased or prepared using known methods. March, J., *Advanced Organic Chemistry Reactions, Mechanisms, and Structure*, 3rd (John Wiley & Sons, New York, 1985) see especially page 1163.

The Fischer synthesis is commonly begun by adding a suitable saturated base like sodium carbonate to a stirred suspension of the hydrazine salt in an organic solvent like chloroform. The hydrazine hydrochloride salt is one especially preferred hydrazine salt. The desired hydrazine free base is extracted with the organic phase. The oil is placed in an alcohol and water solution and treated with an appropriate base like sodium acetate. The halobutanal is added and the tube purged with an inert gas like nitrogen. The resulting mixture is placed in an oil bath which has been heated to about 90° C.–110° C. The mixture should be heated for about 17 to 19 hours. The mixture is allowed to cool to ambient temperature and is concentrated under reduced pressure. The residue is partitioned between a suitable organic and basic aqueous phase, such as chloroform/methanol and aqueous sodium carbonate. The organic phase may be concentrated and the resulting compound (d) purified by standard methods such as flash chromatography. If chromatography is used, fractions containing product may be combined and concentrated. The oil is dissolved in an appropriate solvent, such as diethyl ether containing about 1% alcohol. A preferred alcohol is methanol. The mixture may be treated with dry acid gas, such as dry HCl gas to produce the corresponding acid addition salt of the desired compound (d).

One method for preparing Formula I compounds uses the Pictet-Spengler reaction as represented by Scheme III. The substituents are as defined hereinabove.

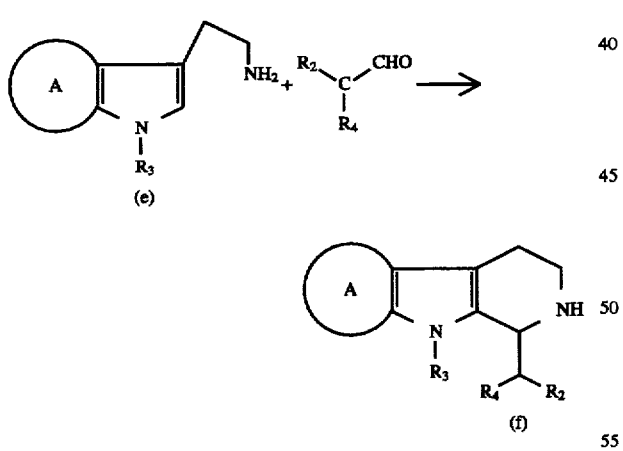

Generally, the Scheme III reaction is carried out by reacting compound (e) with the selected aldehyde in a suitable solvent such as ethanol or methanol for a period of about 1 to 50 hours depending on the desired product. The reaction may be refluxed if necessary. The precipitated reaction product is collected by common isolation methods, such as filtration and may be purified by recrystallization. If a compound with an $R_1$ substituent is desired, the reaction may be followed by a reductive alkylation. The reductive alkylation is represented by Scheme IV.

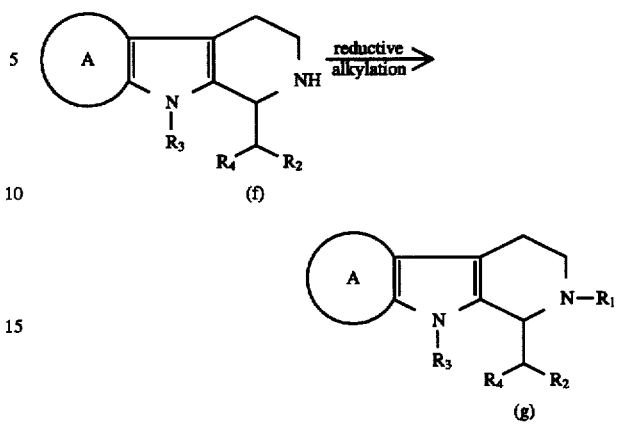

A protic acid and aldehyde solution is commonly added to an aqueous solution of compound (f). The most preferred protic acid is formic acid. The most preferred aldehyde is formaldehyde. The artisan can readily choose other appropriate reagents to facilitate the reductive alkylation. The resulting solution is refluxed for a period of about 4 to 80 hours. After reflux the solution should be made basic using an appropriate base such as potassium carbonate. The desired product can then be extracted with an appropriate organic phase, such as chloroform. The product can be dried, concentrated, and purified by known methods such as flash chromatography.

A preferred method for preparing certain Formula I compounds, wherein $R_2$ is hydrogen, utilizes the modified Pictet-Spengler reaction described supra, as represented by Scheme V. The substituents are as defined hereinabove.

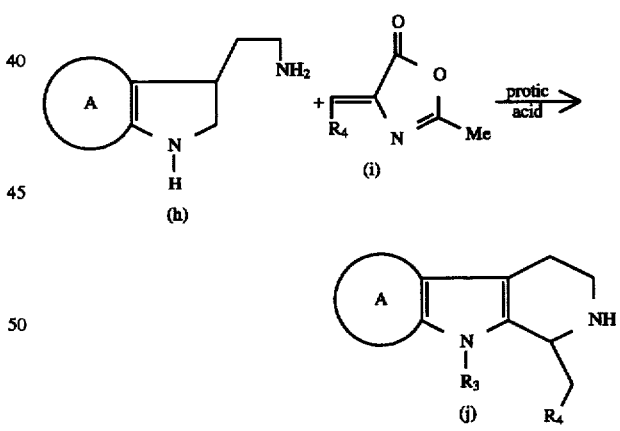

Compound (h) and compound (i) are contacted in a suitable protic aqueous acid solution. When compounds having hydrogen at the 1-position are desired, glyoxylic acid may be used in place of (i). This step may be completed under inert conditions. Compound (h) and compound (i) may be refluxed under atmospheric or inert conditions for a period of about 20 to about 30 hours. Preferred protic acids include sulfuric acid and hydrochloric acid. The most preferred acid solution is 1N HCl. If direct isolation is not effective, then the reaction mixture may be neutralized with an appropriate base, such as potassium carbonate, followed by extraction with an organic phase, such as chloroform. The product can be isolated through solvent removal followed by chromatographic isolation, such as silica gel chromatography, or other common isolation techniques. Typically the product is isolated as the acid addition salt. Appropriate salt forms are discussed supra.

As noted above, the compounds of the present invention can exist as resolved enantiomers. The single (−)enantiomer may be prepared by the chemical resolution method of A. I. Meyers as represented by Scheme VI infra. The (+)enantiomer may be prepared using known resolution techniques described supra. All substituents are as defined hereinabove.

chloromethylmethyl ether (MOMCl) are added to the solution, as represented by step 2. The mixture is stirred for a period of about 1 hour. The mixture can be treated with water and partitioned between an appropriate organic, such as diethyl ether, and water. The product should be extracted with the organic phase, dried over potassium carbonate, and concentrated. The resulting oil may be used in subsequent steps without further purification.

In step 3, n-BuLi is slowly added dropwise to a stirred, cooled (about −76° C. to −80° C.) solution of the formadine in dry THF. The solution is stirred for a period of about 1 hour followed by addition of the chloro compound in dry

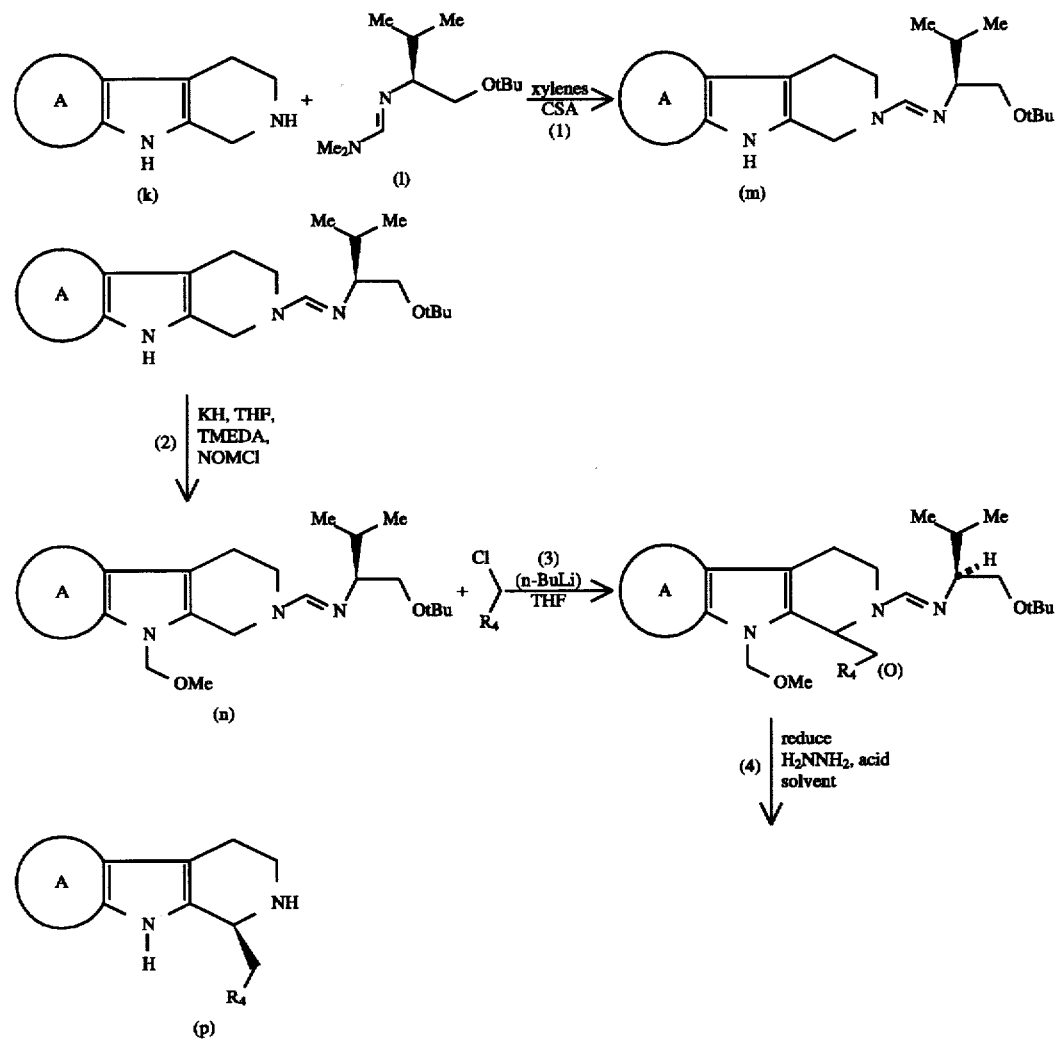

Scheme VI

In Scheme VI, CSA represents camphorsulfonic acid. Butylformadine (l) is prepared from the amino acid valine using known methods. Other formadine compounds will also work. In step 1, the compound (k) and butylformadine (l) solution is refluxed for a period of about 70 to 80 hours. The product of the reflux reaction can be purified by standard isolation methods, such as flash chromatography. The isolated oil can be used without further purification.

Compound (m) prepared in step 1, can be added to a suspension of potassium hydride (KH) in tetrahydrofuran (THF). Tetramethylethylenediamine (TMEDA) and then THF. The solution is stirred for an additional period of about 4–5 hours at the reduced temperature. The mixture is allowed to cool to room temperature for a period of about 4 to 14 hours. Wet THF is added and the solution concentrated. The residue is dissolved in an appropriate organic solvent such as chloroform and washed with water. The organic phase is dried over a suitable drying agent, such as sodium carbonate, and concentrated to facilitate purification of the desired product. The product may be isolated by flash chromatography and concentrated. The resulting oil may be used in subsequent steps without further purification.

The deprotection reaction represented in step 4 is begun at reduced temperature (about 0° C.). Water, acetic acid, and hydrazine hydrate are added to compound (o). The reaction temperature is decreased to about −10° C. to −20° C. for a period of about 60–120 hours. The mixture is allowed to warm to ambient temperature and is concentrated. The product is dissolved in an appropriate organic phase, such as chloroform, and washed with water. The organic phase is dried over a suitable drying agent, such as sodium carbonate, and concentrated to a viscous oil. The oil is dissolved in an appropriate solvent, such as diethyl ether and treated with a suitable organic or inorganic acid to afford the desired acid addition salt. The salt can be isolated and purified by common chemical methods.

If the desired product has an alkyl group at the $R_3$ position, the reaction represented by Scheme VII may be employed.

The solution of the concentrated compound (s) can be used directly in the next step. It is contacted with an appropriate solvent, such as methanol, and treated with hydrazine. The mixture is refluxed for a period of about 2 hours. The mixture is cooled to ambient temperature and treated with concentrated acid, such as HCl. The mixture is then treated with an alcohol and refluxed for a period of about 12 to 20 hours. Preferred alcohols include methanol, ethanol, and butanol. After cooling to ambient temperature, the mixture is partitioned between a suitable organic and an aqueous phase. One suitable combination is chloroform and concentrated sodium carbonate solution. The aqueous layer may be further extracted, the organic phases combined, dried, and concentrated. The product may be purified by flash chromatography, concentrated, and converted to a desired salt. The resulting compound (t) may be used in Scheme III or Scheme V to produce the desired Formula I compound.

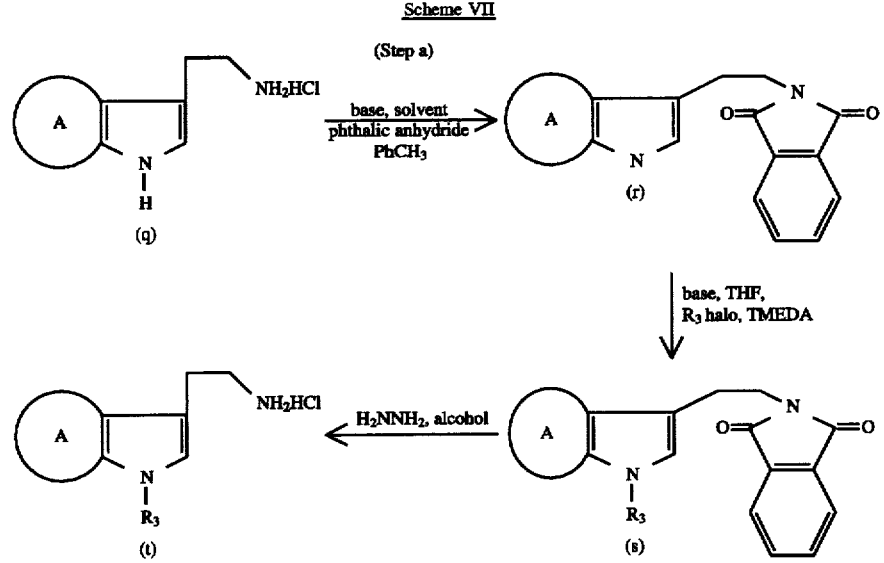

In Scheme VII, an appropriate saturated base solution, such as sodium carbonate, is added to compound (g). The desired compound (g) salt may be prepared by the method of Scheme II, above. The mixture is stirred at about ambient temperature for a period of about 1 hour. The layers are separated, and the aqueous layer is extracted with an appropriate organic solvent, such as chloroform. The organic layers are dried over an appropriate drying agent, such as sodium sulfate, and concentrated. The residue is dissolved in a suitable solvent such as toluene and treated with phthalic anhydride. The solution is refluxed for a period of about 12 to 20 hours with azeotropic drying. The solution is cooled, concentrated, and recrystallized to give compound (r).

In the next step, compound (r) is mixed in THF. A cooled (about 0° C.) suspension of an appropriate base, such as potassium hydride in dry THF, is slowly added to the compound (r) solution. After the addition of the the base, the mixture is stirred for a period of about 1 hour. Tetramethylethylenediamine (TMEDA) is added, followed by a haloalkyl such as methyl iodide (MeI). After about 1 hour, the reaction is quenched by the addition of water, followed by extraction with an appropriate organic phase, such as diethyl ether. The organic phases are dried over an appropriate drying agent, such as magnesium sulfate and concentrated.

Compounds of Formulas XI and XII may be prepared using the methods described supra. However, a preferred method for preparing compounds of Formula XI and XII is illustrated by Scheme VIII

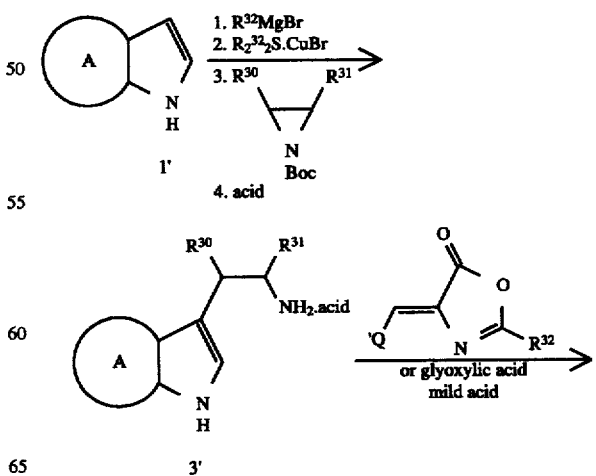

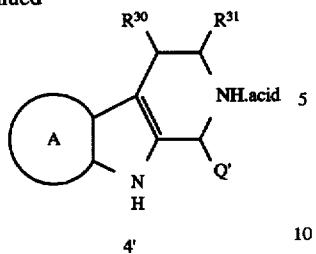
wherein $R^{32}$ is independently selected from $C_1$–$C_6$ alkyl; A, and Q' are defined supra.
Further, compounds of Example 108 can be prepared as illustrated by the following Scheme:
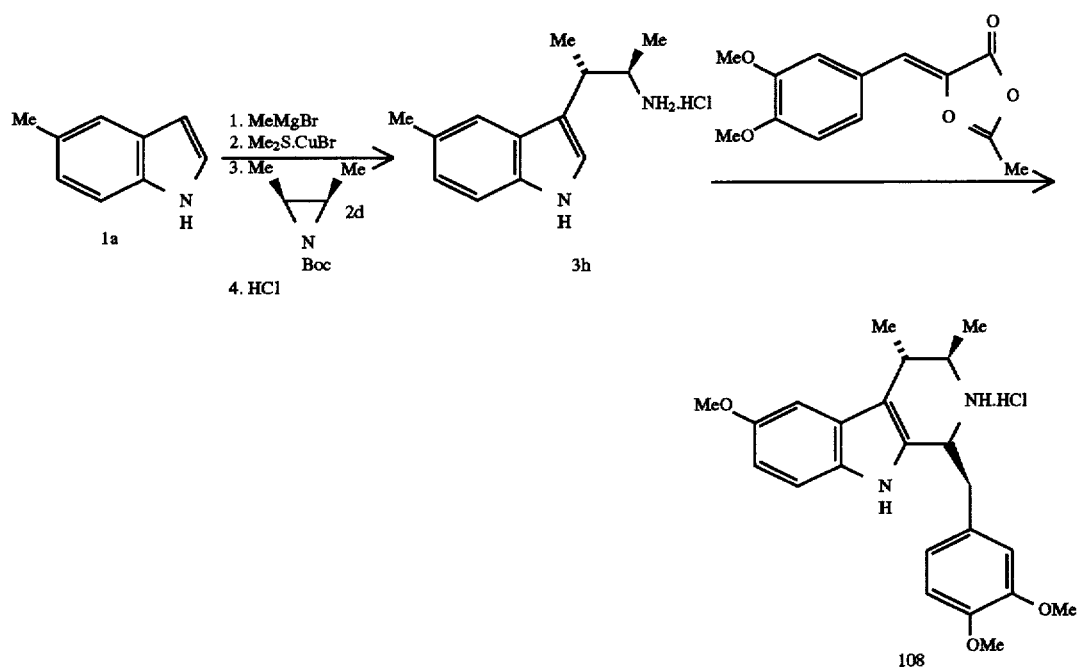
Similarly, compounds of Example 109 can be prepared as illustrated by the following Scheme:
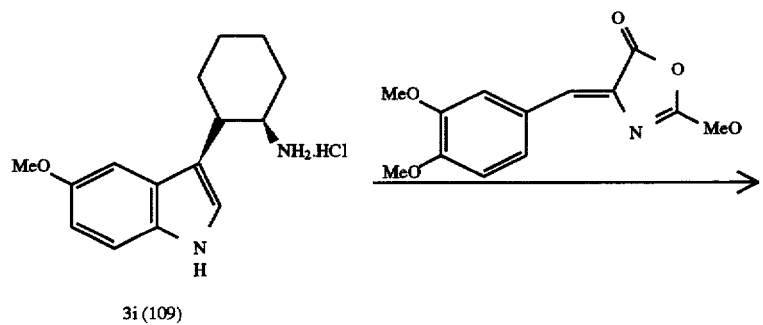

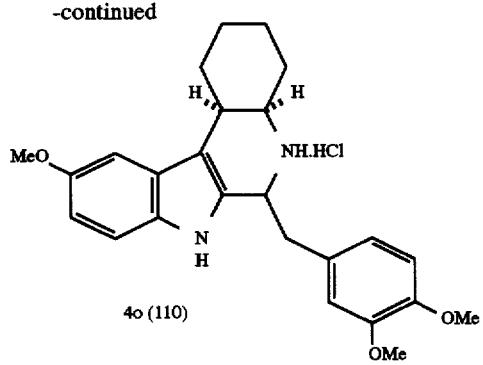

4o (110)

The following Examples further illustrate the preparation of certain of the Formula I, II, XI, and XII compounds. The examples are illustrative only, and are not intended to limit the scope of the invention.

The column chromatography procedures used standard flash chromatography techniques. One well-known reference describing appropriate flash chromotagraphy techniques is Still, W. C. Kahn, and Mitra, *J. Org. Chem.* 1978, 43, 2932. Fractions containing product were generally evaporated under reduced vacuum to provide the product.

Optical rotations were obtained using methanol, pyridine, or other suitable solvent.

The hydrochloride salt of the particular compound was prepared by placing the free base into diethyl ether containing an alcohol such as methanol or other suitable solvent mixture. While stirring this ether solution, a solution of HCl in diethyl ether was added dropwise until the solution became acidic. Alternatively, the ether solution was treated with dry HCl gas.

The maleate salt of the particular compound was prepared by placing the free base in ethyl acetate or other suitable solvent and treating with maleic acid. The precipitate formed was filtered and dried to provide the corresponding hydrochloride or maleate salt of the free base.

Compounds of Formulas I through VI and VIII through XII are more preferred for treating a mammal suffering from or susceptible to a condition associated with abnormal or dysfunctional 5-$HT_{2B}$ receptor stimulation. Additionally, compounds of Formulas I through VI and VIII through XII are more preferred for blocking a 5-$HT_{2B}$ receptor in a mammal or in vitro. Finally, compounds of Formulas I through VI and VIII through XII are more preferred for use in an article of manufacture.

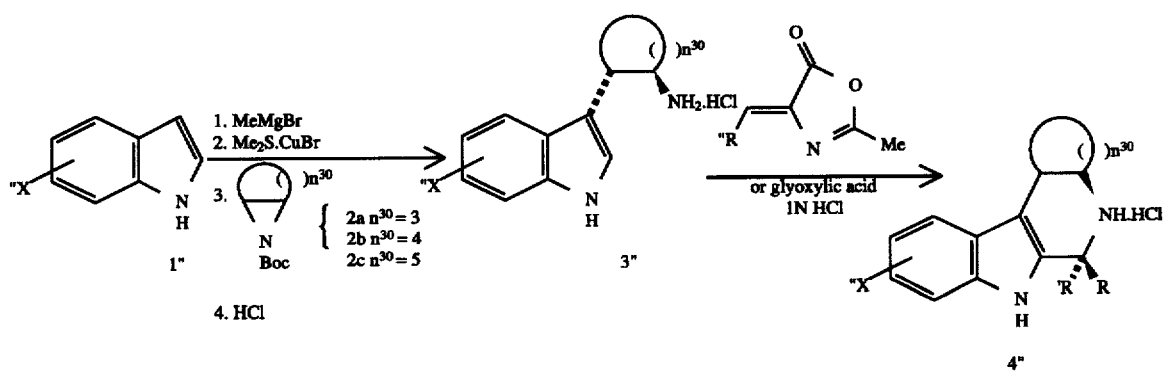

| | | | | | |
|---|---|---|---|---|---|
| a X" = 5-Me | a X" = 5-Me | n³⁰ = 3 (90) | a X" = 5-Me | n³⁰ = 4 | R, R' = H (95) |
| b X" = 7-Cl | b X" = 7-Cl | n³⁰ = 3 (91) | b X" = 7-Cl | n³⁰ = 4 | R, R' = H (96) |
| c X" = 5,7-diMe | c X" = 5,7-Me₂ | n³⁰ = 3 | c X" = 5-Me | n³⁰ = 3 | R = 3,4-(OMe)₂Bn, R' = H (97) |
| | d X" = 5-Me | n³⁰ = 4 (92) | d X" = 7-Cl | n³⁰ = 3 | R = 3,4-(OMe)₂Bn, R' = H (98) |
| | e X" = 7-Cl | n³⁰ = 4 (93) | e X" = 5,7-Me₂ | n³⁰ = 3 | R = 3,4-(OMe)₂Bn, R' = H (99) |
| | f X" = 5,7-Me₂ | n³⁰ = 4 (94) | f X" = 5-Me | n³⁰ = 4 | R = 3,4-(OMe)₂Bn, R' = H (100) |
| | g X" = 5-Me | n³⁰ = 5 | g X" = 7-Cl | n³⁰ = 4 | R = 3,4-(OMe)₂Bn, R' = H (101) |
| | | | h X" = 5,7-Me₂ | n³⁰ = 4 | R = 3,4-(OMe)₂Bn, R' = H (102) |
| | | | i X" = 5-Me | n³⁰ = 5 | R = 3,4-(OMe)₂Bn, R' = H (103) |
| | | | j X" = 5-Me | n³⁰ = 3 | R = 1-naphthylmethyl, R' = H (104) |
| | | | k X" = 5-Me | n³⁰ = 4 | R = 1-naphthylmethyl, R' = H (105) |
| | | | l X" = 5,7-Me₂ | n³⁰ = 4 | R = 1-naphthylmethyl, R' = H (106) |
| | | | m X" = 5-Me | n³⁰ = 4 | R, R' = H (107) |

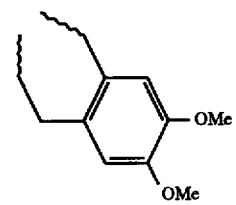

For Examples 90 through 109, where applicable, diethyl ether was distilled from sodium benzophenone ketyl prior to use. All reactions were performed under a positive pressure of argon. ¹H-NMR and ¹³C-NMR data were recorded on a Bruker AC-200P (200 MHz). IR spectra were obtained on Nicolet 510 P-FT (film and KBr). Melting points were determined on a Büchi apparatus and are not corrected. Analytical TLC was performed on Merck TLC glass plates precoated with $F_{254}$ silica gel 60 (UV, 254 nm and Iodine). Chromatographic separations were performed by using 230–400 mesh silica gel (Merck). N-BOC-aziridines (2a–d) were prepared from the corresponding alkenes following standard procedures.

Preparation 1

Preparation of 4-chlorobutanal

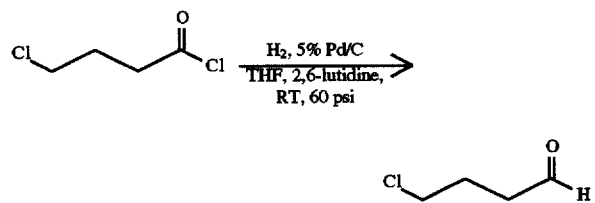

4-Chlorobutyryl chloride (300 g, 2.13 mol.) was dissolved in dry THF (3 L). To this solution was added 2,6-lutidine (252 mL) followed by 5% Pd/C (30 g). This mixture was placed in a Parr hydrogenator and shaken under 60 psi of hydrogen for 6 hours. The mixture was purged with nitrogen, filtered, washing the catalyst with THF (500 mL), and concentrated at room temperature under reduced pressure. Distillation afforded 4-chlorobutanal (148.3 g) as a colorless liquid.

EXAMPLE 1

Preparation of 8-methyl-1-[(3,4-dimethoxyphenyl) methyl]-1,2,3,4-tetrahydro-9H-pyrido[3,4-b]indole

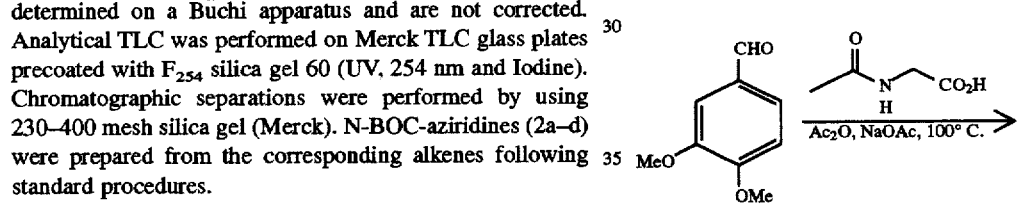

A solution of 3,4-dimethoxybenzaldehyde (24.5 g, 0.15 mol.), N-acetylglycine (17.4 g, 0.15 mol.) and sodium acetate (12.1 g, 0.15 mol) in acetic anhydride (135 mL) was heated to 100° C. for 12 hours. The reaction mixture was cooled to ambient temperature poured onto ice (300 mL) with stirring. The product was isolated by filtration, washed with water (3×50 mL) and diethyl ether (3×50 mL) and dried under reduced pressure (16.3 g).

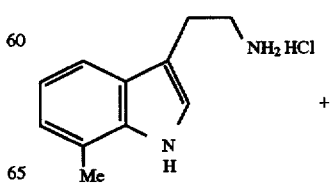

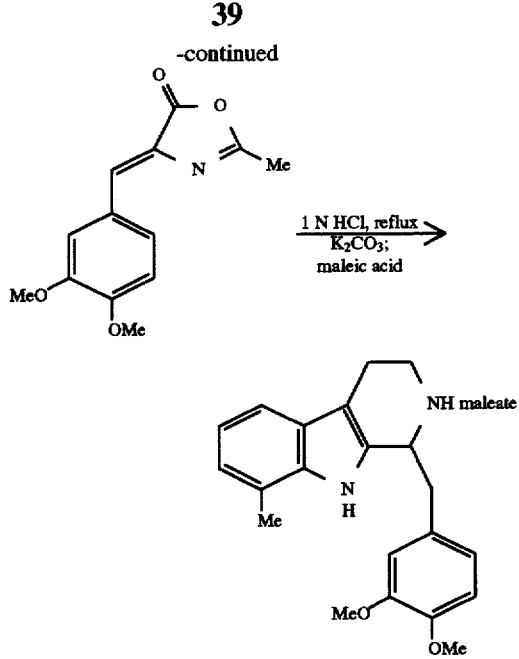

A suspension of azalactone prepared above (1.35 g, 5.46 mmol.) and 7-methyl-tryptamine hydrochloride (1.15 g, 5.46 mmol.) in 1N HCl (50 mL) was heated to reflux for 24 hours under nitrogen atmosphere. The reaction mixture was cooled to ambient temperature neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (730 mg) by filtration. (mp=168° C., dec.)

| Analysis | Calculated | Found |
|---|---|---|
| C | 66.36 | 66.15 |
| H | 6.24 | 6.28 |
| N | 6.19 | 5.79 |

EXAMPLE 2

Preparation of 8-bromo-1-[(3,4-dimethoxyphenyl)methyl]-1,2,3,4-tetrahydro-9H-pyrido[3,4-b]indole hydrochloride To a stirred suspension of 2-bromophenyl-hydrazine hydrochloride (25.8 g, 115 mmol.) in chloroform (500 mL) was added saturated sodium carbonate solution (500 mL). The mixture was stirred for 30 minutes and extracted with chloroform (2×200 mL). The combined organic phases were concentrated to afford the hydrazine free base as a yellow oil. This oil was dissolved in methanol (100 mL) and treated slowly with 4-chlorobutanal (12.3 g, 115 mmol). The mixture was placed in a sealable tube and purged with nitrogen for 10 minutes. The tube was sealed and placed in an oil bath preheated to 95° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromotryptamine hydrochloride (3.6 g) as a pale solid, which was used without further purification.

A suspension of azalactone (prepared as described in Example 1) (1.16 g, 4.7 mmol.) and 7-bromotryptamine hydrochloride (1.0 g, 3.6 mmol.) in 1N HCl (100 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 860 mg of desired product as the hydrochloride salt. (mp=279°–281° C., dec.)

| Analysis | Calculated | Found |
|---|---|---|
| C | 54.87 | 54.75 |
| H | 5.07 | 5.20 |
| N | 6.40 | 6.23 |

EXAMPLE 3

Preparation of 6,8-dibromo-1-[(3,4-dimethoxyphenyl)methyl]-1,2,3,4-tetrahydro-9H-pyrido[3,4-b]indole To a stirred, cooled (−5° C.) solution of 2,4-dibromoaniline (50.0 g, 0.2 mol.) in concentrated HCl solution (110 mL) was added sodium nitrite (13.8 g, 0.2 mol.) in water (110 mL) dropwise at such a rate as to maintain temperature below 5° C. After complete addition, the mixture was further stirred at 5° C. for 30 minutes. A solution of tin chloride monohydrate (135.4 g, 0.6 mol.) in concentrated HCl (total volume 170 mL) was added dropwise again maintaining temperature below 5° C. After complete addition and 30 minutes of further stirring, the mixture was placed in the freezer overnight. The light brown solid which precipitated was isolated by filtration and washed with cold brine followed by a solution of petroleum ether/diethyl ether (2/1 by volume). This solid was slowly added to an ice cooled mixture of 50% sodium hydroxide solution/ethyl acetate. The mixture was extracted with ethyl acetate and the organic phase dried over magnesium sulfate. After filtration, the solution was concentrated to 400 mL total volume, diluted with diethyl ether (1.5 L) and treated with dry HCl. The product, 2,4-dibromophenyl-hydrazine hydrochloride (45.9 g) was isolated as a white solid and used without further purification.

To a stirred suspension of 2,4-dibromophenylhydrazine hydrochloride (22.0 g, 83 mmol.) in chloroform (500 mL) was added saturated potassium carbonate solution (500 mL). The mixture was stirred for 30 minutes and extracted with chloroform (2×200 mL). The combined organic phases were concentrated to afford the hydrazine free base as a yellow oil. This oil was dissolved in methanol (163 mL) and treated slowly with 4-chlorobutanal (8.8 g, 83 mmol.). The mixture was placed in a sealable tube and purged with nitrogen for 10 minutes. The tube was sealed and placed in an oil bath preheated to 95° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromotryptamine hydrochloride (1.5 g) as a pale solid, which was used without further purification.

A suspension of azalactone (prepared as described in Example 1) (0.45 g, 1.82 mmol.) and 5,7-dibromotryptamine hydrochloride (0.58 g, 1.64 mmol.) in 1N HCl (65 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (340 mg) by filtration. (mp=177°–179° C., dec.)

| Analysis | Calculated | Found |
|---|---|---|
| C | 48.34 | 48.61 |
| H | 4.06 | 4.17 |
| N | 4.70 | 4.69 |

EXAMPLE 4

Preparation of 6-methyl-8-bromo-1-[(3,4-dimethoxyphenyl)- methyl]-1,2,3,4-tetrahydro-9H-pyrido[3,4-b]indole hydrochloride To a stirred, cooled (−5° C.) solution of 2-bromo-4-methylaniline (50.54 g, 0.272 mol.) in concentrated HCl solution (200 mL) was added sodium nitrite (18.9 g, 0.274 mol.) in water (200 mL) dropwise at such a rate as to maintain temperature below 5° C. After complete addition, the mixture was further stirred at 5° C. for 30 minutes. A solution of tin chloride monohydrate (185.4 g, 0.822 mol.) in concentrated HCl (total volume 400 mL) was added dropwise again maintaining temperature below 5° C. After complete addition and 30 minutes of further stirring, the mixture was placed in the freezer overnight. The light brown solid which precipitated was isolated by filtration and washed with cold brine followed by a solution of petroleum ether/diethyl ether (2/1 by volume). This solid was slowly added to an ice cooled mixture of 50% sodium hydroxide solution/ethyl acetate. The mixture was extracted with ethyl acetate and the organic phase dried over magnesium sulfate. After filtration, the solution was concentrated to 400 mL total volume, diluted with diethyl ether (1.5 L) and treated with dry HCl. The product, 2-bromo-4-methylphenylhydrazine hydrochloride (52.4 g) was isolated as a light brown solid and used without further purification.

5-Methyl-7-bromotryptamine hydrochloride (4.95 g) was prepared as described in Example 3, except using 2-bromo-4-methylphenyl hydrazinc hydrochloride (21 g) as starting material.

A suspension of azalactone (prepared as described in Example 5) (1.44 g, 6.07 mmol.) and 5-methyl-7-bromotryptamine hydrochloride (1.12 g, 3.87 mmol.) in 1N HCl (80 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 1.06 g of desired product as a pale solid. (mp=251°–253° C., dec.)

| Analysis | Calculated | Found |
|---|---|---|
| C | 55.83 | 56.08 |
| H | 5.35 | 5.32 |
| N | 6.20 | 6.33 |

EXAMPLE 5

Preparation of 8-methoxy-1-[(3,4-dimethoxyphenyl) methyl]-1,2,3,4-tetrahydro-9H-pyrido[3,4-b]indole To a stirred, cooled (0° C.) suspension of 2-methoxyphenylhydrazine hydrochloride (14.44 g, 83 mmol.) in THF (600 mL) was added 4-chlorobutanal (9.0 g, 84 mmol.) followed by dropwise addition of triethylamine (8.6 g, 85 mmol.) in THF (20 mL) Upon complete addition, the cooling bath was removed and the solution stirred for 1 hour. The reaction mixture was filtered and the filter cake washed with THF (100 mL). The combined filtrates were concentrated to an orange oil, which was dissolved in methanol (150 mL) and water (5 mL). The solution was transferred to a sealable tube and purged with nitrogen for 10 minutes. The tube was sealed and placed in an oilbath preheated to 95° C. After heating for 14 hours, the reaction mixture was cooled to ambient temperature and concentrated under reduced pressure. The residue was partitioned between saturated aqueous potassium carbonate and 3:1 chloroform:2-propanol. The organic phase was dried over sodium sulfate and concentrated. The residue was purified by flash chromatography on silica gel (15% methanol, 0.2% NH$_4$OH, in chloroform as eluent). The fractions containing product were pooled and concentrated under reduced pressure. The residue was dissolved in methanol and treated with dry HCl and concentrated to afford 7-methoxytryptamine hydrochloride (4.04 g) as a stable foam, which was used without further purification.

A suspension of azalactone (prepared as described in Example 1) (1.20 g, 4.85 mmol.) and 7-methoxytryptamine hydrochloride (1.0 g, 4.4 mmol.) in 1N HCl (120 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (770 mg) by filtration. (mp=219°–220° C., dec.).

| Analysis | Calculated | Found |
|---|---|---|
| C | 64.09 | 64.04 |
| H | 6.02 | 6.18 |
| N | 5.98 | 5.93 |

EXAMPLE 6

Preparation of 6,8-difluoro-1-[(3,4-dimethoxyphenyl)-methyl]-1,2,3,4-tetrahydro-9H-pyrido[3,4-b]indole

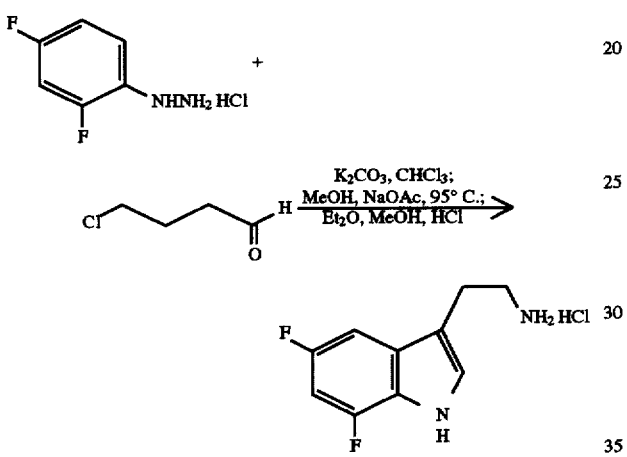

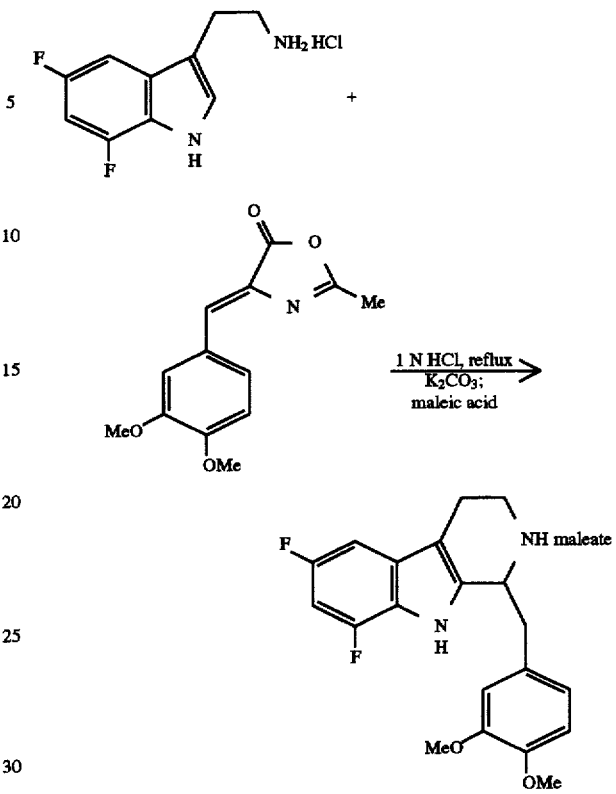

To a stirred suspension of 2,4-difluorophenylhydrazine hydrochloride (18.5 g, 128 mmol.) in chloroform (500 mL) was added saturated potassium carbonate solution (500 mL). The mixture was stirred for 30 minutes and extracted with chloroform (2×200 mL). The combined organic phases were concentrated to afford the hydrazine free base as a yellow oil. This oil was dissolved in a solution of methanol (163 mL), water (36 mL) and sodium acetate (10.57 g) and treated slowly with 4-chlorobutanal (13.7 g, 128 mmol.). The mixture was placed in a sealable tube and purged with nitrogen for 10 minutes. The tube was sealed and placed in an oil bath preheated to 95° C. Heating was continued for 15 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromotryptamine hydrochloride (6.3 g) as a pale solid, which was used without further purification.

A suspension of azalactone (prepared as described in Example 1) (1.07 g, 4.33 mmol.) and 5,7-difluorotryptamine hydrochloride (1.0 g, 4.3 mmol.) in 1N HCl (70 mL) was heated to reflux for 65 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with maleic acid. The product was isolated as the maleate salt (450 mg) by filtration. (mp=164°–166° C., dec.)

| Analysis | Calculated | Found |
|---|---|---|
| C | 60.76 | 60.63 |
| H | 5.10 | 5.14 |
| N | 5.90 | 5.82 |

EXAMPLE 7

Preparation of 7-methyl-8-bromo-1-[(3,4-dimethoxyphenyl)methyl]-1,2,3,4-tetrahydro-9H-pyrido[3,4-b]indole hydrochloride 2-Bromo-3-methylphenylhydrazine hydrochloride (23 g) was prepared as described for 2-bromo-4-methylphenylhydrazine hydrochloride in Example 4, except using 2-bromo-3-methylaniline as starting material.

6-Methyl-7-bromotryptamine hydrochloride was prepared (2.42 g) as described for 5-methyl-7-bromotryptamine hydrochloride in Example 4, except using 2-bromo-3-methylphenylhydrazine hydrochloride as starting material.

A suspension of azalactone (prepared as described in Example 1) (3.63 g, 14.7 mmol.) and 6-methyl-7-bromotryptamine hydrochloride (4.25 g, 4.21 mmol.) in 1N HCl (150 mL) was heated to reflux for 18 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with dry HCl. The product was isolated as the hydrochloride salt (3.11 g) by filtration. m/e=414.

| Analysis | Calculated | Found |
|---|---|---|
| C | 55.83 | 56.13 |
| H | 5.18 | 5.29 |
| N | 6.20 | 6.31 |

EXAMPLE 8

Preparation of 6-(1,1-dimethylethyl)-1-[(3,4-dimethoxyphenyl)methyl]1,2,3,4-tetrahydro-1-9H-pyrido-[3,4b]indole hydrochloride 5-(1,1-dimethylethyl)-tryptamine hydrochloride was prepared (2.95 g) as described for 5-methyl-7-bromotryptamine hydrochloride in Example 4, except using 4-(1,1-dimethylethyl)-phenylhydrazine hydrochloride (6.00 g) as starting material.

A suspension of azalactone (prepared as described in Example 1) (1.25 g, 5.26 mmol.) and 5-(1,1-dimethylethyl)-tryptamine hydrochloride (1.33 g, 5.26 mmol.) in 1N HCl (50 mL) was heated to reflux for 24 hours under nitrogen atmosphere. The reaction mixture was cooled to ambient temperature, and the crude product isolated by filtration. The brown solid was triturated with isopropyl alcohol (3×50 mL) and washed with diethyl ether (3×50 mL). Recrystallization from ethanol afforded 0.74 g of desired product as a pale solid.

| Analysis | Calculated | Found |
|---|---|---|
| C | 69.47 | 69.66 |
| H | 7.53 | 7.50 |
| N | 6.75 | 6.71 |

EXAMPLE 9

Preparation of 5-fluoro-6-methyl-1-[(3,4-dimethoxyphenyl)methyl]-1,2,3,4-tetrahydro-9H-pyrido[3,4-b]indole 3-Fluoro-4-methylphenylhydrazine hydrochloride (21.4 g) was prepared as described for 2-bromo-4 methylphenylhydrazine hydrochloride in Example 4, except using 3-fluoro-4-methylaniline as starting material.

4-Fluoro-5-methyltryptamine hydrochloride was prepared (2.20 g) as described for 5-methyl-7-bromotryptamine hydrochloride in Example 4, except using 3-fluoro-4-methylphenylhydrazine hydrochloride (6.00 g) as starting material.

A suspension of azalactone (prepared as described in Example 1) (0.76 g, 3.06 mmol.) and 4-fluoro-5-methyltryptamine hydrochloride (0.70 g, 3.06 mmol.) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (60 mg) by filtration. mp. 191°–194° C.

| Analysis | Calculated | Found |
|---|---|---|
| C | 63.82 | 63.60 |
| H | 5.78 | 5.65 |
| N | 5.95 | 5.92 |

EXAMPLE 10

Preparation of 7,8,9,10-tetrahydro-10-[(3,4-dimethoxyphenyl)methyl]-11H-benzo[g]pyrido[3,4-b]indole 6,7-Benzotryptamine hydrochloride was prepared (2.85 g) as described for 5-methyl-7-bromotryptamine hydrochloride in Example 4, except using 1-naphthyl-hydrazine hydrochloride (6.00 g) as starting material.

A suspension of azalactone (prepared as described in Example 1) (1.51 g, 6.11 mmol.) and 6,7-benzotryptamine hydrochloride (1.50 g, 6.11 mmol.) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (240 mg) by filtration. m/e=373, mp. 187° C. (dec.)

| Analysis | Calculated | Found |
|---|---|---|
| C | 68.84 | 68.63 |
| H | 5.78 | 5.91 |
| N | 5.73 | 5.67 |

EXAMPLE 11

Preparation of 6-cyclohexyl-1-[(3,4-dimethoxyphenyl)-methyl]-1,2,3,4-tetrahydro-9H-pyrido[3,4-b]indole hydrochloride 4-Cyclohexylphenylhydrazine hydrochloride (35.6 g) was prepared as described for 2-bromo-4-methylphenylhydrazine hydrochloride in Example 4, except using 4-cyclohexylaniline as starting material.

5-Cyclohexyltryptamine hydrochloride was prepared (1.29 g) as described for 5-methyl-7-bromotryptamine hydrochloride in Example 4, except using 4-cyclohexylphenylhydrazine hydrochloride as starting material.

A suspension of azalactone (prepared as described in Example 1) (0.54 g, 2.18 mmol.) and 5-cyclohexyltryptamine hydrochloride (0.6 g, 2.18 mmol.) in 1N HCl (30 mL) was heated to reflux for 14 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (140 mg) by filtration. m/e=404.

| Analysis | Calculated | Found |
|---|---|---|
| C | 69.21 | 69.17 |
| H | 6.97 | 7.01 |
| N | 5.38 | 5.53 |

EXAMPLE 12

Preparation of 5,8-dimethyl-1,2,3,4-tetrahydro-1-[(3,4-dimethoxyphenyl)methyl]-9H-pyrido[3,4b]indole hydrochloride 4,7-dimethyltryptamine hydrochloride was prepared (0.94 g) as described for 5-methyl-7-bromotryptamine hydrochloride in Example 4, except using 2,5-dimethylphenylhydrazine hydrochloride (16.8 g) as starting material.

A suspension of azalactone (prepared as described in Example 1) (1.04 g, 4.21 mmol.) and 4,7-dimethyltryptamine hydrochloride (0.94 g, 4.21 mmol.) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with anhydrous HCl. The product was isolated as the hydrochloride salt (370 mg) by filtration. m/e=349

| Analysis | Calculated | Found |
|---|---|---|
| C | 68.29 | 68.59 |
| H | 7.03 | 6.92 |
| N | 7.24 | 7.04 |

EXAMPLE 13

Preparation of 6-(1-methylethyl)-1,2,3,4-tetrahydro-1-[(3,4-dimethoxyphenyl)methyl]-9H-pyrido[3,4b]indole To a stirred suspension of 4-isopropylphenylhydrazine hydrochloride monohydrate (15.3 g, 91.95 mmol.) in chloroform (250 mL) was added saturated sodium carbonate solution (250 mL). The mixture was stirred for 30 minutes and extracted with chloroform (2×200 mL). The combined organic phases were concentrated to afford the hydrazine free base as a yellow oil. This oil was dissolved in methanol (200 mL) and water (5 mL) and treated with sodium acetate (6.72 g, 82 mmol.) and 4-chlorobutanal (8.7 g, 82 mmol.). The mixture was placed in a sealable tube and purged with nitrogen for 10 minutes. The tube was sealed and placed in an oil bath preheated to 100° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 5-isopropyltryptamine hydrochloride (9.8 g) as a pale solid, which was used without further purification.

A suspension of azalactone (prepared as described in Example 1) (1.55 g, 6.31 mmol.) and 5-isopropyltryptamine hydrochloride (1.76 g, 7.37 mmol.) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (310 mg) by filtration. m/e=365, mp. 196°–200° C.

| Analysis | Calculated | Found |
|---|---|---|
| C | 67.48 | 67.74 |
| H | 6.71 | 6.75 |
| N | 5.83 | 5.92 |

EXAMPLE 14

Preparation of 6,8-dimethyl-1,2,3,4-tetrahydro-1-[(3,4-dimethoxyphenyl)methyl]-9H-pyrido[3,4b]indole hydrochloride 5,7-Dimethyltryptamine hydrochloride was prepared (2.86 g) as described for 5-methyl-7-bromotryptamine hydrochloride in Example 4, except using 2,4-dimethylphenylhydrazine hydrochloride (15.0 g) as starting material.

A suspension of azalactone (prepared as described in Example 1) (1.65 g, 6.67 mmol.) and 5,7-dimethyltryptamine hydrochloride (1.50 g, 6.67 mmol.) in 1N HCl (70 mL) was heated to reflux for 24 hours under nitrogen atmosphere. The reaction mixture was cooled to ambient temperature and the crude product isolated by filtration. The solid was triturated with ethanol/hexanes (3×50 mL) and washed with hexanes (3×50 mL). The product was isolated by filtration (820 mg). m/e=350.

| Analysis | Calculated | Found |
|---|---|---|
| C | 68.29 | 68.07 |
| H | 7.03 | 7.12 |
| N | 7.24 | 7.23 |

EXAMPLE 15

Preparation of 5,7-dimethyl-1,2,3,4-tetrahydro-1-[(3,4-dimethoxyphenyl)methyl]-9H-pyrido[3,4b]indole hydrochloride 4,6-Dimethyltryptamine hydrochloride was prepared (1.06 g) as described for 5-methyl-7-bromotryptamine hydrochloride in Example 4, except using 3,5-dimethylphenylhydrazine hydrochloride (7.65 g) as starting material.

A suspension of azalactone (prepared as described in Example 1) (1.16 g, 4.69 mmol.) and 4,6-dimethyltryptamine hydrochloride (1.05 g, 4.67 mmol.) in 1N HCl (60 mL) was heated to reflux for 24 hours under nitrogen atmosphere. The reaction mixture was cooled to ambient temperature and the crude product isolated by filtration. The solid was triturated with ethanol/hexanes (3×50 mL) and washed with hexanes (3×50 mL). The product was isolated by filtration (770 mg). m/e=350.

| Analysis | Calculated | Found |
|---|---|---|
| C | 68.29 | 68.09 |
| H | 7.03 | 7.12 |
| N | 7.24 | 7.02 |

EXAMPLE 16

Preparation of 6,7-dimethyl-1,2,3,4-tetrahydro-1-[(3,4-dimethoxyphenyl)methyl]-9H-pyrido[3,4b]indole To a stirred, cooled (0° C.) solution of 5,6-dimethylindole (3.69 g, 25.4 mmol.) in dry diethyl ether (75 mL) was added dropwise oxalyl chloride (3.8 mL, 43.0 mmol.) over 2 minutes. After further stirring for 30 minutes, the bright yellow acid chloride (5.99 g) was isolated by filtration and washed with dry diethyl ether. This acid chloride was added in portions to a rapidly stirred solution of aqueous (30%) ammonium hydroxide (100 mL). After the addition was complete, the mixture was further stirred at ambient temperature for 30 minutes and the crude product isolated by filtration. Recrystallization from THF/diethyl ether afforded product (3.05 g) as a tan solid.

To a stirred, refluxing solution of amide (prepared above) (3.05 g, 14.1 mmol.) in THF was added dropwise a suspension of lithium aluminum hydride (3.07 g, 81.3 mmol.) in THF over 1 H. Upon complete addition, the mixture was further heated to reflux for 14 H. The reaction mixture was cooled to 0° C. and carefully treated with water (3.1 mL) followed by 15% sodium hydroxide solution (3.1 mL), followed by water (9.3 mL). The salts were removed by filtration and the filtrate was concentrated under reduced pressure. The residue was dissolved in diethyl ether (80 mL) with 5% ethyl acetate and treated with anhydrous HCl. The hydrochloride salt (2.65 g) was isolated by filtration and washed with dry ether.

A suspension of azalactone (prepared as described in Example 1) (1.10 g, 4.45 mmol.) and 5,6-dimethyltryptamine hydrochloride (1.00 g, 4.45 mmol.) in 1N HCl (60 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (450 mg) by filtration. mp. 197°–200° C.

| Analysis | Calculated | Found |
|---|---|---|
| C | 66.94 | 67.01 |
| H | 6.48 | 6.56 |
| N | 6.00 | 5.98 |

EXAMPLE 17

Preparation of 6-ethyl-1,2,3,4-tetrahydro-1-[(3,4-dimethoxyphenyl)methyl]-9H-pyrido[3,4b]indole To a stirred, cooled (0° C.) solution of 5-ethylindole (4.0 g, 27.5 mmol.) in dry diethyl ether (250 mL) was added dropwise oxalyl chloride (4.8 mL, 55.1 mmol.) over 2 minutes. After further stirring for 30 minutes, the bright yellow acid chloride was isolated by filtration and washed with dry diethyl ether. This acid chloride was added in portions to a rapidly stirred solution of aqueous (30%) ammonium hydroxide (200 mL). After the addition was complete, the mixture was further stirred at ambient temperature for 30 minutes and the crude product isolated by filtration (4.7 g) as a tan solid.

To a stirred, refluxing solution of amide (prepared above) (4.7 g, 21.7 mmol.) in THF was added dropwise a suspension of lithium aluminum hydride (4.7 g, 121 mmol.) in THF over 1 H. Upon complete addition, the mixture was further heated to reflux for 14 H. The reaction mixture was cooled to 0° C. and carefully treated with water (4.7 mL) followed by 15% sodium hydroxide solution (4.7 mL), followed by water (14.1 mL). The salts were removed by filtration and the filtrate was concentrated under reduced pressure. The residue was dissolved in diethyl ether (80 mL) with 5% ethyl acetate and treated with anhydrous HCl. The hydrochloride salt (4.02 g) was isolated by filtration and washed with dry ether.

A suspension of azalactone (prepared as described in Example 1) (1.10 g, 4.45 mmol.) and 5,6-dimethyltryptamine hydrochloride (1.00 g, 4.45 mmol.) in 1N HCl (60 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (520 mg) by filtration. mp. 185° C. (dec.).

| Analysis | Calculated | Found |
|---|---|---|
| C | 66.94 | 66.95 |
| H | 6.48 | 6.55 |
| N | 6.01 | 5.99 |

EXAMPLE 18

Preparation of 6-bromo-1,2,3,4-tetrahydro-1-[(3,4-dimethoxyphenyl)methyl]-9H-pyrido[3,4b]indole A suspension of azalactone (prepared as described in Example 1) (0.91 g, 3.7 mmol.) and 5-bromotryptamine hydrochloride (1.01 g, 3.7 mmol.) in 1N HCl (60 mL) was heated to reflux for 18 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with maleic acid. The product was isolated as the maleate salt (800 mg) by filtration. (mp=184°–188° C., dec.) m/e=403.

| Analysis | Calculated | Found |
|---|---|---|
| C | 55.72 | 55.51 |
| H | 4.87 | 5.09 |
| N | 5.41 | 5.36 |

EXAMPLE 19

Preparation of 7,8-dimethyl-1,2,3,4-tetrahydro-1-[(3,4-dimethoxyphenyl)methyl]-9H-pyrido[3,4b]indole hydrochloride 6,7-Dimethyltryptamine hydrochloride was prepared (2.26 g) as described for 5-methyl-7-bromotryptamine hydrochloride in Example 4, except using 2,2-dimethylphenylhydrazine hydrochloride (15.0 g) as starting material.

A suspension of azalactone (prepared as described in Example 1) (1.39 g, 5.62 mmol.) and 6,7-dimethyltryptamine hydrochloride (1.26 g, 5.61 mmol.) in 1N HCl (70 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with anhydrous HCl. The product was isolated as the hydrochloride salt (290 mg) by filtration. m/e=350

| Analysis | Calculated | Found |
|---|---|---|
| C | 68.29 | 68.51 |
| H | 7.03 | 6.87 |
| N | 7.24 | 7.22 |

EXAMPLE 20

Preparation of 6-methyl-1,2,3,4-tetrahydro-1-[(3,4-dimethoxyphenyl)methyl]-9H-pyrido[3,4b]indole hydrochloride A suspension of azalactone (prepared as described in Example 1) (3.4 g, 12.4 mmol.) and 5-methyltryptamine hydrochloride (2.0 g, 9.9 mmol.) in 1N HCl (100 mL) was heated to reflux for 24 hours under nitrogen atmosphere. The reaction mixture was cooled to ambient temperature and the crude product isolated by filtration. The solid was triturated with ethanol and washed with diethyl ether. The product was isolated as the hydrochloride salt by filtration (3.2 g). mp. 245°–246° C. (dec.)

| Analysis | Calculated | Found |
|---|---|---|
| C | 67.64 | 67.42 |
| H | 6.67 | 6.66 |
| N | 7.51 | 7.25 |

EXAMPLE 21

Preparation of 6-methyl-1-[(3,4,5-trimethoxyphenyl)-methyl]-1,2,3,4-tetrahydro-9H-pyrido[3,4-b]indole hydrochloride A solution of 3,4,5-trimethoxybenzaldehyde (20.0 g, 0.10 mol.), N-acetylglycine (11.9 g, 0.10 mol.) and sodium acetate (8.4 g, 0.1 mol) in acetic anhydride (100 mL) was heated to 100° C. for 2 hours. The reaction mixture was cooled to ambient temperature poured onto ice (300 mL) with stirring. The product was isolated by filtration, washed with water (3×50 mL) and diethyl ether (3×50 mL) and dried under reduced pressure (5.6 g).

A suspension of azalactone (prepared above) (2.0 g, 7.2 mmol.) and 5-methyltryptamine hydrochloride (1.1 g, 5.4 mmol.) in 1N HCl (20 mL) was heated to reflux for 48 hours under nitrogen atmosphere. The reaction mixture was cooled to ambient temperature and the crude product isolated by filtration. The solid was triturated with isopropanol and washed with diethyl ether. The product was isolated by filtration (650 mg). mp. 228°–229° C.

| Analysis | Calculated | Found |
|---|---|---|
| C | 65.58 | 65.38 |
| H | 6.75 | 6.76 |
| N | 6.95 | 6.92 |

EXAMPLE 22

Preparation of 6-methyl-1-[(2,3,4-trimethoxyphenyl)-methyl]-1,2,3,4-tetrahydro-9H-pyrido[3,4-b]indole hydrochloride Azalactone (12.28 g) was prepared as in Example 21 except using 2,3,4-trimethoxybenzaldehyde (20.0 g).

A suspension of azalactone (prepared above) (2.0 g, 7.2 mmol.) and 5-methyltryptamine hydrochloride (1.1 g, 5.4 mmol.) in 1N HCl (20 mL) was heated to reflux for 48 hours under nitrogen atmosphere. The reaction mixture was cooled to ambient temperature and the crude product isolated by filtration. The solid was triturated with isopropanol and washed with diethyl ether. The product was isolated by filtration (1.36 g). mp. 214.5° C.

| Analysis | Calculated | Found |
|---|---|---|
| C | 65.58 | 65.41 |
| H | 6.75 | 6.70 |
| N | 6.95 | 6.89 |

EXAMPLE 23

Preparation of 6-methyl-1-[(2-methoxyphenyl)methyl]-1,2,3,4-tetrahydro-9H-pyrido[3,4-b]indole hydrochloride Azalactone (16.42 g) was prepared as in Example 21 except using 2-methoxybenzaldehyde (20.0 g).

A suspension of azalactone (prepared above) (2.0 g, 9.2 mmol.) and 5-methyltryptamine hydrochloride (1.5 g, 6.9 mmol.) in 1N HCl (20 mL) was heated to reflux for 48 hours under nitrogen atmosphere. The reaction mixture was cooled to ambient temperature and the crude product isolated by filtration. The solid was triturated with isopropanol and washed with diethyl ether. The product was isolated by filtration (880 mg). mp. 252.8° C.

| Analysis | Calculated | Found |
|---|---|---|
| C | 70.06 | 70.15 |
| H | 6.76 | 6.83 |
| N | 8.17 | 8.16 |

EXAMPLE 24

Preparation of 6-methyl-1-[(2,4-dimethoxyphenyl)methyl]-1,2,3,4-tetrahydro-9H-pyrido[3,4-b]indole hydrochloride Azalactone (7.55 g) was prepared as in Example 21 except using 2,4-dimethoxybenzaldehyde (20.0 g).

A suspension of azalactone (prepared above) (2.0 g, 8.1 mmol.) and 5-methyltryptamine hydrochloride (1.3 g, 6.1 mmol.) in 1N HCl (20 mL) was heated to reflux for 48 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with anhydrous HCl. The product was isolated as the hydrochloride salt (361 mg) by filtration. mp. 262.6° C.

| Analysis | Calculated | Found |
|---|---|---|
| C | 67.64 | 67.73 |
| H | 6.76 | 6.85 |
| N | 7.51 | 7.50 |

EXAMPLE 25

Preparation of 6-methyl-1-[(2,5-dimethoxyphenyl)methyl]-1,2,3,4-tetrahydro-9H-pyrido[3,4-b]indole hydrochloride Azalactone (13.21 g) was prepared as in Example 21 except using 2,5-dimethoxybenzaldehyde (20.0 g).

A suspension of azalactone (prepared above) (2.0 g, 8.1 mmol.) and 5-methyltryptamine hydrochloride (1.3 g, 6.1 mmol.) in 1N HCl (20 mL) was heated to reflux for 48 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with anhydrous HCl. The product was isolated as the hydrochloride salt (1.14 g) by filtration. mp. 262° C.

| Analysis | Calculated | Found |
|---|---|---|
| C | 67.64 | 67.36 |
| H | 6.76 | 6.71 |
| N | 7.51 | 7.25 |

EXAMPLE 26

Preparation of 6-methyl-1-[(2,4,5-trimethoxyphenyl)-methyl]-1,2,3,4-tetrahydro-9H-pyrido[3,4-b]indole hydrochloride Azalactone (8.36 g) was prepared as in Example 21 except using 2,4,5-trimethoxybenzaldehyde (20.0 g).

A suspension of azalactone (prepared above) (2.0 g, 7.2 mmol.) and 5-methyltryptamine hydrochloride (1.1 g, 5.4 mmol.) in 1N HCl (20 mL) was heated to reflux for 48 hours under nitrogen atmosphere. The reaction mixture was cooled to ambient temperature and the crude product isolated by filtration. The solid was triturated with isopropanol and washed with diethyl ether. The product was isolated by filtration. Recrystallization from ethanol/cyclohexane afforded product (299 mg). mp. 176.3° C.

| Analysis | Calculated | Found |
|---|---|---|
| C | 65.58 | 65.51 |
| H | 6.75 | 6.73 |
| N | 6.95 | 6.87 |

EXAMPLE 27

Preparation of 6-(1-methylethyl)-1-[(2,3,4-trimethoxyphenyl)methyl]-1,2,3,4-tetrahydro-9H-pyrido[3,4-b]indole hydrochloride A suspension of azalactone (prepared as in Example 22) (1.0 g, 3.61 mmol.) and 5-isopropyltryptamine hydrochloride (prepared as in Example 13) (646 mg, 2.7 mmol.) in 1N HCl (20 mL) was heated to reflux for 48 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with anhydrous HCl. The product was isolated as the hydrochloride salt (315 mg) by filtration. mp. 147.3° C.

| Analysis | Calculated | Found |
|---|---|---|
| C | 66.89 | 66.80 |
| H | 7.25 | 7.01 |
| N | 6.50 | 6.39 |

EXAMPLE 28

Preparation of 6-methyl-1-[(3,4-dimethoxy-5-nitrophenyl)methyl]-1,2,3,4-tetrahydro-9H-pyrido[3,4-b]indole hydrochloride Azalactone (16.9 g) was prepared as in Example 21 except using 3,4-dimethoxy-5-nitrobenzaldehyde (23.5 g).

A suspension of azalactone (prepared above) (2.8 g, 9.6 mmol.) and 5-methyltryptamine hydrochloride (2.0 g, 9.5 mmol.) in 1N HCl (50 mL) was heated to reflux for 72 hours under nitrogen atmosphere. The reaction mixture was cooled to ambient temperature and the crude product isolated by filtration. The solid was triturated with isopropanol and washed with diethyl ether. The product was isolated as the hydrochloride salt by filtration (3.44) mp. 239°–243° C., m/e=381.

| Analysis | Calculated | Found |
|---|---|---|
| C | 60.36 | 60.54 |
| H | 5.79 | 5.66 |
| N | 10.06 | 10.12 |

EXAMPLE 29

Preparation of 6-methyl-1-[(3-iodo-4,5-dimethoxyphenyl)methyl]-1,2,3,4-tetrahydro-9H-pyrido[3,4-b]indole To a stirred, cooled (0° C.) solution of iodovanillin (10.0 g, 35.96 mmol.) in dimethylformamide (50 mL) was added anhydrous potassium carbonate (20.0 g, 143.86 mmol.) followed by iodomethane (3.11 mL, 50.0 mmol.). The mixture was allowed to warm to ambient temperature and stir for 14 H. The mixture was poured into diethyl ether (500 mL) and washed with water (3×150 mL). The organic phase was dried over MgSO$_4$ and concentrated under reduced pressure to afford 3-iodo-4,5-dimethoxybenzaldehyde (9.5 g) as a yellow oil which solidified upon standing and was used without further purification.

Azalactone (11.1 g) was prepared as in Example 21 except using 3-iodo-4,5-dimethoxybenzaldehyde (9.5 g), and hippuric acid (6.41 g) instead of N-acetylglycine.

A suspension of azalactone (prepared above) (2.2 g, 5.0 mmol.) and 5-methyltryptamine hydrochloride (1.0 g, 4.3 mmol.) in 1N HCl (100 mL) was heated to reflux for 48 hours under nitrogen atmosphere. The reaction mixture was cooled to ambient temperature, neutralized with saturated aqueous sodium hydroxide solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (134 mg) by filtration. m/e=463.

| Analysis | Calculated | Found |
|---|---|---|
| C | 51.92 | 52.15 |
| H | 4.71 | 4.72 |
| N | 4.84 | 4.70 |

EXAMPLE 30

Preparation of 6-methyl-1-[(3,4-dimethoxy-5-amino-phenyl)methyl]-1,2,3,4-tetrahydro-9H-pyrido[3,4-b]indole dihydrochloride To a stirred solution of nitro compound (prepared in Example 28) (3.0 g, 7.2 mmol.) in acetic acid (40 mL) was added activated zinc dust (4.64 g). The reaction mixture was stirred at ambient temperature for 2 H, diluted with water (200 mL) and filtered through celite. The filtrate was neutralized with aqueous ammonium hydroxide solution and extracted with chloroform. The organic phase was washed with brine and dried over magnesium sulfate. The combined organic phases were concentrated under reduced pressure and the residue dissolved in ethyl acetate and treated with anhydrous HCl. The product was isolated by filtration, washing with diethyl ether and trituration with ethyl acetate to afford product as the bis-hydrochloride salt (2.41 g). mp. 230°–234° C., m/e=351.

| Analysis | Calculated | Found |
|---|---|---|
| C | 59.44 | 58.47 |
| H | 6.41 | 6.31 |
| N | 9.90 | 9.68 |

EXAMPLE 31

Preparation of 6-methyl-1-[(3-methoxy-4-propoxyphenyl)methyl]-1,2,3,4-tetrahydro-9H-pyrido[3,4-b]indole To a stirred solution of vanillin (30.0 g, 197 mmol.) in methanol (100 mL) was added anhydrous potassium carbonate (13.7 g, 99 mmol.) followed by allyl bromide (17.0 mL, 197 mmol.). The mixture was heated to reflux for 5 H. The reaction mixture was filtered and concentrated under reduced pressure to afford the intermediate product (30.4 g) as an oily solid which was used without further purification.

Azalactone (32.2 g) was prepared as in Example 21 except using 3-methoxy-4-allyloxybenzaldehyde (30.4 g), and hippuric acid (28.3 g) instead of N-acetyl glycine.

A suspension of azalactone (prepared above) (1.74 g, 5.2 mmol.) and 5-methyltryptamine hydrochloride (1.1 g, 5.2 mmol.) in 1N HCl (40 mL) and ethanol (30 mL) was heated to reflux for 18 hours under nitrogen atmosphere. The reaction mixture was cooled to ambient temperature, neutralized with saturated aqueous potassium carbonate solution and extracted with chloroform. The combined organic phases were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (560 mg) by filtration. m/e=362. The product was used without further purification.

To a suspension of maleate salt (560 mg, 1.7 mmol.) in chloroform (100 mL) was added saturated potassium carbonate solution (100 mL) with vigorous stirring. The layers were separated and the aqueous phase was further extracted with chloroform (2×100 mL). The combined organic phases were dried over anhydrous sodium sulfate and concentrated under reduced pressure. The free base was dissolved in ethanol and hydrogenated (25° C., 60 PSI) in the presence of raney nickel catalyst. The catalyst was removed by filtration and the solution concentrated under reduced pressure to afford a viscous oil, which was dissolved in ethyl acetate and treated with maleic acid (140 mg). The crude product was isolated by filtration. Trituration with hot ethyl acetate and washing with diethyl ether afforded product (170 mg) as the maleate salt. mp. 188° C., m/e=365.

| Analysis | Calculated | Found |
|---|---|---|
| C | 67.48 | 67.62 |
| H | 6.71 | 6.66 |
| N | 5.83 | 5.80 |

EXAMPLE 32

Preparation of 6-methyl-1-[(4-dimethylaminophenyl)methyl]-1,2,3,4-tetrahydro-9H-pyrido[3,4-b]indole dihydrochloride To a stirred, cooled (−78° C.) suspension of methoxymethyltriphenylphosphonium chloride (13.79 g, 40.02 mmol.) in dry THF (150 mL) was added n-BuLi solution (25.2 mL. 1.6M, 40.02 mmol.) dropwise by syringe. The orange suspension was stirred at −78° C. for 15 min. A solution of 4-dimethylaminobenzaldehyde (5.00 g, 3.35 mmol.) in THF (75 mL) was added to the ylide dropwise over 10 min. The reaction mixture was gradually warmed to ambient temperature and stirred 14 H. Saturated ammonium chloride solution (100 mL) was added and the mixture extracted with diethyl ether (3×50 mL). The combined organic phases were dried over sodium sulfate and concentrated under reduced pressure. Chromatography on silica gel, eluting with 15% ethyl acetate/hexanes afforded product (4.70 g) as a mixture of olefin isomers which was used without further purification.

A mixture of 5-methyltryptamine hydrochloride (891 mg, 4.23 mmol.) and 1-methoxy-4'-dimethylaminostyrene (1.00 g, 5.64 mmol.) in acetonitrile (20 mL) and 1N HCl solution (150 mL) was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/ 0.2% NH₄OH as eluent). The fractions containing product were pooled and concentrated under reduced pressure. The residue was dissolved in ethyl acetate and treated with anhydrous HCl. The product was isolated as the dihydrochloride salt (354 mg) by filtration. mp. 275.4° C.

| Analysis | Calculated | Found |
|---|---|---|
| C | 64.28 | 64.21 |
| H | 6.94 | 7.01 |
| N | 10.71 | 10.74 |

EXAMPLE 33

Preparation of 6-methyl-1-[(4-dibutylaminophenyl)methyl]-1,2,3,4-tetrahydro-9H-pyrido[3,4-b]indole dihydrochloride To a stirred, cooled (−78° C.) suspension of methoxymethyl-triphenylphosphonium chloride (8.81 g, 25.7 mmol.) in dry THF (150 mL) was added n-BuLi solution (16.1 mL. 1.6M, 25.7 mmol.) dropwise by syringe. The orange suspension was stirred at −78° C. for 15 min. A solution of 4-dibutylaminobenzaldehyde (5.00 g, 2.14 mmol.) in THF (75 mL) was added to the ylide dropwise over 10 min. The reaction mixture was gradually warmed to ambient temperature and stirred 14 H. Saturated ammonium chloride solution (100 mL) was added and the mixture extracted with diethyl ether (3×50 mL). The combined organic phases were dried over sodium sulfate and concentrated under reduced pressure. Chromatography on silica gel, eluting with 15% ethyl acetate/hexanes afforded product (3.47 g) as a mixture of olefin isomers which was used without further purification.

A mixture of 5-methyltryptamine hydrochloride (605 mg, 2.87 mmol.) and 1-methoxy-4'-dibutylamino-styrene (1.00 g, 3.83 mmol.) in acetonitrile (20 mL) and 1N HCl solution (150 mL) was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/ 0.2% NH₄OH as eluent). The fractions containing product were pooled and concentrated under reduced pressure. The residue was dissolved in ethyl acetate and treated with anhydrous HCl. The product was isolated as the dihydrochloride salt (476 mg) by filtration. mp. 266.6° C.

| Analysis | Calculated | Found |
|---|---|---|
| C | 68.05 | 67.92 |
| H | 8.25 | 8.22 |
| N | 8.82 | 8.74 |

EXAMPLE 34

Preparation of 6-methyl-1-[(3-fluoro-4-methoxyphenyl)methyl]-1,2,3,4-tetrahydro-9H-pyrido[3,4-b]indole hydrochloride Azalactone (0.330 g) was prepared as in Example 21 except using 3-fluoro-4-methoxybenzaldehyde (5.0 g).

A suspension of azalactone prepared above (0.30 g, 1.3 mmol.) and 5-methyltryptamine hydrochloride (0.27 g, 1.3 mmol.) in 1N HCl (20 mL) was heated to reflux for 24 hours under nitrogen atmosphere. The reaction mixture was cooled to ambient temperature neutralized with saturated aqueous potassium carbonate solution and extracted with chloroform.

The combined organic phases were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with anhydrous HCl. The product was isolated as the hydrochloride salt (170 mg) by filtration. m/e=324.

| Analysis | Calculated | Found |
|---|---|---|
| C | 66.57 | 66.37 |
| H | 6.15 | 6.16 |
| N | 7.76 | 7.5 |

EXAMPLE 35

Preparation of 6-methyl-1-[(3,4-dimethylphenyl) methyl]-1,2,3,4-tetrahydro-9H-pyrido[3,4-b]indole hydrochloride Azalactone (11.3 g) was prepared as in Example 21 except using 3,4-dimethylbenzaldehyde (25.0 g).

A suspension of azalactone prepared above (2.04 g, 9.5 mmol.) and 5-methyl-tryptamine hydrochloride (2.0 g, 9.5 mmol.) in 1N HCl (80 mL) was heated to reflux for 24 hours under nitrogen atmosphere. The reaction mixture was cooled to ambient temperature and the crude product isolated by filtration. The solid was triturated with ethanol and washed with diethyl ether. The product was isolated as the hydrochloride salt by filtration (1.89 g). m/e=304.

| Analysis | Calculated | Found |
|---|---|---|
| C | 73.99 | 73.84 |
| H | 7.39 | 7.35 |
| N | 8.21 | 8.48 |

EXAMPLE 36

Preparation of 6-methyl-1-[(2-chloro-3,4-dimethoxyphenyl)methyl]-1,2,3,4-tetrahydro-9H-pyrido[3,4-b]indole hydrochloride Azalactone (5.26 g) was prepared as in Example 21 except using 2-chloro-3,4-dimethoxybenzaldehyde (10.45 g).

A suspension of azalactone prepared above (1.34 g, 4.76 mmol.) and 5-methyltryptamine hydrochloride (1.0 g, 4.75 mmol.) in 1N HCl (30 mL) was heated to reflux for 24 hours under nitrogen atmosphere. The reaction mixture was cooled to ambient temperature and the crude product isolated by filtration. The solid was triturated with ethanol and washed with diethyl ether. The product was isolated by filtration (1.19 g). m/e=370, mp. 244° C. (dec.).

| Analysis | Calculated | Found |
|---|---|---|
| C | 61.92 | 61.67 |
| H | 5.94 | 5.94 |
| N | 6.88 | 6.94 |

EXAMPLE 37

Preparation of 6-methyl-1-[(2-chloro-3-methoxy-4-hydroxyphenyl)methyl]-1,2,3,4-tetrahydro-9H-pyrido[3,4-b]-indole hydrochloride Azalactone (12.4 g) was prepared as in Example 21 except using 2-chloro-3-methoxy-4-hydroxybenzaldehyde (12.0 g).

A suspension of azalactone prepared above (1.29 g, 4.82 mmol.) and 5-methyl-tryptamine hydrochloride (1.0 g, 4.75 mmol.) in 1N HCl (30 mL) was heated to reflux for 24 hours under nitrogen atmosphere. The reaction mixture was cooled to ambient temperature and the crude product isolated by filtration. The solid was triturated with ethanol and washed with diethyl ether. The product was isolated by filtration (1.07 g). mp. 240° C. (dec.).

| Analysis | Calculated | Found |
|---|---|---|
| C | 61.07 | 60.83 |
| H | 5.64 | 5.71 |
| N | 7.12 | 7.03 |

EXAMPLE 38

Preparation of 5-fluoro-6-methyl-1-[(2-chloro-3,4-dimethoxyphenyl)methyl]-1,2,3,4-tetrahydro-9H-pyrido[3,4-b]indole hydrochloride A suspension of azalactone (prepared in Example 36) (2.15 g, 7.63 mmol.) and 4-fluoro-5-methyl-tryptamine hydrochloride (prepared in Example 9 (1.0 g, 4.75 mmol.) in 1N HCl (80 mL) was heated to reflux for 24 hours under nitrogen atmosphere. The reaction mixture was cooled to ambient temperature and the crude product isolated by filtration. The solid was triturated with ethanol and washed with diethyl ether. The product was isolated as the hydrochloride salt by filtration (1.39 g). m/e=388.

| Analysis | Calculated | Found |
|---|---|---|
| C | 59.30 | 59.58 |
| H | 5.45 | 5.47 |
| N | 6.59 | 6.71 |

EXAMPLE 39

Preparation of 6-methyl-1-(cyclohexylmethyl)-1,2,3,4-tetrahydro-9H-pyrido[3,4-b]indole hydrochloride A suspension of cyclohexylacetaldehyde (631 mg, 5.0 mmol.) and 5-methyltryptamine hydrochloride (1.0 g, 4.3 mmol.) in ethanol (20 mL) was heated to reflux for 36 hours under nitrogen atmosphere. The reaction mixture was cooled to ambient temperature and the crude product isolated by filtration. The solid was triturated with ethanol and washed with diethyl ether. The product was isolated by filtration (731 mg). m/e=282, mp 230° C.

| Analysis | Calculated | Found |
|---|---|---|
| C | 71.56 | 71.27 |
| H | 8.53 | 8.56 |
| N | 8.78 | 8.64 |

EXAMPLE 40

Preparation of (±)6-methyl-1-[(3,4-dimethoxyphenyl)-1-ethyl]-1,2,3,4-tetrahydro-9H-pyrido[3,4-b]indole (Z)-2-butenedioate To a stirred, cooled (−20° C.) suspension of methoxymethyltriphenylphosphonium chloride (118.9 g, 347 mmol.)

in dry THF (2000 mL) was added potassium t-butoxide (39.3 g, 350 mmol.) in portions. The orange suspension was stirred at −20° C. for 30 min. A solution of 3,4-dimethoxyacetophenone (50.0 g, 275 mmol.) in THF (500 mL) was added to the ylide dropwise over 30 min. The reaction mixture was gradually warmed to ambient temperature and stirred 2 H. Saturated ammonium chloride solution (500 mL) was added and the mixture extracted with diethyl ether (3×500 mL). The combined organic phases were dried over sodium sulfate and concentrated under reduced pressure. Chromatography on silica gel, eluting with 15% ethyl acetate/hexanes afforded product (48.4 g) as a mixture of olefin isomers which was used without further purification.

A mixture of 5-methyltryptamine hydrochloride (2.16 g, 10.3 mmol.) and 1-methoxy-2-methyl-3',4'-dimethoxystyrene (prepared above) (2.13 g, 10.3 mmol.) in methanol (12 mL) and 1N HCl solution (108 mL) was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH$_4$OH as eluent). The fractions containing product (upper diastereomer) were pooled and concentrated under reduced pressure. The residue was dissolved in ethyl acetate and treated with maleic acid. The product was isolated as the maleate salt (260 mg) by filtration. mp. 187°–190° C.

| Analysis | Calculated | Found |
|---|---|---|
| C | 66.94 | 66.95 |
| H | 6.48 | 6.35 |
| N | 6.00 | 5.81 |

EXAMPLE 41

Preparation of (±)6,7-dimethyl-1-[(3,4-dimethoxyphenyl)-1-ethyl]-1,2,3,4-tetrahydro-9H-pyrido[3,4-b]indole (Z)-2-butenedioate 5,6-dimethyltryptamine hydrochloride (prepared in Example 16) (1.60 g, 7.12 mmol.) was converted to its free base with aqueous potassium carbonate in chloroform. This solution was dried and treated with 1-methoxy-2-methyl-3', 4'-dimethoxystyrene (prepared above in Example 40) (1.49 g, 7.14 mmol.) and trifluororacetic acid (1.62 g, 14.2 mmol) and was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH$_4$OH as eluent). The fractions containing product (upper diastereomer) were pooled and concentrated under reduced pressure. The residue was dissolved in ethyl acetate and treated with maleic acid. The product was isolated as the maleate salt (560 mg) by filtration. m/e=364. mp. 177° C. (dec.).

| Analysis | Calculated | Found |
|---|---|---|
| C | 67.48 | 67.34 |
| H | 6.71 | 6.68 |
| N | 5.83 | 5.74 |

EXAMPLE 42

Preparation of (±)6-ethyl-1-[(3,4-dimethoxyphenyl)-1-ethyl]-1,2,3,4-tetrahydro-9H-pyrido[3,4-b]indole (Z)-2-butenedioate 5-ethyltryptamine hydrochloride (prepared in Example 17) (2.0 g, 8.9 mmol.) was converted to its free base with aqueous potassium carbonate in chloroform. This solution was dried and treated with 1-methoxy-2-methyl-3',4'-dimethoxystyrene (prepared above in Example 40) (1.86 g, 8.9 mmol.) and trifluroracetic acid (2.03 g, 17.8 mmol) and was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH$_4$OH as eluent). The fractions containing product (upper diastereomer) were pooled and concentrated under reduced pressure. The residue was dissolved in ethyl acetate and treated with maleic acid. The product was isolated as the maleate salt (430 mg) by filtration. m/e=364. mp. 192°–194° C. (dec.).

| Analysis | Calculated | Found |
|---|---|---|
| C | 67.48 | 67.32 |
| H | 6.71 | 6.72 |
| N | 5.83 | 5.76 |

EXAMPLE 43

Preparation of (±)6-methyl-1-[(3,4-dimethoxyphenyl)-1-propyl]-1,2,3,4-tetrahydro-9H-pyrido[3,4-b]indole (Z)-2-butenedioate To methanesulfonic acid (203 mL) was added phosphorus pentoxide (30.0 g) slowly with stirring. After the addition was complete, the mixture was further stirred under nitrogen atmosphere for 2 hours until homogenous. To this solution was added 3,4-dimethoxyphenylacetonitrile (50 g, 0.28 mol.) in a single portion, followed by 2-methyl-2,4-pentanediol (72.1 mL, 0.56 mol.) dropwise at such a rate as to maintain a temperature between 25° and 30° C. (1 hour). After complete addition, the reaction mixture was stirred at ambient temperature for 10 hours and poured onto ice (500 g). The mixture was made basic with sodium hydroxide solution (50%), added at such a rate as to keep the temperature below 35° C. The mixture was extracted with diethyl ether (3×250 mL) and the combined organic phases were dried over magnesium sulfate and concentrated under reduced pressure to afford a green solid. Distillation (Kugelrohr) afforded intermediate product (27.7 g) which was used without further purification.

To a stirred, cool (−78° C.) solution of previously prepared intermediate product (27.2 g, 0.106 mol.) in THF (400 mL) under argon atmosphere was added n-butyllithium solution (68.7 mL, 1.6M in hexanes, 0.11 mol.) dropwise via syringe over 15 minutes. After complete addition, the orange solution was stirred at −78° C. for 30 minutes. Ethyl bromide (8.18 mL, 0.10 mol.) was added dropwise via syringe and the resulting solution further stirred at −78° C. for 45 minutes. n-Butyllithium (68.7 mL, 1.6M in hexanes, 0.11 mol.) was added dropwise over 15 minutes and the orange solution stirred for 2 hours. The mixture was poured into ice/water (500 mL) and was acidified to pH 2–3 with 5N HCl solution. The mixture was extracted with diethyl ether (2×100 mL) and these extracts were discarded. The aqueous phase was made basic with sodium hydroxide solution (50%), cooling the mixture with ice when necessary. The basic aqueous phase was extracted with diethyl ether (2×200 mL) and the combined organic extracts were dried over magnesium sulfate, filtered and concentrated to afford product as an oily solid (12.08 g), which was used without further purification.

To a stirred cooled (−40° C.) solution of previous product (12.0 g, 39.3 mmol.) in THF (90 mL) and ethyl alcohol (90 mL) was added 5N HCl solution until pH 7. In a separate flask, a solution of sodium borohydride (2.12 g, 55.4 mmol.) was dissolved in water (20 mL) to which 1 drop of 50% sodium hydroxide had been added. Portions of the sodium borohydride solution and 5N HCl solution were alternately added to the reaction mixture such that the pH remained 6–8, at such a rate as to maintain temperature between −35° and −45° C. After complete addition, the reaction mixture was warmed to ambient temperature over about 2 hours. The reaction mixture was made basic with sodium hydroxide solution and extracted with diethyl ether (3×100 mL). The combined organic phases were washed with brine and dried over magnesium sulfate. Filtration and removal of solvent afforded crude product (11.3 g) as a viscous oil, which was used without further purification.

A mixture of crude product from the previous reaction (11.3 g, 36.8 mmol) and oxalic acid dihydrate (15.1 g, 120 mmol.) in water (300 mL) was heated to reflux for 12 hours. The mixture was cooled to ambient temperature and extracted with chloroform (2×100 mL). The combined organic phases were dried over magnesium sulfate, filtered and concentrated to afford aldehyde as an orange oil. Distillation (Kugelrohr) under reduced pressure afforded pure aldehyde (4.97 g) as a pale oil.

A mixture of 5-methyltryptamine hydrochloride (2.53 g, 12.0 mmol.) and 2-ethyl-3',4'-dimethoxyphenylacetaldehyde (prepared above) (2.49 g, 12.0 mmol.) in ethanol(30 mL) was heated to reflux for 48 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH$_4$OH as eluent). The fractions containing product (upper Rf diastereomer) were pooled and concentrated under reduced pressure. The residue was dissolved in ethyl acetate and treated with maleic acid. The product was isolated as the maleate salt (1.51 g) by filtration. m/e=364.

| Analysis | Calculated | Found |
|---|---|---|
| C | 67.48 | 67.35 |
| H | 6.71 | 6.96 |
| N | 5.83 | 5.77 |

EXAMPLE 44

Preparation of 2,6-dimethyl-1-[(2-chloro-3,4-dimethoxyphenyl)methyl]-1,2,3,4-tetrahydro-9H-pyrido[3,4-b]indole hydrochloride An aqueous solution of 6-methyl-1-[(2-chloro-3,4-dimethoxyphenyl)methyl]-1,2,3,4-tetrahydro-9H-pyrido[3,4-b]indole hydrochloride (Prepared in Example 36) (500 mg, 1.23 mmol.) was treated with sodium hydroxide (49 mg, 1.23 mmol.), followed by formic acid (0.91 mL) and aqueous formaldehyde solution (0.18 mL). The mixture was heated to reflux for 4 H. The reaction mixture was cooled to ambient temperature and concentrated under reduced pressure. The residue was partitioned between aqueous potassium carbonate solution and diethyl ether. The organic phase was dried over potassium carbonate and concentrated under reduced pressure. The residue was dissolved in ethyl acetate and treated with maleic acid. The maleate salt was isolated by filtration and purified by recrystallization from ethyl acetate/hexanes to afford product (240 mg). m/e=385.

| Analysis | Calculated | Found |
|---|---|---|
| C | 62.34 | 62.47 |
| H | 5.84 | 5.71 |
| N | 5.59 | 5.58 |

EXAMPLE 45

Preparation of 2-methyl-6-(1-methylethyl)-1,2,3,4-tetrahydro-1-[(3,4-dimethoxyphenyl)methyl]-9H-pyrido-[3,4b]indole maleate An aqueous solution of 6-(1-methylethyl)-1-[(3,4-dimethoxyphenyl)methyl]-1,2,3,4-tetrahydro-9H-pyrido[3,4-b]indole (Z)-2-butenedioate (prepared in Example 13) (500 mg, 1.04 mmol.) was treated with sodium hydroxide (83 mg, 2.08 mmol.), followed by formic acid (0.77 mL) and aqueous formaldehyde solution (0.15 mL). The mixture was heated to reflux for 4 H. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (130 mg) by filtration. m/e=376.

| Analysis | Calculated | Found |
|---|---|---|
| C | 67.99 | 67.88 |
| H | 6.93 | 6.73 |
| N | 5.66 | 5.69 |

EXAMPLE 46

Preparation of (−)-(S)-6-methyl-1,2,3,4-tetrahydro-1-[(3,4-dimethylphenyl)methyl]-9H-pyrido[3,4-b]indole hydrochloride To a stirred solution of 6-methyl-1,2,3,4-tetrahydro-9H-pyrido[3,4-b]indole (3.14 g, 16.9 mmol.) in dry xylenes (65 mL) was added (S)-N,N-dimethyl-N'-(1-tert-butoxy-3-methyl)-2-butylformamidine (3.79 g, 17.7 mmol.) followed by camphorsulfonic acid (200 mg). The resulting solution was heated to reflux for 72 hours. The solution was cooled to ambient temperature and concentrated under reduced pressure. The residue was purified by flash chromatography on silica gel (1:3:6 triethylamine:ethyl acetate:hexanes as eluent). The product containing fractions were pooled and concentrated to afford the product formamidine (5.99 g) as a viscous oil which was used without further purification.

To a stirred, cooled (0° C.) suspension of potassium hydride (25% oil dispersion, 829 mg, 20.2 mmol.) in THF (10 mL) was added formamidine prepared above (5.99 g , 16.8 mmol.) in THF (45 mL). To this mixture was added tetramethylethylenediamine (3.0 mL, 20.2 mmol.) followed by chloromethylmethyl ether (1.9 mL, 25.2 mmol.). The mixture was stirred for an additional 1 hour and treated with water (50 mL). The mixture was partitioned between diethyl ether and water and the layers separated. The aqueous phase was extracted with diethyl ether (2×100 mL) and the organic phases combined, dried over potassium carbonate, and concentrated to afford product (6.73 g) as an orange oil, which was used without further purification.

To a stirred, cooled (−78° C.) solution of previously prepared formamidine (6.29 g, 8.4 mmol.) in dry THF (100 mL) was added n-BuLi (1.7M solution in hexanes, 10.1 mL, 17.1 mmol.) dropwise over 5 minutes. The solution was further stirred at −78° C. solution for 1 hour and treated with 1-chloromethyl-3,4-dimethoxybenzene (3.35 g, 17.9 mmol.) in dry THF (15 mL). The solution was further stirred for 4 hours at −78° C. and allowed to warm to room temperature overnight. Wet THF was added (50 mL) and the solution was concentrated under reduced pressure. The residue was dissolved in chloroform and washed with water. The organic phase was dried over sodium carbonate and concentrated. The crude product was purified by flash chromatography on silica gel (1:3:6 triethylamine:ethyl acetate:hexanes as eluent). The product containing fractions (upper Rf) were pooled and concentrated to afford product (3.92 g) as a viscous oil (m/e=550) which was used without further purification.

To a stirred solution of methoxymethylindole prepared above (3.92 g , 7.13 mmol.) in THF (70 mL) was added 2N HCl (20 mL). The mixture was stirred at ambient temperature for 24 hours, and partitioned between diethyl ether and water. The aqueous phase was back extracted with diethyl ether (2×50 mL) and the combined organic phases were washed with brine, dried over sodium carbonate, and concentrated under reduced pressure. The residue was dissolved in THF (20 mL) and treated with 2N sodium hydroxide solution (6 mL). After 2 hours, the reaction mixture was extracted with chloroform (2×100 mL). The organic phase was dried over sodium carbonate and concentrated. Chromatography on silica gel (1:3:6 triethylamine/ethyl acetate/hexanes as eluent) afforded product (1.85 g) as a viscous oil (m/e=505).

To a stirred, cooled (0° C.) solution of previously prepared formamidine (1.37 g, 5.41 mmol.) in ethanol (50 mL) was added water (6 mL) followed by acetic acid (6 mL) and hydrazine hydrate (11 mL). The reaction vessel was placed in the freezer (−10° C.) for 72 hours. The mixture was warmed to ambient temperature and concentrated under reduced pressure. The crude product was dissolved in chloroform (300 mL) and washed with water (3×50 mL). The organic phase was dried over sodium carbonate and concentrated to a viscous oil. The oil was dissolved in diethyl ether and treated with anhydrous HCl. The hydrochloride salt (560 mg) was isolated by filtration. Recrystallization from ethanol (2×) afforded material of constant rotation. Chiral HPLC confirmed enantiomeric purity as >98% ee. m/e=336)

specific rotation @ 589 nM=−118.0 (pyridine, C=1)

specific rotation @ 365 nM=−401.0 (pyridine, C=1)

| Analysis | Calculated | Found |
|---|---|---|
| C | 67.64 | 67.65 |
| H | 6.76 | 6.70 |
| N | 7.51 | 7.52 |

EXAMPLE 47

Preparation of (±)6-methyl-1-(1-(4-methoxy-naphthalenyl)methyl)-1,2,3,4-tetrahydro-9H-pyrido[3,4-b]-indole hydrochloride

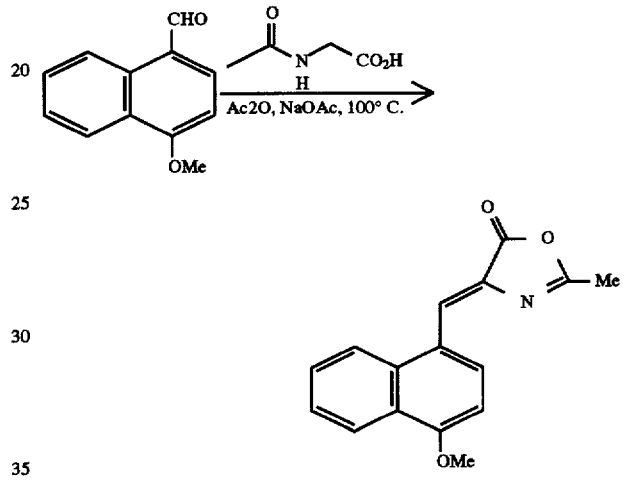

A solution of 4-methoxy-1-naphthaldehyde (20.0 g, 0.107 mol.), N-acetylglycine (12.58 g, 0.107 mol.) and sodium acetate (8.81 g, 0.107 mol) in acetic anhydride mL ) was heated to 100° C. for 2 hours. The reaction mixture was cooled to ambient temperature and stirred for 10 hours under nitrogen atmosphere. The mixture was poured onto ice (250 mL) with stirring. The product was isolated by filtration, washed with water (3×50 mL) and diethyl ether (3×50 mL) and dried under reduced pressure (3.16 g).

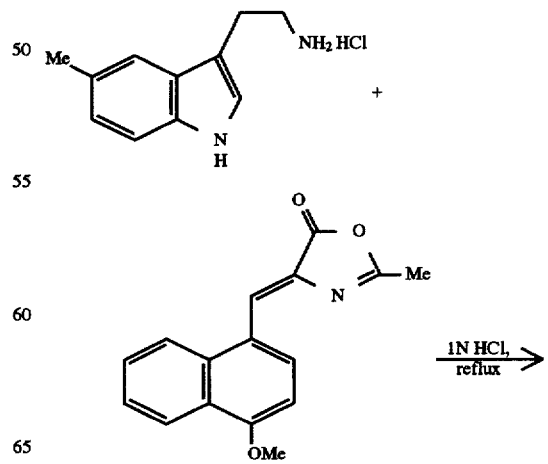

67

-continued

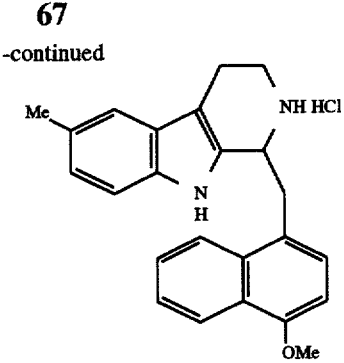

A suspension of azalactone prepared above (2.00 g, 7.5 mmol.) and 5-methyl-tryptamine hydrochloride (1.18 g, 5.62 mmol.) in 1N HCl (20 mL) was heated to reflux for 48 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 1.42 g of desired product as a pale solid. (mp 271.7° C.)

| Analysis: | Calculated | Found |
| --- | --- | --- |
| C | 73.36 | 73.60 |
| H | 6.41 | 6.51 |
| N | 7.13 | 7.20 |

EXAMPLE 48

Preparation of (±)6-methyl-1-(1-(2-methoxy-naphthalenyl)methyl)1,2,3,4-tetrahydro-9H-pyrido [3,4-b]-indole hydrochloride To a stirred, cooled (−78° C.) solution of methoxymethyl-triphenylphosphonium chloride (11.05 g, 32.2 mmol.) in 150 mL of anhydrous THF was added n-butyllithium (20.14 mL of 1.6M solution in hexanes, 32.2 mmol) dropwise via syringe. After complete addition, the solution was stirred at this temperature for 15 min. A solution of 2-methoxy-1-naphthaldehyde (5.0 g, 26.9 mmol.) in THF (75 mL) was added to the solution dropwise by addition funnel. After complete addition, the solution was allowed to warm to ambient temperature and stir for 14 hours. A saturated solution of ammonium chloride (100 mL) was added and the mixture was partitioned between diethyl ether and water. The organic phase was dried over anhydrous sodium sulfate, filtered and concentrated under reduced pressure. The crude residue was purified by plug filtration (silica gel, eluent 40% ethyl acetate/hexanes) and afforded 5.0 g of product as a mixture of enol ethers, which was used without further purification.

A solution of enol ethers prepared above (5.0 g, 23.3 mmol.) in diethyl ether (50 mL) was treated with water (1.0 mL) and perchloric acid (1.5 mL of 60% solution). The solution was stirred at ambient temperature for 72 hours. The solution was diluted with chloroform (100 mL) and neutralized with saturated sodium bicarbonate solution. The mixture was extracted with chloroform (3×100 mL) and the combined organic phases were dried over sodium sulfate and concentrated. The residue was purified by flash chromatography on silica gel (5% diethyl ether/hexanes as eluent) to afford (2-methoxy-1-naphthyl)-acetaldehyde (1.79 g) as a colorless oil.

To a stirred solution of 5-methyltryptamine hydrochloride (947 mg, 4.49 mmol.) in 20 mL of ethyl alcohol was added

68

(2-methoxy-1-naphthyl)-acetaldehyde (1.0 g, 4.99 mmol.). The solution was heated to reflux under nitrogen atmosphere for 40 hours. The reaction mixture was cooled to ambient temperature and the crude product isolated by filtration. Recrystallization from ethyl alcohol/2-butanone afforded product as a pale solid (705 mg). (mp. 245.3° C.).

| Analysis: | Calculated | Found |
| --- | --- | --- |
| C | 73.36 | 73.29 |
| H | 6.41 | 6.64 |
| N | 7.13 | 7.12 |

EXAMPLE 49

Preparation of (±)6-methyl-1-(1-naphthalenyl-1-ethyl)-1,2,3,4-tetrahydro-9H-pyrido [3,4-b]indole (Z)2-butenedioate

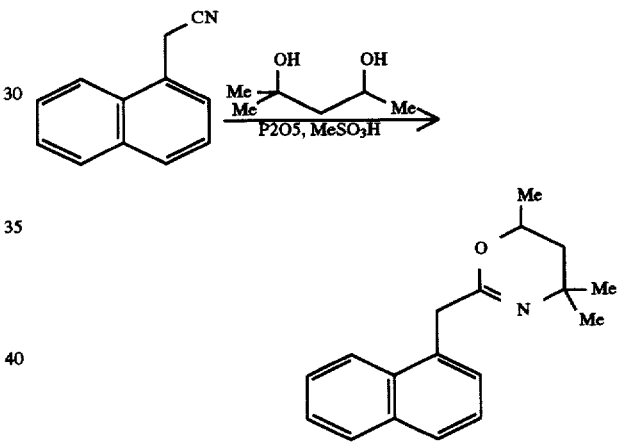

To methanesulfonic acid (215 mL) was added phosphorus pentoxide (31.8 g) slowly with stirring. After the addition was complete, the mixture was further stirred under nitrogen atmosphere for 2 hours until homogeneous. To this solution was added 1-naphthyl acetonitrile (50 g, 0.3 mol.) in a single portion, followed by 2-methyl-2,4-pentanediol (76.4 mL, 0.6 mol.) dropwise at such a rate as to maintain a temperature between 25° and 30° C. (1 hour). After complete addition, the reaction mixture was stirred at ambient temperature for 10 hours and poured onto ice (500 g). The mixture was made basic with sodium hydroxide solution (50%), added at such a rate as to keep the temperature below 35° C. The mixture was extracted with diethyl ether (3×250 mL) and the combined organic phases were dried over magnesium sulfate and concentrated under reduced pressure to afford a green solid. Recrystallization from ethyl acetate afforded product (28.29 g which was used without further purification.

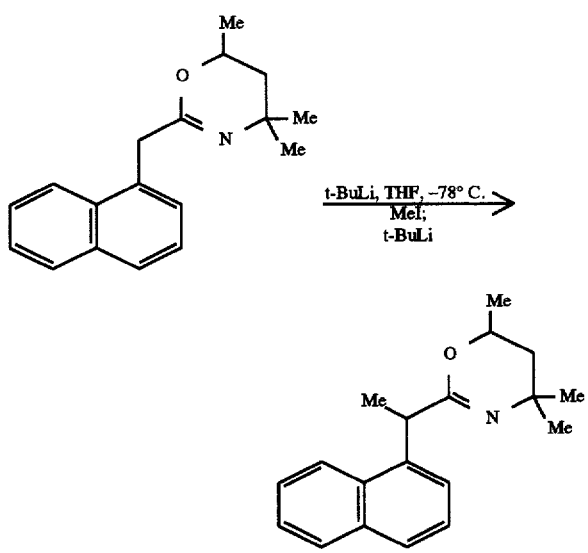

To a stirred, cooled (−78° C.) solution of previously prepared "isoxazan?" (28.3 g, 0.106 mol.) in THF (475 mL) under argon atmosphere was added t-butyllithium solution (68.4 mL, 1.7M in pentane, 0.116 mol.) dropwise via syringe over 15 minutes. After complete addition, the orange solution was stirred at −78° C. for 30 minutes. Methyl iodide (6.6 mL, 0.106 mol.) was added dropwise via syringe and the resulting solution further stirred at −78° C. for 45 minutes. t-Butyllithium (68.4 mL, 1.7M in pentane, 0.116 mol.) was added dropwise over 15 minutes and the orange solution stirred for 2 hours. The mixture was poured into ice/water (500 mL) and was acidified to pH 2–3 with 5N HCl solution. The mixture was extracted with diethyl ether (2×100 mL) and these extracts were discarded. The aqueous phase was made basic with sodium hydroxide solution (50%), cooling the mixture with ice when necessary. The basic aqueous phase was extracted with diethyl ether (2×200 mL) and the combined organic extracts were dried over magnesium sulfate, filtered and concentrated to afford product as an oily solid (13.15 g), which was used without further purification.

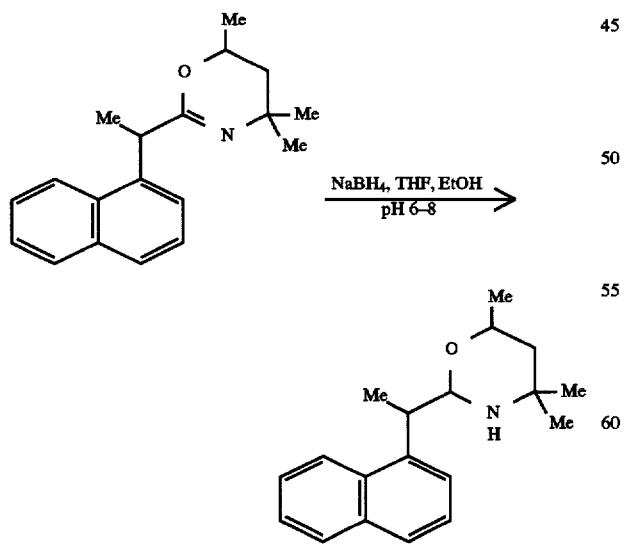

To a stirred cooled (−40° C.) solution of previous product (13.15 g, 46.7 mmol.) in THF (100 mL) and ethyl alcohol (100 mL) was added 5N HCl solution until pH 7. In a separate flask, a solution of sodium borohydride (2.52 g, 65.8 mmol.) was dissolved in water (20 mL) to which 1 drop of 50% sodium hydroxide had been added. Portions of the sodium borohydride solution and 5N HCl solution were alternately added to the reaction mixture such that the pH remained 6–8, at such a rate as to maintain temperature between −35° and −45° C. After complete addition, the reaction mixture was warmed to ambient temperature over about 2 hours. The reaction mixture was made basic with sodium hydroxide solution and extracted with diethyl ether (3×100 mL). The combined organic phases were washed with brine and dried over magnesium sulfate. Filtration and removal of solvent afforded crude product (13.2 g) as a viscous oil, which was used without further purification.

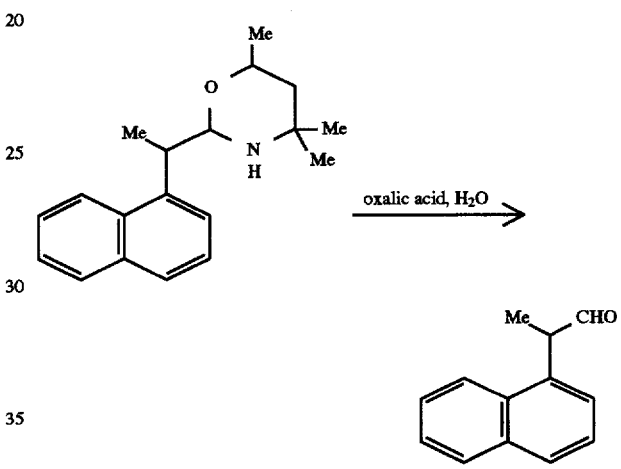

A mixture of crude product from the previous reaction (13.2 g, 46.6 mmol) and oxalic acid dihydrate (19.1 g, 152 mmol.) in water (380 mL) was heated to reflux for 12 hours. The mixture was cooled to ambient temperature and extracted with chloroform (2×100 mL). The combined organic phases were dried over magnesium sulfate, filtered and concentrated to afford aldehyde as an orange oil. Distillation (Kugelrohr) under reduced pressure afforded pure aldehyde (1.97 g) as a pale oil.

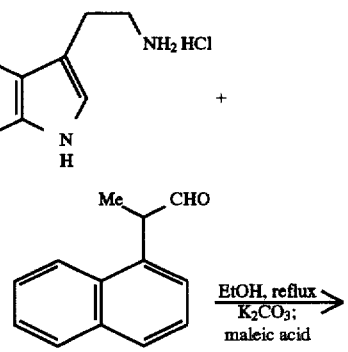

-continued

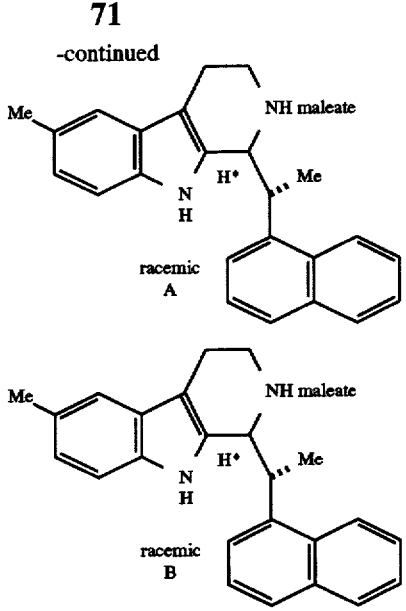

A solution of 5-methyl tryptamine hydrochloride (1.11 g, 5.27 mmol.) and 2-(1-naphthyl)-propionaldehyde (0.97 g, 5.26 mmol.) in 95% ethyl alcohol was heated to reflux for 48 hours under nitrogen atmosphere. The mixture was cooled to ambient temperature and concentrated under reduced pressure. The residue was partitioned between aqueous potassium carbonate solution and chloroform. The chloroform phase was dried over magnesium sulfate and concentrated under reduced pressure. The residue was subjected to flash chromatography on silica gel (25% methyl alcohol in chloroform as eluent), affording 529 mg of the higher rf isomer and 200 mg of the lower rf isomer. Each diastereomer, independently, was dissolved in ethyl acetate and treated with excess maleic acid. The maleate salts were isolated by filtration affording 570 mg of isomer A and 30 mg of isomer B.

| Analysis | Calculated | Found |
|---|---|---|
| C | 73.66 | 73.64 |
| H | 6.18 | 6.13 |
| N | 6.14 | 6.44 | isomer B data: m/e=340

| Analysis | Calculated | Found |
|---|---|---|
| C | 73.66 | 73.41 |
| H | 6.18 | 6.04 |
| N | 6.14 | 5.89 |

EXAMPLE 50

Preparation of (±)6-(1,1-dimethylethyl)-1-(1-naphthalenyl-1-ethyl)-1,2,3,4-tetrahydro-9H-pyrido[3,4-b]indole hydrochloride 4-Chlorobutyryl chloride (300 g, 2.13 mol.) was dissolved in dry THF (3 L). To this solution was added 2,6-lutidine (252 mL) followed by 5% Pd/C (30 g). This mixture was placed in a Parr hydrogenator and shaken under 60 psi of hydrogen for 6 hours. The mixture was purged with nitrogen, filtered, washing the catalyst with THF (500 mL), and concentrated at room temperature under reduced pressure. Distillation afforded 4-chlorobutanal (148.3 g) as a colorless liquid.

To a stirred suspension of 4-isopropylphenylhydrazine hydrochloride monohydrate (15.3 g, 91.95 mmol.) in chloroform (250 mL) was added saturated sodium carbonate solution (250 mL). The mixture was stirred for 30 minutes until the organic phase appeared homogeneous, and extracted with chloroform (2×200 mL). The combined organic phases were concentrated to afford the hydrazine free base as a yellow oil. This oil was dissolved in methanol (200 mL) and water (5 mL) and treated with sodium acetate (6.72 g, 82 mmol.) and 4-chlorobutanal (8.7 g, 82 mmol.). The mixture was placed in a sealable tube and purged with nitrogen for 10 minutes. The tube was sealed and placed in an oil bath preheated to 100° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 5-isopropyl-tryptamine hydrochloride (9.8 g) as a pale solid, which was used without further purification.

A solution of 5-isopropyltryptamine hydrochloride (1.24 g, 5.19 mmol.) and 2-(1-naphthyl)-propionaldehyde (0.95 g, 5.16 mmol.) in 95% ethyl alcohol was heated to reflux for 48 hours under nitrogen atmosphere. The mixture was cooled to ambient temperature and concentrated under reduced pressure. The residue was partitioned between aqueous potassium carbonate solution and chloroform. The chloroform phase was dried over magnesium sulfate and concentrated under reduced pressure. The residue was subjected to flash chromatography on silica gel (25% methyl alcohol in chloroform as eluent), affording 500 mg of the higher rf isomer along with 400 mg of impure lower rf isomer. The major diastereomer was dissolved in ethyl acetate and treated with excess maleic acid. The maleate salt was isolated by filtration affording 400 mg of named product as a pale solid.

| Analysis | Calculated | Found |
|---|---|---|
| C | 74.36 | 74.58 |
| H | 6.66 | 6.64 |
| N | 5.78 | 5.81 |

EXAMPLE 51

Preparation of (±)6-methyl-1-(1-naphthalenylmethyl)-1,2,3,4-tetrahydro-9H-pyrido[3,4-b]indole hydrochloride A solution of 1-naphthaldehyde (25.0 g, 0.16 mol.), N-acetylglycine (19.0 g, 0.162 mol.) and sodium acetate (13.1 g, 0.160 mol) in acetic anhydride (147 mL) was heated to 100° C. for 4 hours. The reaction mixture was cooled to ambient temperature poured onto ice (300 mL) with stirring. The product was isolated by filtration, washed with water (3×50 mL) and diethyl ether (3×50 mL) and dried under reduced pressure (11.82 g).

A suspension of azalactone prepared above (3.15 g, 13.3 mmol.) and 5-methyl-tryptamine hydrochloride (2.0 g, 9.5 mmol.) in 1N HCl (50 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 1.94 g of desired product as a pale solid.

| Analysis | Calculated | Found |
|---|---|---|
| C | 76.12 | 76.03 |
| H | 6.39 | 6.22 |
| N | 7.72 | 7.52 |

EXAMPLE 52

Preparation of (±)8-bromo-1-(1-naphthalenylmethyl)-1,2,3,4-tetrahydro-9H-pyrido[3,4-b]indole hydrochloride

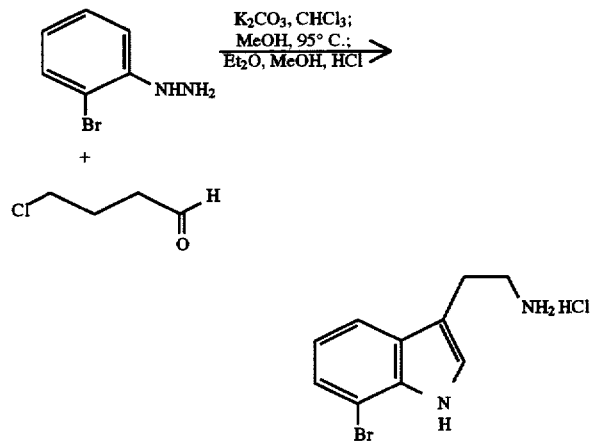

To a stirred suspension of 2-bromophenyl-hydrazine hydrochloride (25.8 g, 115 mmol.) in chloroform (500 mL) was added saturated sodium carbonate solution (500 mL). The mixture was stirred for 30 minutes until the organic phase appeared homogenous, and extracted with chloroform (2×200 mL). The combined organic phases were concentrated to afford the hydrazine free base as a yellow oil. This oil was dissolved in methanol (100 mL) and treated slowly with 4-chlorobutanal (prepared as described in Example 4) (12.3 g, 115 mmol.). The mixture was placed in a sealable tube and purged with nitrogen for 10 minutes. The tube was sealed and placed in an oil bath preheated to 95° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromo-tryptamine hydrochloride (3.6 g) as a pale solid, which was used without further purification.

A suspension of azalactone (prepared as described in Example 5) (55 g, 6.53 mmol.) and 7-bromo-tryptamine hydrochloride (1.50 g, 5.44 mmol.) in 1N HCl (100 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 260 mg of desired product as a pale solid. (mp= 231°–233° C., dec.)

| Analysis | Calculated | Found |
|---|---|---|
| C | 61.77 | 61.48 |
| H | 4.71 | 4.63 |
| N | 6.55 | 6.73 |

EXAMPLE 53

Preparation of (±)8-bromo-1-(1-naphthalenylmethyl)-1,2,3,4-tetrahydro-9H-pyrido[3,4-b]indole hydrochloride To a stirred suspension of 2-bromophenyl-hydrazine hydrochloride (25.8 g, 115 mmol.) in chloroform (500 mL) was added saturated sodium carbonate solution (500 mL). The mixture was stirred for 30 minutes until the organic phase appeared homogenous, and extracted with chloroform (2×200 mL). The combined organic phases were concentrated to afford the hydrazine free base as a yellow oil. This oil was dissolved in methanol (100 mL) and treated slowly with 4-chlorobutanal (prepared as described in Example 4) (12.3 g, 115 mmol.). The mixture was placed in a sealable tube and purged with nitrogen for 10 minutes. The tube was sealed and placed in an oil bath preheated to 95° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromo-tryptamine hydrochloride (3.6 g) as a pale solid, which was used without further purification.

A suspension of azalactone (prepared as described in Example 5) (55 g, 6.53 mmol.) and 7-bromo-tryptamine hydrochloride (1.50 g, 5.44 mmol.) in 1N HCl (100 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 260 mg of desired product as a pale solid. (mp= 231°–233° C., dec.)

| Analysis | Calculated | Found |
|---|---|---|
| C | 61.77 | 61.48 |
| H | 4.71 | 4.63 |
| N | 6.55 | 6.73 |

EXAMPLE 54

Preparation of (±)8-methoxy-1-(1-naphthalenylmethyl)-1,2,3,4-tetrahydro-9H-pyrido [3,4-b]indole (Z)-2-butenedioate To a stirred, cooled (0° C.) suspension of 2-methoxyphenylhydrazine hydrochloride (14.44 g, 83 mmol.) in THF (600 mL) was added 4-chlorobutanal prepared as described in Example 5 (9.0 g, 84 mmol.) followed by dropwise addition of triethylamine (8.6 g, 85 mmol.) in THF (20 mL). Upon complete addition, the cooling bath was removed and the solution stirred for 1 hour. The reaction mixture was filtered and the filter cake washed with THF (100 mL). The combined filtrates were concentrated to an orange oil, which was dissolved in methanol (150 mL) and water (5 mL). The solution was transferred to a sealable tube and purged with nitrogen for 10 minutes. The tube was sealed and placed in an oilbath preheated to 95° C. After heating for 14 hours, the reaction mixture was cooled to ambient temperature and concentrated under reduced pressure. The residue was partitioned between saturated aqueous potassium carbonate and 3:1 chloroform:2-propanol. The organic phase was dried over sodium sulfate and concentrated. The residue was purified by flash chromatography on silica gel (15% methanol, 0.2% NH₄OH, in chloroform as eluent). The fractions containing product were pooled and concentrated under reduced pressure. The residue was dissolved in methanol and treated with dry HCl and concentrated to afford 7-methoxytryptamine hydrochloride (4.04 g) as a stable foam, which was used without further purification.

A suspension of azalactone (prepared as described in Example 5) (1.30 g, 5.5 mmol.) and 7-methoxytryptamine hydrochloride (1.08 g, 4.8 mmol.) in 1N HCl (100 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (880 mg) by filtration. (mp=226°–227° C., dec.)

| Analysis | Calculated | Found |
|---|---|---|
| C | 70.73 | 70.61 |
| H | 5.72 | 5.77 |
| N | 6.11 | 6.03 |

EXAMPLE 55

Preparation of (±)6-bromo-1-(1-naphthalenylmethyl)-1,2,3,4-tetrahydro-9H-pyrido [3,4-b]indole (Z)-2-butenedioate A suspension of azalactone (prepared as described in Example 5) (1.4 g, 5.9 mmol.) and 5-bromotryptamine hydrochloride (1.77 g, 6.4 mmol.) in 1N HCl (100 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (540 mg) by filtration. (mp=234°–235° C., dec.) m/e=390.

| Analysis | Calculated | Found |
|---|---|---|
| C | 61.55 | 61.38 |
| H | 4.57 | 4.64 |
| N | 5.52 | 5.29 |

EXAMPLE 56

Preparation of (±)7-methyl-8-bromo-1-(1-naphthalenyl methyl)-1,2,3,4-tetrahydro-9H-pyrido [3,4-b]indole hydrochloride 2-Bromo-3-methylphenylhydrazine hydrochloride (23 g) was prepared as described for 2-bromo-4 methylphenylhydrazine hydrochloride in Example 7, except using 2-bromo-3-methylaniline as starting material.

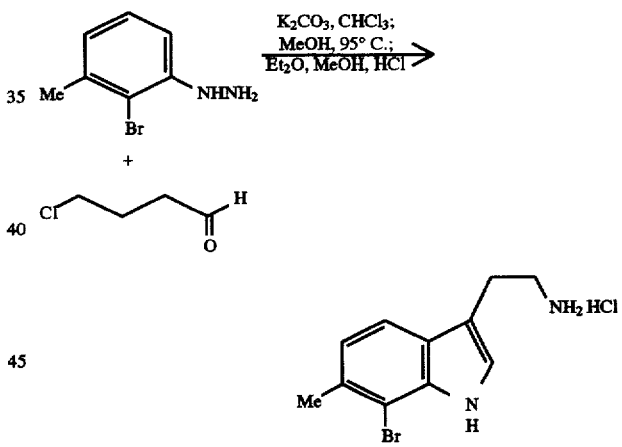

6-Methyl-7-bromotryptamine hydrochloride was prepared (2.42 g) as described for 5-methyl-7-bromotryptamine hydrochloride in Example 7, except using 2-bromo-3-methyl phenylhydrazine hydrochloride as starting material.

A suspension of azalactone (prepared as described in Example 5) (1.07 g, 4.51 mmol.) and 6-methyl-7-bromotryptamine hydrochloride (1.22 g, 4.21 mmol.) in 1N HCl (70 mL) was heated to reflux for 65 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with dry HCl. The product was isolated as the hydrochloride salt (840 mg) by filtration. (mp=276°-279° C., dec.)

| Analysis | Calculated | Found |
|---|---|---|
| C | 62.53 | 62.79 |
| H | 5.02 | 4.96 |
| N | 6.34 | 6.19 |

EXAMPLE 57

Preparation of (±)6-cyclohexyl-1-(1-naphthalenylmethyl)-1,2,3,4-tetrahydro-9H-pyrido[3,4-b]indole hydrochloride 4-Cyclohexyl phenylhydrazine hydrochloride (35.6 g) was prepared as described for 2-bromo-4 methylphenylhydrazine hydrochloride in Example 7, except using 4-cyclohexyl-aniline as starting material.

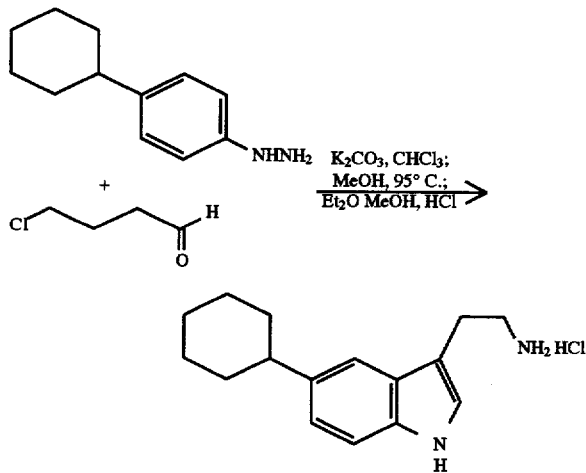

5-Cyclohexyltryptamine hydrochloride was prepared (1.29 g) as described for 5-methyl-7-bromotryptamine hydrochloride in Example 7, except using 4-cyclohexylphenylhydrazine hydrochloride as starting material.

A suspension of azalactone (prepared as described in Example 5) (1.09 g, 4.59 mmol.) and 5-cyclohexyltryptamine hydrochloride (1.28 g, 4.59 mmol.) in 1N HCl (70 mL) was heated to reflux for 14 hours under nitrogen atmosphere. The reaction mixture was cooled to ambient temperature and the crude product isolated by filtration. The solid was recrystallized from ethanol (2×) to afford 690 mg of desired product as a pale solid hydrochloride salt. m/e=395

| Analysis | Calculated | Found |
|---|---|---|
| C | 78.03 | 78.26 |
| H | 7.25 | 7.06 |
| N | 6.50 | 6.48 |

EXAMPLE 58

Preparation of (±)2,6-dimethyl-1-(1-naphthalenylmethyl)-1,2,3,4-tetrahydro-9H-pyrido[3,4-b]indole hydrochloride To an aqueous solution (200 mL) of 5-methyl-1-(1-naphthalenylmethyl)-1,2,3,4-tetrahydro-9H-pyrido[3,4-b]indole hydrochloride (2.00 g, 5.51 mmol.) previously prepared in Example 5, was added formic acid (4.1 mL) and formaldehyde solution (0.8 mL of 37% aqueous solution). The mixture was heated to reflux for 72 hours. The solution was made basic with saturated potassium carbonate solution and extracted with chloroform (2×100 mL). The combined organic phases were dried over potassium carbonate and concentrated under reduced pressure. The crude product was purified by flash chromatography on silica gel (chloroform as eluent). The fractions containing product were pooled and concentrated to a viscous oil. The oil was dissolved in diethyl ether and treated with anhydrous HCl and the resulting hydrochloride salt was isolated by filtration. Drying afforded the named product (1.34 g). m/e=340.

| Analysis | Calculated | Found |
|---|---|---|
| C | 76.48 | 76.58 |
| H | 6.68 | 6.63 |
| N | 7.43 | 7.28 |

EXAMPLE 59

Preparation of (±)5-fluoro-6-methyl-1-(1-naphthalenylmethyl)-1,2,3,4-tetrahydro-9H-pyrido[3,4-b]indole (Z)-2-butenedioate 3-fluoro-4-methyl-phenylhydrazine hydrochloride (21.4 g) was prepared as described for 2-bromo-4 methyl-phenylhydrazine hydrochloride in Example 7, except using 3-fluoro-4-methyl aniline as starting material.

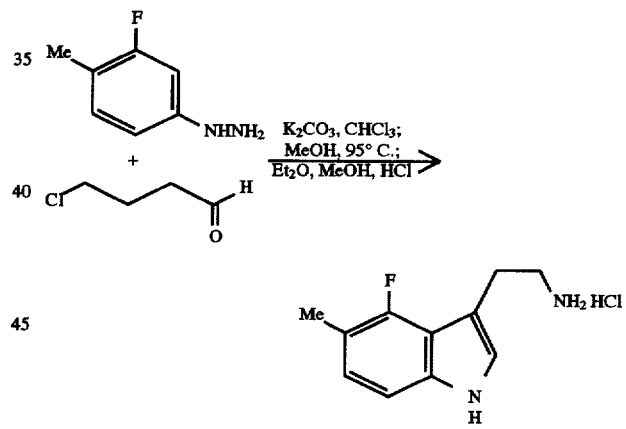

4-Fluoro-5-methyltryptamine hydrochloride was prepared (2.20 g) as described for 5-methyl-7-bromotryptamine hydrochloride in Example 7, except using 3-fluoro-4-methyl-phenylhydrazine hydrochloride (6.00 g) as starting material.

A suspension of azalactone (prepared as described in Example 5) (2.3 g, 9.6 mmol.) and 4-fluoro-5-methyltryptamine hydrochloride (2.2 g, 9.6 mmol.) in 1N HCl (40 mL was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated

EXAMPLE 60

Preparation of (±)7,8,9,10-tetrahydro-10-(1-naphthalenylmethyl)-11H-benzo[g]pyrido[3,4-b]indole (Z)-2-butenedioate

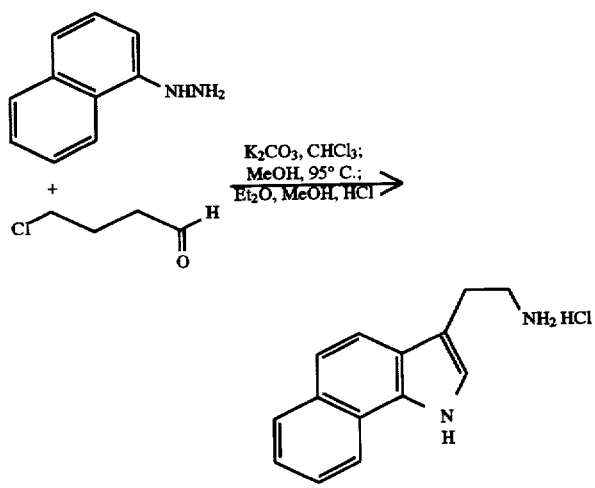

6,7-benzotryptamine hydrochloride was prepared (2.85 g) as described for 5-methyl-7-bromotryptamine hydrochloride in Example 7, except using 1-naphthyl-hydrazine hydrochloride (6.00 g) as starting material.

A suspension of azalactone (prepared as described in Example 5) (2.75 g, 11.6 mmol.) and 6,7-benzotryptamine hydrochloride (2.85 g, 11.6 mmol.) in 1N HCl (50 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (300 mg) by filtration. m/e=363.

| Analysis | Calculated | Found |
| --- | --- | --- |
| C | 75.30 | 75.04 |
| H | 5.48 | 5.36 |
| N | 5.85 | 5.76 |

EXAMPLE 61

Preparation of (±)6-(1,1-dimethylethyl)-1,2,3,4-tetrahydro-1-(1-naphthalenylmethyl)-9H-pyrido[3,4b]indole (Z)-2-butenedioate

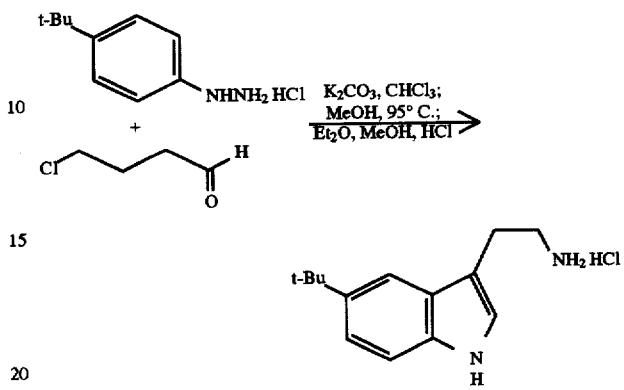

5-(1,1-dimethylethyl)-tryptamine hydrochloride was prepared (2.95 g) as described for 5-methyl-7-bromotryptamine hydrochloride in Example 7, except using 4-(1,1-dimethylethyl)-phenyl hydrazine hydrochloride (6.00 g) as starting material.

A suspension of azalactone (prepared as described in Example 5) (1.25 g, 5.26 mmol.) and 5-(1,1-dimethylethyl)-tryptamine hydrochloride (1.33 g, 5.26 mmol.) in 1N HCl (50 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (700 mg) by filtration. m/e=369

| Analysis | Calculated | Found |
| --- | --- | --- |
| C | 74.36 | 74.08 |
| H | 6.66 | 6.69 |
| N | 5.78 | 5.69 |

EXAMPLE 62

Preparation of (±)6-(1-methylethyl)-1,2,3,4-tetrahydro-1-(1-naphthalenylmethyl)-9H-pyrido[3,4b]indole (Z)-2-butenedioate A suspension of azalactone (prepared as described in Example 5) (1.75 g, 7.38 mmol.) and 5-isopropyltryptamine hydrochloride (prepared as described in Example 4) (1.76 g, 7.37 mmol.) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The solvent was removed under reduced pressure and the residue chromatographed on silica gel (ethyl acetate/0.2% NH$_4$OH as eluent). The fractions containing product were pooled and concentrated under reduced pressure. The residue was dissolved in ethyl acetate containing

---

(from previous page) with maleic acid. The product was isolated as the maleate salt (520 mg) by filtration.

| Analysis | Calculated | Found |
| --- | --- | --- |
| C | 70.42 | 70.45 |
| H | 5.47 | 5.41 |
| N | 6.08 | 6.10 |

1% methanol and treated with maleic acid. The product was isolated as the maleate salt (671 mg) by filtration. m/e=355

| Analysis | Calculated | Found |
|---|---|---|
| C | 74.02 | 74.08 |
| H | 6.43 | 6.21 |
| N | 5.95 | 5.83 |

EXAMPLE 63

Preparation of (±)6,9-dimethyl-1,2,3,4-tetrahydro-1-(1-naphthalenylmethyl)-9H-pyrido[3,4-b]indole hydrochloride To a stirred suspension of 5-methyltryptamine hydrochloride (10.0 g, 43.2 mmol.) in chloroform (300 mL) was added saturated sodium carbonate solution (300 mL). The mixture was stirred at ambient temperature for 1 hour. The layers were separated and the aqueous layer was back extracted with chloroform (2×100 mL). The combined organic layers were dried over sodium sulfate and concentrated. The residue was dissolved in toluene (300 mL) and treated with phthalic anhydride (7.05 g, 47.6 mmol.). The solution was heated to reflux for 14 hours with azeotropic removal of water (by Dean-Stark trap). The solution was cooled to ambient temperature and concentrated to afford crude product as a pale foam. Recrystallization from ethanol afforded product phthalimide (13.52 g) as a white solid, which was used without further purification.

To a stirred, cooled (0° C.) suspension of potassium hydride (25% oil dispersion, 8.24 g, 51.3 mmol.) in dry THF (50 mL) was added a solution of phthalimide prepared above (13.02 g, 42.8 mmol.) in THF (150 mL) over 30 minutes. After complete addition, the mixture was further stirred for 1 hour. Tetramethylethylenediamine (7.7 mL , 51.3 mmol.) was added, followed by methyl iodide (4.0 mL, 63.8 mmol.). After 1 hour, the reaction was quenched by addition of water (200 mL), followed by extraction with diethyl ether (2×100 mL). The combined organic phases were dried over magnesium sulfate and concentrated under reduced pressure to afford product as a yellow solid (14 g) which was used without further purification.

A solution of phalimide prepared in the previous step (14 g, 42.8 mmol.) in methanol (85 mL) was treated with hydrazine (3.4 mL, 109 mmol.). The mixture was heated to reflux for 2 hours. The mixture was cooled to ambient temperature, treated with concentrated HCl (7 mL) and methanol (25 mL), and further heated to reflux for 14 hours. After cooling to ambient temperature, the mixture was partitioned between chloroform (200 mL) and saturated aqueous sodium carbonate solution (200 mL). The aqueous layer was further extracted with chloroform (2×100 mL) and the organic phases combined, dried over sodium sulfate and concentrated. The crude product was purified by flash chromatography on silica gel (0–25% methanol in chloroform/ 0.2% NH$_4$OH as eluent). The product containing fractions were pooled and concentrated under reduced pressure. The residue was dissolved in diethyl ether and treated with anhydrous HCl. The product 1,5-dimethyl-tryptamine hydrochloride (6.08 g) was isolated by filtration as a tan solid and used without further purification.

A suspension of azalactone prepared as described in Example 5 (1.06 g, 4.45 mmol.) and 1,5-dimethyl-tryptamine hydrochloride (1.00 g, 4.47 mmol.) in 1N HCl (50 mL) was heated to reflux for 48 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 710 mg of desired product as a pale solid. m/e=340.

| Analysis | Calculated | Found |
|---|---|---|
| C | 76.48 | 76.78 |
| H | 6.68 | 6.58 |
| N | 7.43 | 7.50 |

EXAMPLE 64

Preparation of (−)-(S)-6-methyl-1,2,3,4-tetrahydro-1-(1-naphthalenylmethyl)-9H-pyrido[3,4-b]indole hydrochloride To a stirred solution of 6-methyl-1,2,3,4-tetrahydro-9H-pyrido[3,4-b]indole (3.14 g, 16.9 mmol.) in dry xylenes (65 mL) was added (S)-N,N-dimethyl-N'-(1-tert-butoxy-3-methyl)-2-butylformamidine (3.79 g , 17.7 mmol.) followed by camphor sulfonic acid (200 mg). The resulting solution was heated to reflux for 72 hours. The solution was cooled to ambient temperature and concentrated under reduced pressure. The residue was purified by flash chromatography on silica gel (1:3:6 triethylamine:ethyl acetate:hexanes as eluent). The product containing fractions were pooled and concentrated to afford the product formamidine (5.99 g) as a viscous oil which was used without further purification.

To a stirred, cooled (0° C.) suspension of potassium hydride (25% oil dispersion, 829 mg, 20.2 mmol.) in THF (10 mL) was added formamidine prepared above (5.99 g, 16.8 mmol.) in THF (45 mL). To this mixture was added tetramethylethylenediamine (3.0 mL, 20.2 mmol.) followed by chloromethylmethyl ether (1.9 mL, 25.2 mmol.). The mixture was stirred for an additional 1 hour and treated with water (50 mL). The mixture was partitioned between diethyl ether and water and the layers separated. The aqueous phase was extracted with diethyl ether (2×100 mL) and the organic phases combined, dried over potassium carbonate, and concentrated to afford product (6.73 g) as an orange oil, which was used without further purification.

To a stirred, cooled (−78° C.) solution of previously prepared formamidine (3.36 g, 8.4 mmol.) in dry THF (55 mL) was added n-BuLi (1.7M solution in hexanes, 5.4 mL, 9.18 mmol.) dropwise over 5 minutes. The solution was further stirred at −78° C. solution for 1 hour and treated with 1-chloromethyl-naphthalene (1.62 g, 9.18 mmol.) in dry THF (10 mL). The solution was further stirred for 4 hours at −78° C. and allowed to warm to room temperature overnight. Wet THF was added (50 mL) and the solution was concentrated under reduced pressure. The residue was dissolved in chloroform and washed with water. The organic phase was dried over sodium carbonate and concentrated. The crude product was purified by flash chromatography on silica gel (1:3:6 triethylamine:ethyl acetate:hexanes as eluent). The product containing fractions were pooled and concentrated to afford product (3.48 g) as a viscous oil (m/e=539) which was used without further purification.

To a stirred solution of methoxymethyl indole prepared above (3.48 g , 6.45 mmol.) in THF (30 mL) was added 2N HCl (30 mL). The mixture was stirred at ambient temperature for 24 hours, and partitioned between diethyl ether and water. The aqueous phase was back extracted with diethyl ether (2×50 mL) and the combined organic phases were washed with brine, dried over sodium carbonate, and concentrated under reduced pressure. The residue was dissolved in THF (20 mL) and treated with 2N sodium hydroxide solution (6 mL). After 2 hours, the reaction mixture was extracted with chloroform (2×100 mL). The organic phase was dried over sodium carbonate and concentrated to afford product (2.68 g) as a viscous oil (m/e=495).

To a stirred, cooled (0° C.) solution of previously prepared formamidine (2.68 g, 5.41 mmol.) in ethanol (100 mL) was added water (12 mL) followed by acetic acid (12 mL) and hydrazine hydrate (22 mL). The reaction vessel was placed in the freezer (−10° C.) for 72 hours. The mixture was warmed to ambient temperature and concentrated under reduced pressure. The crude product was dissolved in chloroform (300 mL) and washed with water (3×50 mL). The organic phase was dried over sodium carbonate and concentrated to a viscous oil. The oil was dissolved in diethyl ether and treated with anhydrous HCl. The hydrochloride salt (1.50 g) was isolated by filtration. Recrystallization from ethanol (2×) afforded material of constant rotation. Chiral HPLC confirmed enantiomeric purity as >95% ee. m/e=326)

specific rotation @ 589 nM=−40.21 (pyridine, C=1)
specific rotation @ 365 nM=+80.43 (pyridine, C=1)

| Analysis | Calculated | Found |
|---|---|---|
| C | 76.12 | 75.96 |
| H | 6.39 | 6.56 |
| N | 7.72 | 7.44 |

EXAMPLE 65

Preparation of 6-methyl-1-[(4-dimethylamino-naphthalenyl)methyl]-1,2,3,4-tetrahydro-9H-pyrido[3,4-b]indole dihydrochloride-monohydrate To a stirred, cooled (−78° C.) suspension of methoxymethyl-triphenylphosphonium chloride (10.32 g, 30.1 mmol.) in dry THF (150 mL) was added n-BuLi solution 18.8 mL. 1.6M, 30.1 mmol.) dropwise by syringe. The orange suspension was stirred at −78° C. for 15 min. A solution of 4-dimethylamino-1-naphthaldehyde (5.00 g, 25.1 mmol.) in THF (75 mL) was added to the ylide dropwise over 10 min. The reaction mixture was gradually warmed to ambient temperature and stirred 14 H. Saturated ammonium chloride solution (100 mL) was added and the mixture extracted with diethyl ether (3×50 mL). The combined organic phases were dried over sodium sulfate and concentrated under reduced pressure. Chromatography on silica gel, eluting with 15% ethyl acetate/hexanes afforded product (5.43 g) as a mixture of olefin isomers which was used without further purification.

A mixture of 5-methyltryptamine hydrochloride (695 mg, 3.3 mmol.) and 1-methoxy-4'-dimethylamino-benzostyrene (1.00 g, 4.4 mmol.) in acetonitrile (20 mL) and 1N HCl solution (150 mL) was heated to reflux for 96 H, with addition of 1 mL of conc HCl added at 4 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/ 0.2% NH$_4$OH as eluent). The fractions containing product were pooled and concentrated under reduced pressure. The residue was dissolved in ethyl acetate and treated with anhydrous HCl. The product was isolated as the dihydrochloride salt monohydrate (1.22 g) by filtration. mp. 231.3° C.

| analysis: | calculated | found |
|---|---|---|
| C | 65.21 | 65.30 |
| H | 6.79 | 6.60 |
| N | 9.13 | 9.03 |

EXAMPLE 66

7-methyl-8-bromo-1,2,3,4-tetrahydro-9H-pyrido[3,4b]-indole

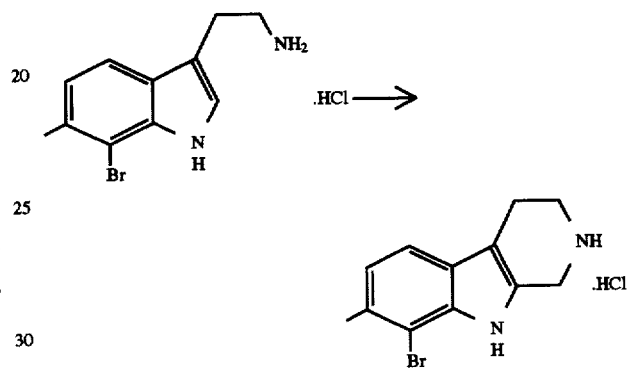

A 3.0 g sample of 6-methyl-7-bromo-1H-indole-3-ethanamine hydrochloride was dissolved in warm water. A solution of glyoxylic acid monohydrate (1.0 g) in water was added. The solution was adjusted to pH 4 using either potassium hydroxide or hydrochloride acid. A solid was suspended in water and concentrated HCl was added slowly. The mixture was boiled. A solid was collected, washed with water, and vacuum dried. The solid was partitioned between 1N NaOH and chloroform. The organic portion was dried and concentrated to a residue which was chromatographed on silica gel using methanol in chloroform. The desired fractions were pooled and concentrated to a solid which was dissolved in methanol, treated with gaseous HCl, and diluted with ether. A solid was collected, washed with ether, and dried.

Yield: 48%

Melting Point: 321° C.

Elemental Analysis: C 47.83; H 4.89; N 9.30.

EXAMPLE 67

8-methoxy-1,2,3,4-tetrahydro-9H-pyrido[3,4b]-indole

The desired product was prepared using substantially the process of Example 66, except that the starting material was 7-methoxy-1H-indole-ethanamine.

Melting Point: 207°–209° C.

Elemental Analysis: C 60.17; H 5.56; N 8.60.

EXAMPLE 68

8-methoxy-2(N)-propyl-1,2,3,4-tetrahydro-9H-pyrido[3,4b]-indole

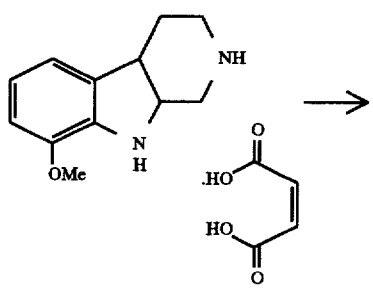

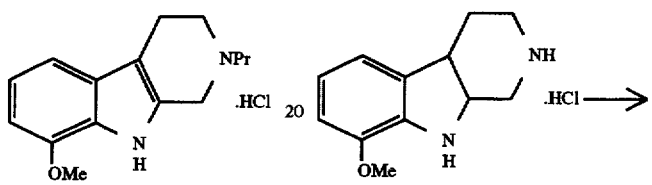

A sample of 8-methoxy-1,2,3,4-tetrahydro-9H-pyrido[3,4b]-indole was prepared substantially as described in Example 66. A 0.36 g sample of the indole was contacted with 1 g $K_2CO_3$ and the mixture was purged with nitrogen. A 40 mL sample of $CH_3CN$ was added to the resulting mixture. A 0.12 mL sample of 1-iodopropane was added. The mixture was maintained under nitrogen and stirred in the dark. The resulting mixture was extracted. The organic phase was dried, evaporated, and chromatographed. The desired fractions were evaporated, taken up into methanol-:ethyl acetate. The resulting mixture was added to a stirring ether solution through which gaseous HCl was bubbled. The resulting solid was vacuum dried, recrystallized, and evaporated to yield the desired product.

Yield: 0.10 g
Melting Point: 282°–284° C.
Elemental Analysis: C 64.45; H 7.67; N 9.91.

EXAMPLE 69

8-methoxy-2(N)-methyl-1,2,3,4-tetrahydro-9H-pyrido[3,4b]-indole

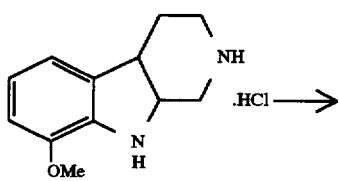

A sample of 8-methoxy-1,2,3,4-tetrahydro-9H-pyrido[3,4b]-indole was prepared substantially as described in Example 66. The indole (1 g), NaOAc (0.34 g), $NaBH_3CN$ (0.53 g), methanol (50 mL), and HOAc (1.0 g) were stirred.

A 1.36 g (37% in 10 mL methanol) sample of $CH_2O$ was added to the indole mixture.

The reaction was quenched using an acid, then made basic, and extracted. The organic was dried, evaporated, and chromatographed. The desired fractions were evaporated and taken up into methanol/ethyl acetate. The resulting mixture was added to ethereal HCl. The resulting solid was collected and vacuum dried.

Yield: 0.84 g (79%)
Melting Point: 291°–294° C.
Elemental Analysis: C 62.06; H 6.97; N 11.32.

EXAMPLE 70

8-methoxy-2(N)-cyclopropylmethyl-1,2,3,4-tetrahydro-9H-pyrido[3,4b]-indole

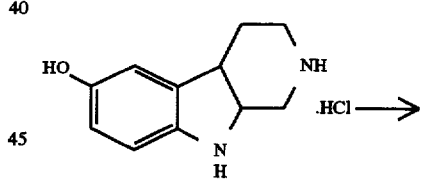

The desired product was prepared using appropriate reagents and the process substantially as described in Example 69.

Yield: 88%
Melting Point: 285°–287° C.
Elemental Analysis: C 65.76; H 7.47; N 9.47.

EXAMPLE 71

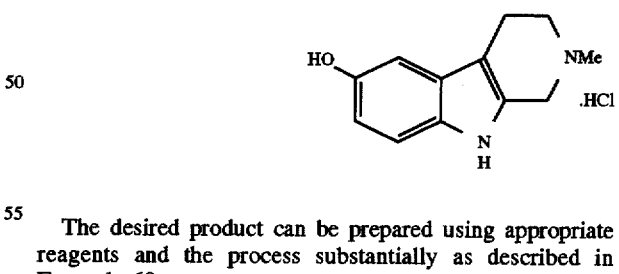

The desired product can be prepared using appropriate reagents and the process substantially as described in Example 69.

Yield: 48%
Melting Point: 321° C.
Elemental Analysis: C 47.83; H 4.89; N 9.30.

EXAMPLE 72

7,8-dimethyl-1,2,3,4-tetrahydro-9H-pyrido[3,4b]-indole

A 2.30 g sample of 6,7-dimethyl-1H-indole-ethanamine was dissolved in a mixture of water and isopropanol with heating. A 1.03 g sample of glyoxilic acid monohydrate in 10 mL of water was added to the flask. The solution was allowed to cool and made basic by the addition of potassium hydroxide. The reaction was stirred for 48 hours. The resulting solid was isolated by filtration and washed with water. The solid was dissolved in 50 mL of water and the solution was acidified by the slow addition of concentrated HCl. Heating was initiated and an additional 5 mL of concentrated HCl was added. The resulting solid was isolated by decanting and dissolved in 10 mL of water. This solution was made basic by the addition of potassium hydroxide and extracted using 1:3 isopropanol:CHCl$_3$. Separation and concentration of the organic layer gave a viscous oil which was purified via chromatography. The oil was dissolved in ethyl acetate and gaseous HCl was bubbled into the solution to form the hydrochloride salt. The solid hydrochloride salt was isolated by filtration and dried in a vacuum oven.

Yield: 54%

Melting Point: 330° C.

Elemental Analysis: C 65.75; H 7.29; N 11.62.

EXAMPLE 73

6-methyl-8-bromo-1,2,3,4-tetrahydro-9H-pyrido[3,4b]-indole

The desired 6-methyl-8-bromo-1,2,3,4-tetrahydro-9H-pyrido[3,4b]-indole was prepared using appropriate reagents and the process substantially as described in Example 72.

Yield: 57%

Melting Point: 346° C.

Elemental Analysis: C 48.04; H 4.68; N 9.30.

EXAMPLE 74

6,8-difluoro-1,2,3,4-tetrahydro-9H-pyrido[3,4b]-indole

The desired 6,8-difluoro-1,2,3,4-tetrahydro-9H-pyrido[3,4b]-indole was prepared using appropriate reagents and the process substantially as described in Example 72.

Yield: 5%

Melting Point: 350° C.

Elemental Analysis: C 53.90; H 4.49; N 11.23.

EXAMPLE 75

8-bromo-1,2,3,4-tetrahydro-9H-pyrido[3,4b]-indole

The desired 8-bromo-1,2,3,4-tetrahydro-9H-pyrido[3,4b]-indole was prepared using appropriate reagents and the process substantially as described in Example 72.

Yield: 4%

Melting Point: 337.8° C.

Elemental Analysis: C 46.17; H 4.26; N 9.52.

The following were prepared by the process substantially as described in Example 72.

8-fluoro-1,2,3,4-tetrahydro-9H-pyrido[3,4b]-indole

Yield: 48%

Melting Point: 329.5° C.

Elemental Analysis: C 58.58; H 5.43; N 12.37.

6-chloro-1,2,3,4-tetrahydro-9H-pyrido[3,4b]-indole

Yield: 63%

Melting Point: 317.9° C.

6-bromo-1,2,3,4-tetrahydro-9H-pyrido[3,4b]-indole

Yield: 19%

Melting Point: 310.9° C.

6-fluoro-1,2,3,4-tetrahydro-9H-pyrido[3,4b]-indole

Yield: 38%

Melting Point: 316.6° C.

Yield: 54%

Melting Point: 330° C.

Elemental Analysis: C 65.75; H 7.29; N 11.62.

EXAMPLE 76

7-methyl-8-chloro-1,2,3,4-tetrahydro-9H-pyrido[3,4b]-indole

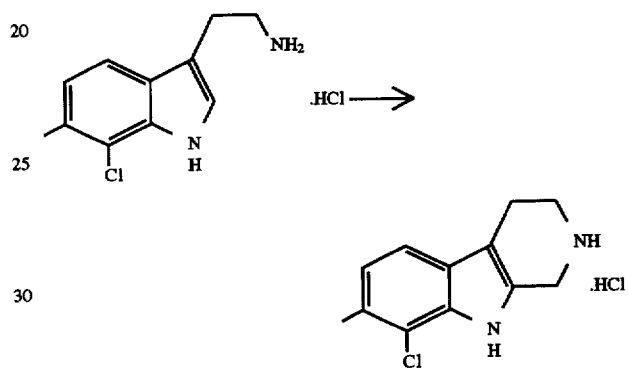

The desired product was prepared using the process substantially as described in Example 1 except that the starting material was 6-methyl-7-chloro-1H-indole-3-ethanamine hydrochloride.

Yield: 70%

The resulting material was boiled in ethanol. The resulting product was collected, washed with ethanol, and vacuum dried.

Yield: 58%

Melting Point: 330°–334° C.

Elemental Analysis: C 55.88; H 5.47; N 10.93.

The following were prepared using the process substantially as described above in Example 76.

7-methyl-8-chloro-1,2,3,4-tetrahydro-9H-pyrido[3,4b]-indole

Melting Point: 350°–352° C.

Elemental Analysis: C 55.65; H 5.68; N 10.39.

8-chloro-1,2,3,4-tetrahydro-9H-pyrido[3,4b]-indole

Melting Point: 335°–337° C.

Elemental Analysis: C 53.93; H 4.88; N 11.09.

7-bromo-8-methyl-1,2,3,4-tetrahydro-9H-pyrido[3,4b]-indole

Melting Point: 323°–325° C.

Elemental Analysis: C 47.85; H 4.84; N 9.08.

EXAMPLE 77

7-methyl-1,2,3,4-tetrahydro-9H-pyrido[3,4b]-indole

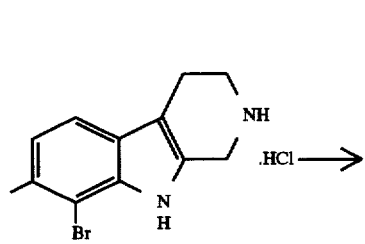

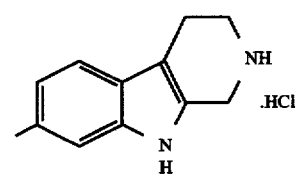

A sample of 7-methyl-8-bromo-1,2,3,4-tetrahydro-9H-pyrido[3,4b]-indole was reacted with hydrogen in the presence of Pd/C, ethanol, and triethylamine. The resulting material was filtered, concentrated and extracted. The organic phase was dried, concentrated, and vacuum dried. The resulting solid was taken up into methanol and added to ethereal HCl. A white solid was collected, washed with Et₂O, and vacuum dried.

Yield: 56%

Melting Point: 310°–312° C.

Elemental Analysis: C 64.79; H 6.89; N 12.47.

EXAMPLE 78

8-methyl-1,2,3,4-tetrahydro-9H-pyrido[3,4b]-indole

The desired product was prepared using the process substantially as described in Example 77.

Yield: 46%

Melting Point: 318°–320° C.

Elemental Analysis: C 64.53; H 6.94; N 12.43.

EXAMPLE 79

7-bromo-1H-indole-3-ethanamine

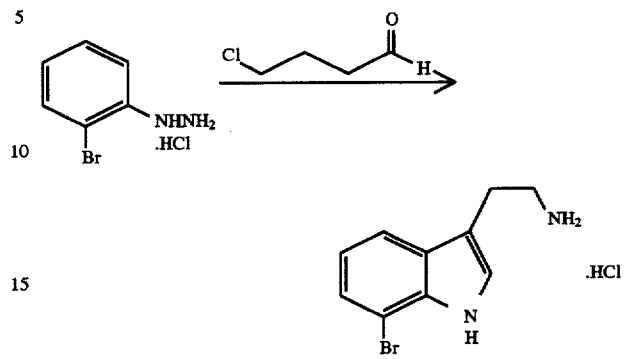

A 25.8 g sample of 2-bromophenylhydrazine hydrochloride was partitioned between 1N NaOH and chloroform. The organic layer was separated and the aqueous portion was extracted with chloroform. The combined organic extracts were dried (Na₂SO₄) and concentrated to yield the free hydrazine as an oil.

The oil was stirred in 100 mL of methanol while 4-chlorobutyraldehyde (12.3 g) was added. The resulting solution was transferred to a sealable tube and purged with nitrogen. The tube was sealed and the reaction mixture was heated in an oil bath maintained at 95° C. for 14 hours. The resulting mixture was allowed to cool and concentrated to a residue which was partitioned between 1N NaOH and chloroform. The combined organic extracts were dried and concentrated to an oil. The oil was chromatographed on silica gel using a gradient of 0–10% methanol in chloroform. Fractions containing product were concentrated to an oil which was taken up in a small amount of methanol and added to ethereal HCl. A solid was collected, washed with diethyl ether and vacuum dried at 50° C.

Yield: 7.32 g

Yield: 23%

M.P.: 260°–262° C.

Elemental Analysis: C 43.55: H 4.41: N 10.03.

EXAMPLE 80

7-fluoro-1H-indole-3-ethanamine

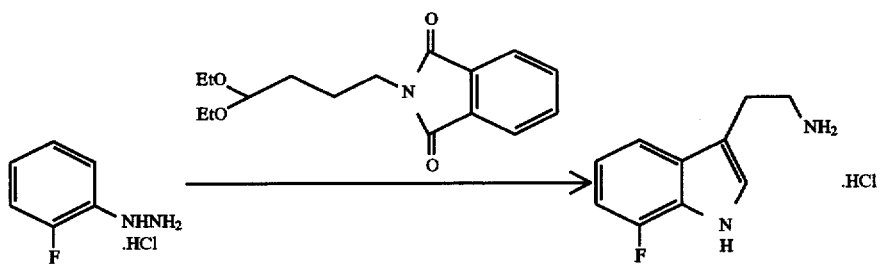

The desired 7-fluoro-1H-indole-3-ethanamine was prepared substantially as described in Example 81 infra. except that 2-fluorophenylhydrazine hydrochloride (25.5 g) was used. Additionally, reverse phase HPLC was required for final purification.

Yield: 4 g

Melting point: 187°–189° C.

Elemental Analysis: C 55.12; H 5.48; N 12.60.

EXAMPLE 81

7-methoxy-1H-indole-3-ethanamine

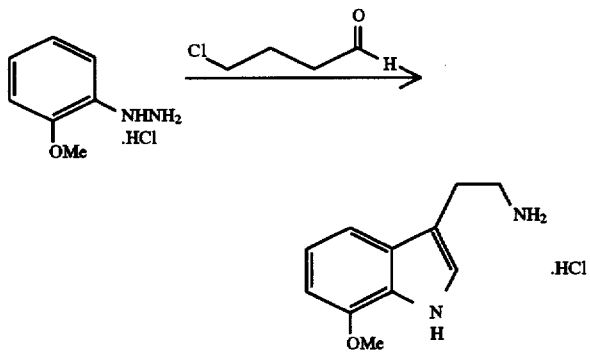

A 15.8 g sample of 2-methoxyphenylhydrazine hydrochloride and a 26.3 g sample of 4-phthalimidobutyraldehyde diethyl acetal were stirred in ethanol. The mixture was heated at reflux for 2 hours. The reaction mixture was allowed to cool and was concentrated to a residue.

The resulting residue was dissolved in 750 mL ethanol and 15.5 g hydrazine hydrate was added. The mixture was heated at reflux for 14 hours. A 70 mL sample of 5N HCl was added and the mixture was allowed to cool. The cooled mixture was concentrated to a residue. The residue was partitioned between 1N NaOH and chloroform. The organic portion was separated and the aqueous portion was extracted with chloroform. The combined organic extracts were dried (Na₂SO₄) and concentrated to an oil. The oil was chromatographed on silica gel using a gradient of 0–10% methanol in chloroform. Fractions containing product were concentrated to an oil which was taken up into a small amount of methanol and added to ethereal HCl. A solid was collected, washed with diethyl ether, and vacuum dried at 50° C. to afford a white solid.

Yield: 7.5 g (37%)

melting point: 198°–200° C.

Elemental Analysis: C 57.51; H 6.75; N 12.10.

EXAMPLE 82

7-chloro-1H-indole-3-ethanamine

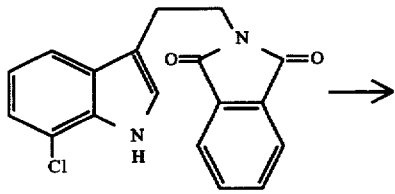

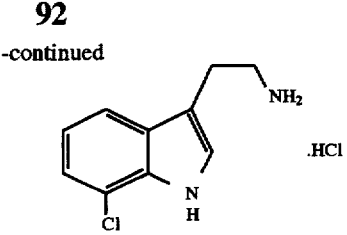

A 10.0 g sample of 2-chlorophenylhydrazine hydrochloride and 17.9 g of 4-phthalimidobutyraldehyde diethyl acetal were stirred in 200 mL ethanol with 1 mL 5N HCl. The mixture was concentrated to a residue which was slurried in a small amount of methylene chloride. A yellow solid was collected and vacuum dried at 40° C. The solid was stirred in 500 mL ethanol. Hydrazine hydrate (14 g) was added and the mixture was heated at reflux for 14 hours. A 60 mL sample of 5N HCl was added and the mixture was heated at reflux for 1 hour. The mixture was allowed to cool and was concentrated to a residue. The residue was partitioned between 1N NaOH and chloroform. The organic layer was separated and the aqueous layer was extracted with chloroform. The combined extracts were dried (Na₂SO₄) and concentrated to an oil. The oil was chromatographed on silica gel using a gradient of 0–10% methanol in chloroform containing 0.2% ammonium hydroxide. Fractions containing product were concentrated to an oil which was taken up in a small amount of methanol and added to ethereal HCl. A solid was collected, washed with diethyl ether, and vacuum dried at 50° C.

Yield: 3.2 g (25%)

Melting Point: 227°–229° C.

Elemental Analysis: C 51.76; H 5.29; N 11.97.

EXAMPLE 83

5-methyl-7-chloro-1H-indole-3-ethanamine

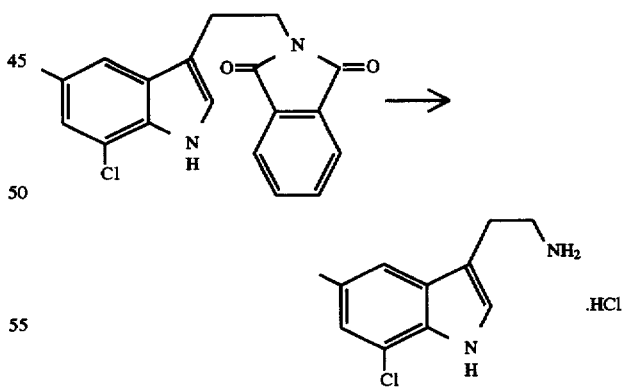

The desired product was prepared substantially as described in Example 82.

Yield: 4.3 g (34%)

Melting Point: 279°–281° C.

Elemental Analysis: C 54.05; H 5.85; N 11.33.

EXAMPLE 84

1-H-Benz(G)indole-3-ethanamine

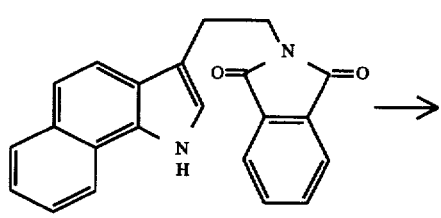

1-H-Benz(G)indole-3-ethanamine was prepared using substantially the process described in Example 82.

Yield: 3.5 g (17%)

Melting Point: 305°–307° C.

Elemental Analysis: C 68.43; H 6.30; N 11.08.

EXAMPLE 85

6-methyl-7-chloro-1H-indole-3-ethanamine6-bromo-7-methyl-1H-indole-3-ethanamine

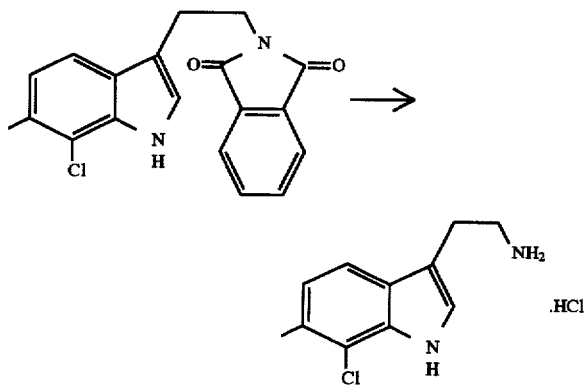

6-methyl-7-chloro-1H-indole-3-ethanamine was prepared using substantially the same process described in Example 82.

Yield: 3.0 g (24%)

Melting Point: 290° C.

Elemental Analysis: C 54.10; H 5.88; N 11.66.

6-bromo-7-methyl-1H-indole-3-ethanamine was prepared substantially as described in Example 82 using appropriate starting materials.

Yield: 1.6 g (56%)

Melting Point: 251° C.

Elemental Analysis: C 45.85; H 4.97; N 9.71.

EXAMPLE 86

6-methyl-1H-indole-3-ethanamine

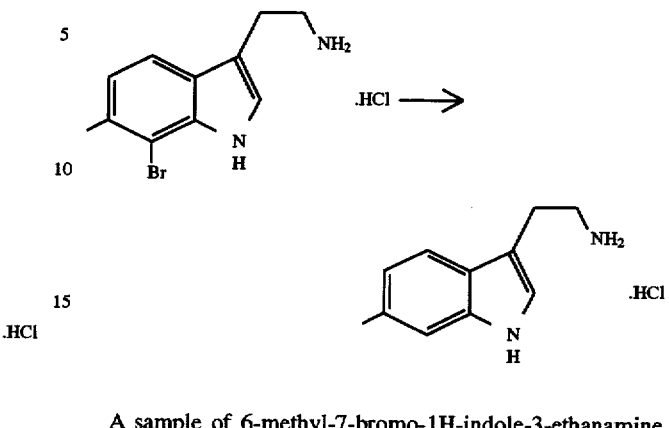

A sample of 6-methyl-7-bromo-1H-indole-3-ethanamine was contacted with Pd/C $H_2$ in the presence of ethanol and triethylamine. The resulting material was evaporated and partitioned between base/$CHCl_3$. The organic phase was dried, concentrated, and dried. The resulting material was taken up into methanol and added to ethereal HCl. The resulting material was washed and vacuum dried.

Melting Point: 232°–236° C.

Elemental Analysis: C 62.84; H 7.24; N 13.20.

EXAMPLE 87

5-methyl-7-bromo-1H-indole-3-ethanamine

A sample of 5-methyl-7-bromo-1H-indole-3-ethanamine was prepared using appropriate starting materials and substantially the process described in Example 79.

Yield: 16%

A 0.6 g sample of 5-methyl-7-bromo-1H-indole-3-ethanamine hydrochloride salt was converted to the free base and chromatographed on silica. The desired fractions were pooled and evaporated. The resulting material was taken up into ethyl acetate, filtered, diluted with ether, and maleic acid in methanol. The product was crystallized using ether, filtered, and dried.

Yield: 67%

Melting Point: 185°–187° C.

Elemental Analysis: C 49.09; H 4.85; N 7.71.

EXAMPLE 88

6,7-dimethyl-1H-indole-3-ethanamine

A sample of 6,7-dimethyl-1H-indole-3-ethanamine was prepared using appropriate starting materials and substantially the process described in Example 79. The 6,7-dimethyl-1H-indole-3-ethanamine was purified by treating with $K_2CO_3$ and extracting with 3:1 $CHCl_3$/isopropanol. The organic phase was dried, evaporated, and chromatographed. The desired fractions were pooled, evaporated, and mixed with ethyl acetate. The resulting material was diluted with ether and maleic acid in methanol. The solid was triturated in ether and dried.

Melting Point: 171°–173° C.

Elemental Analysis: C 63.20; H 6.75; N 8.98.

EXAMPLE 89

6-methyl-7-bromo-1H-indole-3-ethanamine

A sample of 6-methyl-7-bromo-1H-indole-3-ethanamine was prepared using appropriate starting materials and substantially the process described in Example 79.

Yield: 8.6%

The 6-methyl-7-bromo-1H-indole-3-ethanamine was dissolved in boiling ethanol and slowly cooled to room temperature. The solvent was reduced, the resulting material was filtered, and washed with ether. The resulting material was again filtered and washed with ether to afford the desired compound.

Melting Point: 288°–290° C.

Elemental Analysis: C 45.54; H 4.80; N 9.47.

For Examples 90 through 110, where applicable, diethylether was distilled from sodium benzophenone ketyl prior to use. All reactions were performed under a positive pressure of argon. $^1$H-NMR and $^{13}$C-NMR data were recorded on a Bruker AC-200P (200 MHz). IR spectra were obtained on Nicolet 510 P-FT (film and KBr). Melting points were determined on a Büchi apparatus and are not corrected. Analytical TLC was performed on Merck TLC glass plates precoated with $F_{254}$ silica gel 60 (UV, 254 nm and Iodine). Chromatographic separations were performed by using 230–400 mesh silica gel (Merck). N-BOC-aziridines (2a–d) were prepared from the corresponding alkenes following standard procedures.

Preparation 2

Indole starting materials

The indole starting materials (1a, 1b, and 1c) infra. were purchased (1a), prepared according to Bartoli's procedure (1b) [Bartoli, G. et al. *Tetrahedron Lett.*, 1989, 30, 2129] or (1c) synthesized from 2-iodo-4,6-dimethylaniline (5'''). The process is illustrated by the following Scheme:

Scheme IV

The 2-Iodo-4,6-dimethylaniline (5''') synthesis can be completed as follows: To a suspension of 5''' (24 mmol.), CuI (0.05 equiv.) and (PPh$_3$)$_2$PdCl$_2$ (0.05 equiv.) in 30 ml of dry triethylamine under Ar atmosphere was added trimethylsilylacetylene (1.1 equiv.) and the resulting mixture was stirred for 3 hours. Then, the solvent was eliminated under vacuum and the residue purified by flash chromatography using hexane/ethyl acetate (3:1) as eluent to yield 6''' in quantitative yield. A slurry of 6''' (23 mmol.) and CuI (2 equiv.) in 50 ml of dry dimethylformamide was heated for 2.5 h. under Ar atmosphere at 100° C. After cooling down to room temperature the reaction mixture was filtered off and the solid washed twice with ether (20 ml.). The organic phase was washed with water (3×50 ml.), dried over Na$_2$SO$_4$ and the solvent evaporated to dryness. The crude product was purified by flash chromatography using hexane/ethyl acetate (3:1) as eluent to afford 1c (1.5 g., 45%).

The process for preparing compounds of Examples 90 through 107 is illustrated by the following Scheme:

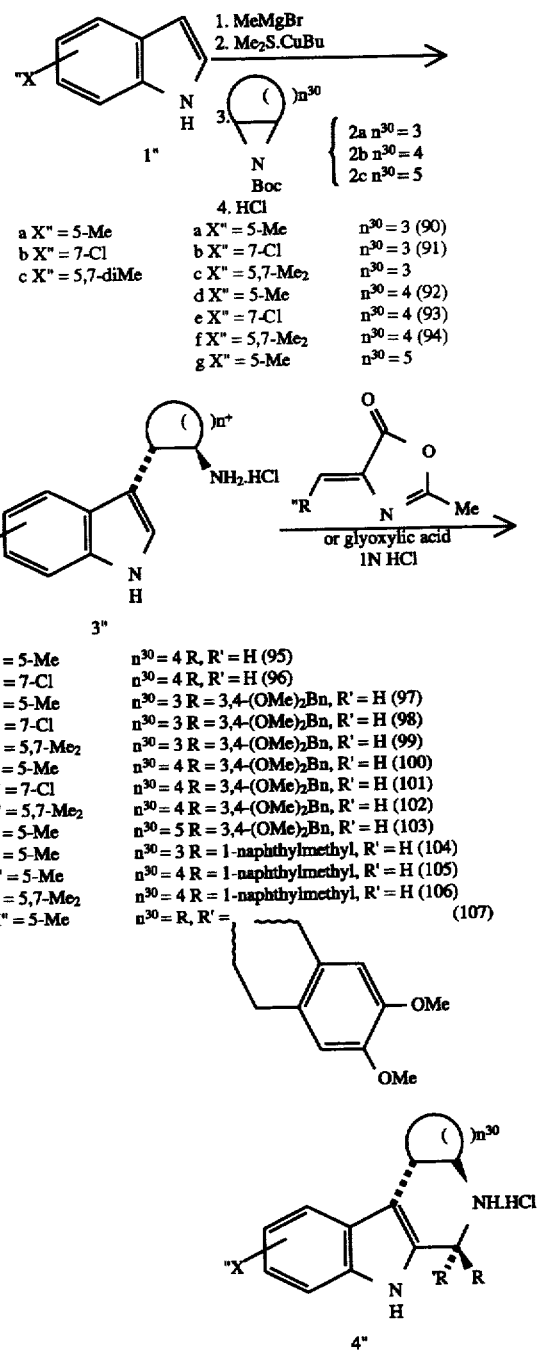

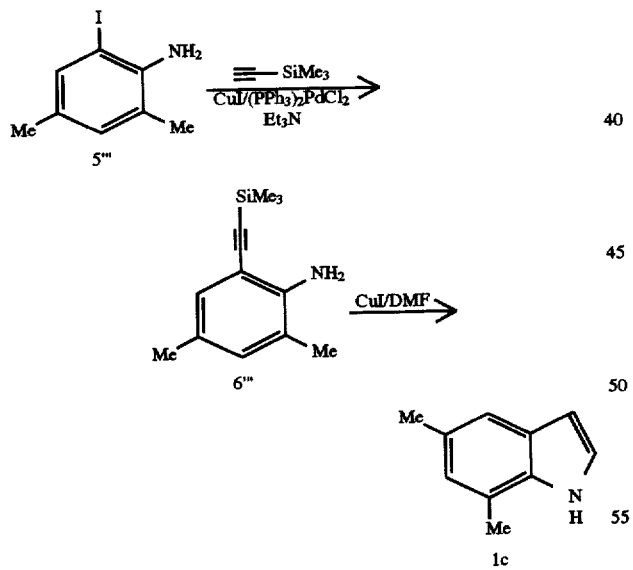

EXAMPLE 90

Trans-3-(2-amino-cyclopentyl)-5-methylindole, hydrochloride

To a suspension of the corresponding indole 1a (5 mmol.) in 10 ml of anhydrous ether under Ar atmosphere was added a 3M solution of methylmagnesium bromide (1.5 equiv.). The resulting mixture was stirred for 45 min. at room temperature. Then, this mixture was cannulated to a slurry of Copper (I) bromide-dimethylsulfide complex (0.2 equiv.) in 5 ml. of dry ether under Ar atmosphere at −30° C. The reaction mixture was stirred for 30 min. at the same temperature. After this time the mixture was cooled down to −78° C. and the corresponding aziridine 2a (1.5 equiv.) dissolved in 10 ml. of dry ether was added. The whole mixture was allowed to reach room temperature and stirring was kept overnight. The reaction was quenched with 10 ml. of a saturated solution of ammonium chloride. The layers were separated and the aqueous phase was extracted with ether/ethyl acetate (1:1) (2×10 ml.). The combined organic extracts were dried over anhydrous sodium sulfate, the solvent was eliminated under vacuum and the residue was purified by flash chromatography using hexane/ethyl acetate (3:1). The corresponding N-BOC protected tryptamine was dissolved in dichloromethane/ether. The solution was saturated with dry hydrogen chloride and stirred overnight at room temperature. Finally, the solvent was evaporated and the crude title tryptamines purified by washing with dichoromethane/ether/methanol mixture (2:3:1). The product was identified as the title compound (3a).

Yield: 85%. Mp: >200° C. $^1$H NMR (CD$_3$OD), δ: 7.35 (s, 1H), 7.23–7.12 (m, 2H), 6.91 (d, J=7.5 Hz, 1H), 3.73 (m, 1H), 3.27 (m, 1H), 2.38–2.10 (m, 5H), 2.05–1.70 (m, 4H). $^{13}$C NMR (CD$_3$OD), δ: 136.98, 128.93, 127.84, 124.27, 123.13, 119.01, 114.19, 112.37, 58.56, 43.93, 33.10, 31.30, 23.07, 21.73. IR (KBr): 3304, 2963, 1593, 1510, 1481, 800 cm$^{-1}$. MS (EI): 214 (M$^+$-HCl, 28), 197 (70), 170 (14), 144 (42), 126 (49), 105 (33), 84 (100).

EXAMPLE 91

Trans-3-(2-amino-cyclopentyl)-7-chloroindole, hydrochloride

The title compound (3b) was prepared using substantially the same procedure as described by Example 90; however, the indole starting material was a compound of Formula 1b.

Yield: 37%. Mp: >200° C. $^1$H NMR (CD$_3$OD), δ: 7.56 (d, J=7.7 Hz, 1H), 7.31 (s, 1H), 7.12 (d J=7.3 Hz, 1H), 7.01 (t, J=7.8 Hz, 1H), 3.77 (q, J=7.9 Hz, 1H), 3.40–3.25 (m, 1H), 2.40–2.15 (m, 2H), 2.05–1.70 (m, 4H). $^{13}$C NMR (CD$_3$OD), δ: 135.48, 129.53, 124.28, 122.13, 120.79, 118.40, 118.02, 116.18, 58.55, 43.79, 33.32, 31.36, 23.11. IR (KBr): 3422, 3298, 3040, 2972, 2909, 1495 cm$^{-1}$. MS (EI): 235 (M$^+$-Cl, 100), 218 (28), 165 (7).

EXAMPLE 92

Trans-3-(2-amino-cyclohexyl)-5-methylindole, hydrochloride

The title compound (3d) was prepared using substantially the same procedure as described by Example 90.

Yield: 80%. Mp: >200° C. $^1$H NMR (CD$_3$OD), δ: 7.44(s, 1H), 7.27 (d, J=8.3 Hz, 1H), 7.18 (s, 1H), 6.95 (dd, J=8.3 and 1.2 Hz, 1H), 3.55–3.40 (m, 1H), 2.86 (dt, J=4.3 and 11.3 Hz, 1H), 2.42 (s, 3H), 2.25–2.12 (m, 1H), 2.10–1.79 (m, 4H), 1.75–1.40 (m, 3H). $^{13}$C NMR (CD$_3$OD), δ: 136.97, 129.12, 127.74, 124.42, 123.73, 119.09, 114.77, 112.48, 56.22, 41.61, 34.75, 32.42, 26.93, 25.79, 21.73. IR (KBr): 3400, 3283, 3021, 2936, 2861, 1491 cm$^{-1}$. MS (EI): 229 (M$^+$-Cl, 100).

EXAMPLE 94

Trans-3-(2-amino-cyclohexyl)-7-chloroindole, hydrochloride (3e)

The title compound (3e) was prepared using substantially the same procedure as described by Example 90.

Yield: 43%. Mp: >200° C. $^1$H NMR (CD$_3$OD), δ: 7.63 (d, J=7.8 Hz, 1H), 7.35 (s, 1H), 7.14 (d, J=7.4 Hz, 1H), 7.02 (t, J=7.7 Hz, 1H), 3.60–3.40 (s, 1H), 3.08–2.91 (m, 1H), 2.30–2.10 (m, 1H), 2.05–1.80 (m, 4H), 1.75–1.45 (m, 3H). $^{13}$C NMR (CD$_3$OD), δ: 135.43, 129.41 125.00, 122.15, 120.87, 118.53, 118.09, 116.70, 56.12, 41.43, 34.74, 32.37, 26.80, 25.68. IR (KBr): 2938, 2859, 1429, 1341, 779, 735 cm$^{-1}$. MS (EI): 249 (M$^+$-Cl, 100).

EXAMPLE 94

Trans-3-(2-amino-cyclohexyl)-5,7-dimethylindole, hydrochloride

Trans-3-(2-amino-cyclopentyl)-5,7-dimethylindole, hydrochloride

The title compound (3f) was prepared using substantially the procedure of Example 90; however, the indole was 1c and the aziridine was 2b.

Yield: 45%. Mp: >200° C. $^1$H NMR (CD$_3$OD), δ: 7.27 (s, 1H), 7.19 (s, 1H), 6.77 (s, 1H), 3.42 (dt, J=11.0 and 4.2 Hz, 1H), 2.85 (dt, J=11.4 and 4.2 Hz, 1H), 2.44 (s, 3H), 2.39 (s, 3H), 2.30–2.10 (m, 1H), 2.08–1.83 (m, 4H), 1.70–1.40 (m, 3H). $^{13}$C NMR (CD$_3$OD), δ: 136.39, 129.37, 127.39, 125.01, 123.56, 121.94, 116.78, 115.16, 56.28, 41.70, 34.71, 32.40, 26.93, 25.80, 21.72, 16.93. IR (KBr): 3420, 3279, 3013, 2934, 2861, 1505 cm$^{-1}$. MS (EI): 242 (M$^+$-HCl, 62), 225 (25), 199 (23), 184 (20), 171 (38), 158 (100), 145 (18), 128 (12), 115 (12), 97 (12).

Substantially the same procedure was used to prepare Trans-3-(2-amine-cyclopentyl)-5,7-dimethylindole, hydrochloride (3c); however, the aziridine was 2a.

Yield: 63%. $^1$H NMR (DMSO-d$_6$), δ: 10.8 (s, 1H), 8.12 (broad s, 3H), 7.30–7.20 (m, 2H), 6.70 (s, 1H), 3.70–3.55 (m, 1H), 3.55–3.20 (m, 1H), 2.38 (s, 3H), 2.36 (s, 3H), 2.30–2.10 (m, 2H), 2.00–1.60 (m, 4H).

EXAMPLE 95

Trans-10-methyl-2,3,4,4a,5,6,7,11c-octahydro-1H-indolo[2,3-c]quinoline, hydrochloride A suspension of tryptamine hydrochloride (3a) (1.3 mmol.) in 10 ml. of distilled water was dissolved by heating. To this solution glyoxylic acid (1.43 mmol.) in 1 ml. of water was added. Subsequently, a solution of KOH (1.3 mmol.) in 1 ml. of distilled water was slowly added to reach pH=4. The resulting solution was stirred at room temperature for 1 h. After this time, commercially available hydrochloric acid (0.5 ml.) was added dropwise and the resulting mixture was refluxed for 30 min. Another portion of hydrochloric acid (0.5 ml.) was added and the reaction further refluxed for 15 min. Finally, the reaction mixture was cooled down to room temperature and filtered off. The title tetrahydro-b-carboline (4a) was subsequently washed with water and ethanol.

Yield: 81%. Mp: >200° C. $^1$H NMR (DMSO-d$_6$), δ: >11.0 (s, 1H),9.92 (broad s, 1H), 9.68 (broad s, 1H), 7.38 (s, 1H), 7.23 (d, J=8.3 Hz, 1H), 6.88 (d, J=7.8 Hz, 1H), 4.50–4.22 (m, 2H), 3.18–2.95 (m, 2H), 2.80–2.65 (m, 1H) 2.34 (s, 3H), 2.30–2.15 (m, 1H), 1.98–1.80 (m, 2H), 1.80–1.20 (4H). $^{13}$C NMR (DMSO-d$_6$), δ: 134.75 127.31, 126.49, 125.64, 122.65, 119.11, 111.14, 108.82, 58.99, 37.18, 29.42, 28.84, 24.94, 24.43, 21.28. IR (KBr): 3391, 3266, 2936, 2861, 2801, 2762 cm$^{-1}$. MS (EI): 241 (M$^+$-Cl, 100).

EXAMPLE 96

Trans-8-chloro-2,3,4,4a,5,6,7,11c-octahydro-1H-indolo[2,3-c]quinoline, hydrochloride (4b)

A suspension of tryptamine hydrochloride (3b) (1.3 mmol.) in 10 ml. of distilled water was dissolved by heating.

To this solution glioxylic acid (1.43 mmol.) in 1 ml. of water was added. Subsequently, a solution of KOH (1.3 mmol.) in 1 ml. of distilled water was slowly added to reach pH=4. The resulting solution was stirred at room temperature for 1 h. After this time, commercially available hydrochloric acid (0.5 ml.) was added dropwise and the resulting mixture was refluxed for 30 min. Another portion of hydrochloric acid (0.5 ml.) was added and the reaction further refluxed for 15 min. Finally, the reaction mixture was cooled down to room temperature and filtered off. The title tetrahydro-b-carboline (4b) was subsequently washed with water and ethanol.

Yield: 45%. Mp: >200° C. $^1$H NMR (DMSO-$d_6$), δ: >11.0 (s, 1H), 10.05 (broad s, ]H), 9.87 (broad s, 1H), 7.58 (d, J=7.8 Hz, 1H), 7.16 (d, J=7.6 Hz, 1H), 6.98 (t, J=7.9 Hz, 1H), 4.60–4.20 (m, 2H), 3.18–2.95 (m, 2H), 2.90–2.70 (m, 1H), 2.25–2.18 (m, 1H), 1.98–1.75 (m, 2H), 1.65–1.20 (4H). $^{13}$C NMR (DMSO-$d_6$), δ: 133.17 128.18, 127.23, 120.65, 120.03, 118.55, 115.78, 110.73, 58.74, 36.93, 29.16, 28.77, 24.88, 24.36. IR (KBr): 3422, 3231, 2936, 2861, 2760, 1429 cm$^{-1}$. MS (EI): 261 (M$^+$-Cl, 30), 241 (100).

EXAMPLE 97

Trans-5-(3,4-dimethoxybenzyl)-9-methyl-1,2,3,4,4a, 5,6,10c-octahydrocyclopenta[a]pyrido[3,4-b]indole, hydrochloride (4c)

A suspension of the corresponding tryptamine hydrochloride (3a) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 88%. Mp: 187°–191° C. $^1$H NMR (DMSO-$d_6$), δ: >11.0 (s, 1H), 10.38 (broad s, 1H), 9.25 ( broad s, 1H), 7.50–7.15 (m, 3H), 7.15–6.80 (m, 3H), 5.0–4.70 (broad s, 1H), 3.75 (s, 6H), 3.40–2.80 (m), 2.49 (s, 3H), 2.20–1.70 (m, 4H), 1.55–1.30 (broad s, 1H). $^{13}$C NMR (DMSO-$d_6$), δ: 148.73 147.90, 134.45, 130.24, 128.17, 127.64, 125.44, 123.03, 121.78, 118.43, 113.69, 111.95, 111.27, 110.64, 62.01, 57.50, 55.51, 37.49, 25.52, 25.14, 21.30, 20.73. IR (KBr): 3438, 3237, 2942, 1518, 1264, 1248 cm$^{-1}$. MS (EI): 377 (M$^+$-Cl, 100).

EXAMPLE 98

Trans-7-chloro-5-(3,4-dimethoxybenzyl)-1,2,3,4,4a, 5,6,10c-octahydrocyclopenta[a]pyrido[3,4-b]indole, hydrochloride (4d)

A suspension of the corresponding tryptamine hydrochloride (3b) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 52%. Mp: >230° C. dec. $^1$H NMR (DMSO-$d_6$), δ: >11.0 (s, 1H), 10.40 (broad s, 1H), 9.30 (broad s, 1H), 7.60–7.42 (m, 1H), 7.38–6.90 (m, 5H), 4.90–4.75 (broad s, 1H), 3.78 (s, 3H), 3.76 (s, 3H), 3.40–3.00 (m), 2.15–1.80 (m, 4H), 1.60–1.35 (broad s, 1H). $^{13}$C NMR (DMSO-$d_6$), δ: 148.70, 147.91, 132.95, 131.78, 128.25, 127.02, 121.75, 121.11, 120.41, 117.96, 116.05, 113.54, 112.72, 111.99, 61.74, 57.45, 55.50, 37.27, 25.24, 25.07, 20.77. IR (KBr): 3588, 3438, 1518, 1290 cm$^{-1}$. MS (EI): 398 (M$^+$+2-HCl, 40), 396 (M$^+$-HCl, 100).

EXAMPLE 99

Trans-5-(3,4-dimethoxybenzyl)-7,9-dimethyl-1,2,3, 4,4a,5,6,10c-octahydrocyclopenta[a]pyrido[3,4-b] indole, hydrochloride (4e)

A suspension of the corresponding tryptamine hydrochloride (3c ) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 87%. Mp: >200° C. $^1$H NMR (DMSO-$d_6$), δ: >11.0 (s, 1H), 10.20 (broad s, 1H), 9.20 (broad s, 1H), 7.29 (s, 1H), 7.20–6.95 (m, 3H), 6.75 (s, 1H), 4.90–4.70 (broad s, 1H), 3.78 (s, 6H), 3.30–2.90 (m), 2.48 (s, 3H), 2.34 (s, 3H), 2.10–1.70 (m, 4H), 1.60–1.30 (broad s, 1H). $^{13}$C NMR (DMSO-$d_6$), δ: 148.73 147.90, 134.01, 129.98, 128.31, 127.84, 125.10, 123.82, 121.75, 120.42, 116.03, 113.58, 111.99, 111.21, 61.94, 57.62, 55.52, 37.60, 25.57, 25.17, 21.23, 20.75, 17.07. IR (KBr): 3447, 2910, 1520 cm$^{-1}$. MS (EI): 391 (M$^+$-Cl,100), 239 (35).

EXAMPLE 100

Trans-6-(3,4-dimethoxybenzyl)-10-methyl-2,3,4,4a, 5,6,7,11c-octahydro-1H-indolo[2,3-c]quinoline, hydrochloride (4f)

A suspension of the corresponding tryptamine hydrochloride (3d) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 85%. Mp: 197°–200° C. $^1$H NMR (DMSO-$d_6$), δ: >11.0 (s, 1H), 8.90 (broad s, 1H), 7.42 (s, 1H), 7.28 (d, J=8.3 Hz, 1H), 7.16 (s, 1H), 7.05–6.90 (m, 3H), 4.95–4.80 (broad s, 1H), 3.73 (s, 6H), 3.66–3.59 (m, 1H), 3.25–2.80 (m, 4H), 2.35 (s, 3H), 2.20–2.10 (m, 1H), 1.95–1.20 (m, 6H). $^{13}$C NMR (DMSO-$d_6$), δ: 148.67 147.91, 134.92, 134.76, 129.72, 127.85, 127.45, 125.43, 122.91, 121.85, 119.43, 113.59, 111.90, 111.30, 109.45, 59.98, 55.47, 55.40, 37.08, 36.65, 29.48, 28.24, 24.94, 24.41, 21.32. IR (KBr): 3439, 2936, 1516, 1464, 1453, 1265 cm$^{-1}$. MS (EI): 391 (M$^+$-Cl, 100).

EXAMPLE 101

Trans-8-chloro-6-(3,4-dimethoxybenzyl)-2,3,4a,5,6, 7,11c-octahydro-1H-indolo[2,3-c]quinoline, hydrochloride (4g)

A suspension of the corresponding tryptamine hydrochloride (3e) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 47%. Mp: >250° C. $^1$H NMR (DMSO-$d_6$), δ: >11.0 (s, 1H), 9.75 (broad s, 1H), 8.90 (broad s, 1H), 7.64 (d, J=7.9

Hz, 1H), 7.20 (d, J=7.8 Hz 1H), 7.15–7.00 (m, 4H), 4.90–4.80 (broad s, 1H), 3.74 (s, 6H), 3.70–3.60 (m, 1H), 3.25–2.85 (m, 4H), 2.20–2.15 (m, 1H), 1.95–1.25 (m, 6H). $^{13}$C NMR (DMSO-$d_6$), δ: 148.72, 148.00, 133.46, 131.35, 128.00, 127.08, 121.86, 121.13, 120.28, 119.01, 115.99, 113.41, 111.98, 111.66, 59.62, 55.53, 55.42, 54.98, 37.24, 36.49, 29.23, 28.25, 24.88, 24.34. IR (KBr): 3428, 2938, 1518, 1250 cm$^{-1}$. MS (EI): 410 (M$^+$-HCl, 100).

EXAMPLE 102

Trans-6-(3,4-dimethoxybenzyl)-8,10-dimethyl-2,3,4a,5,6,7,11c-octahydro-1H-indolo[2,3-]quinoline, hydrochloride (4h)

A suspension of the corresponding tryptamine hydrochloride (3f) (1 mmol) and the correponding 4-alkylidene-2-methyloxazolin-5-one (1.2 mmol) in 1N hydrochloric acid (3 mL.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 78%. Mp: 198°–202° C. $^1$H NMR (DMSO-$d_6$), δ: 10.88 (s, 1H), 9.81 (broad s, 1H), 8.78 (broad s, 1H), 7.24 (s, 1H), 7.20 (s, 1H), 7.10–6.90 (m, 2H), 6.73 (s, 1H), 4.90–4.75 (broad s, 1H), 3.74 (s, 6H), 3.25–3.10 (m, 2H), 3.10–2.80 (m, 2H), 2.45 (s, 3H), 2.32 (s, 3H), 2.20–2.10 (m, 1H), 2.00–1.80 (m, 3H), 1.60–1.10 (m, 3H). $^{13}$C NMR (DMSO-$d_6$), δ: 148.65 147.87, 134.44, 129.55, 128.17, 127.59, 125.13, 123.68, 121.90, 120.36, 117.05, 113.64, 111.89, 110.04, 59.89, 55.78, 55.41, 37.17, 36.56, 29.47, 28.21, 24.94, 24.43, 21.26, 17.09. IR (KBr): 3450, 2936, 1516, 1493, 1264, 1240 cm$^{-1}$. MS (EI): 405 (M$^+$-Cl,100).

EXAMPLE 103

Trans-7-(3,4-dimethoxybenzyl)-11-methyl-1,2,3,4,5,5a,6,7,8,12a-decahydrocyclohepta[a]pyrido[3,4-b]indole, hydrochloride A suspension of the corresponding tryptamine hydrochloride (3g) (1 mmol) and the correponding 4-alkylidene-2-methyloxazolin-5-one (1.2 mmol) in 1N hydrochloric acid (3 mL.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 35%. Mp: 187°–190° C. $^1$H NMR (DMSO-$d_6$), δ: >11.0 (s, 1H), 9.66 (broad s, 1H), 7.29–7.25 (m, 2H), 6.92 (d, J=7.8 Hz, 1H), 6.81 (d, J=8.2 Hz, 1H), 6.65–6.56 (m, 2H) 4.80–4.70 (broad s, 1H), 3.66 (s, 3H), 3.43 (s, 3H), 3.00–2.90 (m, 1H), 2.90–2.70 (m, 1H), 2.35 (s, 3H), 2.35–2.20 (m, 1H), 1.80–1.30 (m, 8H), 0.85–0.65 (m, 1H). $^{13}$C NMR (DMSO-$d_6$), δ: 148.56 147.96, 135.12, 128.81, 128.05, 127.27, 125.32, 123.09, 121.73, 118.97, 113.32, 111.85, 111.31, 110.51, 55.60, 55.08, 54.97, 51.48, 36.97, 36.24, 32.74, 31.88, 26.37, 24.88, 24.14, 21.30. IR (KBr): 3414, 3343, 2932, 2859, 1516, 1265 cm$^{-1}$. MS (EI): 405 (M$^+$-Cl, 100), 335 (20).

EXAMPLE 104

Trans-9-methyl-5-(1-naphthylmethyl)-1,2,3,4a,5,6,10c-octahydrocyclopenta[a]pyrido[3,4-b]indole, hydrochloride (4j)

A suspension of the corresponding tryptamine hydrochloride (3a) (1 mmol) and the correponding 4-alkylidene-2-methyloxazolin-5-one (1.2 mmol) in 1N hydrochloric acid (3 mL.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 78%. Mp: >200° C. $^1$H NMR (DMSO-$d_6$), δ: >11.0 (s, 1H), 10.45 (broad s, 1H), 9.03 (broad s, 1H), 8.46 (d, J=7.9 Hz, 1H), 8.12–7.90 (m, 3H), 7.70–7.40 (m, 3H), 7.40–7.25 (m, 2H), 6.96 (d, J=8.0 Hz, 1H), 5.15–4.90 (broad s, 1H), 4.45–4.30 (m, 1H), 3.65–3.50 (m), 3.15–2.95 (m, 1H), 2.38 (s, 3H), 2.00–1.70 (m, 4H), 1.60–1.35 (broad s, 1H). $^{13}$C NMR (DMSO-$d_6$), δ: 134.59,133.86, 131.63, 131.32, 129.92, 129.18, 128.86, 128.07, 127.74, 126.38, 125.96, 125.83, 125.48, 124.08, 123.20, 118.52, 111.31, 110.97, 61.78, 55.76, 37.40, 35.13, 25.49, 25.12, 21.32, 20.67. IR (KBr): 3445, 3231, 2949, 2878, 2780, 793 cm$^{-1}$. MS (EI): 367 (M$^+$-Cl, 100).

EXAMPLE 105

Trans-10-methyl-6-(1-naphthylmethyl)-2,3,4,4a,5,6,7,11c-octahydro-1H-indolo[2,3-c]quinoline, hydrochloride (4k)

A suspension of the corresponding tryptamine hydrochloride (3d) (1 mmol) and the correponding 4-alkylidene-2-methyloxazolin-5-one (1.2 mmol) in 1N hydrochloric acid (3 mL.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 80%. Mp: >200° C. $^1$H NMR (DMSO-$d_6$), δ: >11.0 (s, 1H), 8.40 (d, J=7.8 Hz, 1H), 8.01 (d, J=7.5 Hz, 1H), 7.92 (d, J=8.2 Hz, 1H), 7.74 (d, J=6.8 Hz, 1H), 7.70–7.40 (m, 4H), 7.35 (d, J=8.4 Hz, 1H), 6.97 (d, J=8.2 Hz, 1H), 5.15–4.90 (broad s, 1H), 4.50–4.30 (m, 1H), 3.50–3.10 (m, 2H), 3.10–2.82 (m, 2H), 2.38 (s, 3H), 2.10–1.20 (m, 7H). $^{13}$C NMR (DMSO-$d_6$), δ: 135.05,134.90, 133.85, 131.79, 131.28, 129.36, 128.93, 128.07, 127.56, 126.33, 125.94, 125.83, 125.41, 124.02, 123.10, 119.54, 111.27, 109.61, 59.72, 53.97, 36.73, 35.27, 29.47, 28.37, 24.92, 24.36, 21.34. IR (KBr): 3447, 3235, 2936, 2857, 1450, 790 cm$^{-1}$. MS (EI): 381 (M$^+$-Cl, 100).

EXAMPLE 106

Trans-8,10-dimethyl-6-(1-naphthylmethyl)-2,3,4,4a,5,6,7,11c-octahydro-1H-indolo[2,3-c]quinoline, hydrochloride (4l)

A suspension of the corresponding tryptamine hydrochloride (3f) (1 mmol) and the correponding 4-alkylidene-2-methyloxazolin-5-one (1.2 mmol) in 1N hydrochloric acid (3 mL.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 77%. Mp: >200° C. $^1$H NMR (DMSO-$d_6$), δ: >11.0 (s, 1H), 10.11 (broad s, 1H), 8.52 (d, J=8.2 Hz, 1H), 8.35 (broad s, 1H), 8.02 (d, J=7.3 Hz, 1H), 7.92 (d, J=7.9 Hz, 1H), 7.82 (d, J=6.9 Hz, 1H), 7.71–7.46 (m, 3H), 7.29 (s, 1H), 6.78 (s, 1H), 5.10–4.90 (broad s, 1H), 4.70–4.50 (m, 1H), 3.40–3.20 (m, 2H), 3.10–2.80 (m, 2H), 2.51 (s, 3H), 2.34 (s, 3H), 2.05–1.90 (m, 1H), 1.80–1.70 (m, 2H), 1.60–1.20 (m, 4H). $^{13}$C NMR (DMSO-$d_6$), δ: 134.57,133.87, 131.95, 131.42, 129.29, 129.11, 128.81, 128.04, 127.71, 126.21, 125.91, 125.83, 125.14, 124.46, 123.91, 120.46, 117.14, 110.25, 59.65, 54.03, 36.66, 35.25, 29.47, 28.32, 24.94, 24.35, 21.26, 17.30. IR (KBr): 3449, 2934, 2859, 2791, 1449, 779 cm$^{-1}$. MS (EI): 395 (M$^+$-Cl, 100).

EXAMPLE 107

Trans-spiro-6,6-[2-(3,4-dimethoxy)-1,2,3,4-tetrahydronaphthyl]-10-methyl-2,3,4,4a,5,6,7,11a-octahydro-1H-indolo[2,3-c]quinidine, hydrochloride (4m)

A suspension of the corresponding tryptamine hydrochloride (3a) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Epimeric mixture. Yield: 89%. $^1$H NMR (DMSO-d$_6$), δ: >11.0 (s, 1H), 10.12 (broad s, 1H), 8.72 (broad s, 1H), 7.42 (s, 1H), 7.21 (s, 1H), 6.90–6.60 (s, 3H), 3.75 (s, 3H), 3.71 (s, 3H), 3.30–2.80 (m, 5H), 2.35 (s, 3H), 2.00–1.20 (m, 6H). $^{13}$C NMR (DMSO-d$_6$), δ: 147.44, 134.84, 134.32, 133.98, 127.42, 126.53, 126.35, 125.25, 125.13, 123.60, 123.25, 122.98, 119.56, 119.43, 112.05, 111.48, 111.27, 108.78, 108.60, 57.83, 57.50, 56.07, 55.56, 36.40, 31.91, 30.74, 29.39, 29.21, 28.73, 28.41, 24.92, 24.38, 23.83, 21.30. IR (KBr): 3440, 2950, 1518, 1200, 1110, cm$^{-1}$. MS (EI): 417 (M$^+$-Cl, 100).

EXAMPLE 108

Trans-1-(3,4-dimethoxybenzyl)-3,4,6-trimethyl-1,2,3,4-tetrahydro-9H-pyrido[3,4-b]indole, hydrochloride (4n)

Trans-3-(2-amine-1,2-dimethylethyl)-5-methylindole, hydrochloride (3h) was prepared using substantially the procedure of Example 90; however, the aziridine was 2c.

Yield: 71%. $^1$H NMR (CD$_3$OD), δ: 7.45 (s, 1H), 7.32 (d, J=8.3 Hz, 1H), 7.19 (s, 1H), 7.00 (dd, J=8.4 and 1.5 Hz, 1H), 3.66 (t, J=6.9 Hz, 1H), 3.28 (t, J=7.3 Hz, 1H), 2.47(s, 3H), 1.48 (d, J=7.2 Hz, 3H), 1.38 (d, J=6.6 Hz, 3H). $^{13}$C NMR (CD$_3$OD), δ: 136.89, 129.19, 127.68, 124.46, 123.69, 119.09, 115.41, 112.44, 53.51, 36.62, 21.71, 17.06, 16.49.

A suspension of the corresponding tryptamine hydrochloride (3h) (1 mmol) and 6,7-dimethoxytetralin-2-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 32%. Mp: 195°–199° C. $^1$H NMR (DMSO-d$_6$), δ: >11.0 (s, 1H), 9.40 (broad s, 1H), 8.90 (broad s, 1H), 7.40 (s, 1H), 7.30 (d, J=8.2 Hz, 1H), 7.08 (s, 1H), 6.96–6.90 (m, 3H), 4.90–4.80 (broad s, 1H), 3.73 (s, 3H), 3.72 (s, 3H), 3.70–3.60 (m, 2H), 3.20–3.00 (m, 3H), 2.37 (s, 3H), 1.46 (broad s, 3H), 1.40 (broad s, 3H). $^{13}$C NMR (DMSO-d$_6$), δ: 148.66 147.93, 135.00, 129.21, 127.40, 125.40, 122.97, 121.82, 119.07, 113.56, 111.95, 111.24, 110.34, 57.32, 55.43, 55.33, 54.60, 36.46, 32.56, 21.24, 17.06, 15.92. IR (KBr): 3438, 2936, 1518, 1464, 1265, 1242, 1040 cm$^{-1}$. MS (EI): 365 (M$^+$-Cl, 100).

EXAMPLE 109

Cis-3-(2-amine-cyclohexyl)-5-methylindole, hydrochloride Cis-6-(3,4-dimethoxybenzyl)-10-methyl-2,3,4,4a,5,6,7,11c-octahydro-1H-indolo[2,3-c]quinoline, hydrochloride (4o)

The title compound (3i) was prepared following the procedure described by Scmuszkovicz, J. et al. Tetrahedron, 1991, 47, 8653 starting from 5-methylindole (1a).

Mp: 86°–90° C. $^1$H NMR (CD$_3$OD), δ: 7.38 (s, 1H), 7.26 (d, J=8.3 Hz, 1H), 7.11 (s, 1H), 6.96 (d, J=8.2, 1H), 3.90–3.70 (m, 1H), 3.55–3.38 (m, 1H), 2.42 (s, 3H), 2.40–2.35 (m, 1H), 2.10–1.79 (m, 4H), 1.75–1.50 (m, 3H). $^{13}$C NMR (CD$_3$OD), δ: 136.75, 129.27, 127.88, 124.63, 123.51, 118.71, 114.49, 112.34, 52.60, 36.79, 29.52, 26.44, 25.85, 21.68, 21.00. IR (KBr): 3401, 3017, 2932, 2863, 1561, 1489 cm$^{-1}$. MS (EI): 229 (M$^+$-Cl, 100).

The process for preparing the final product (4o) is illustrated by the following Scheme:

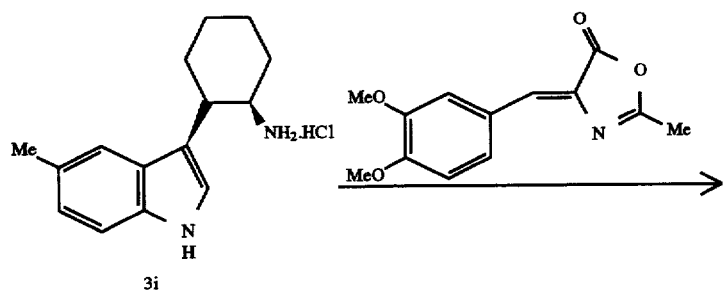

3i

-continued

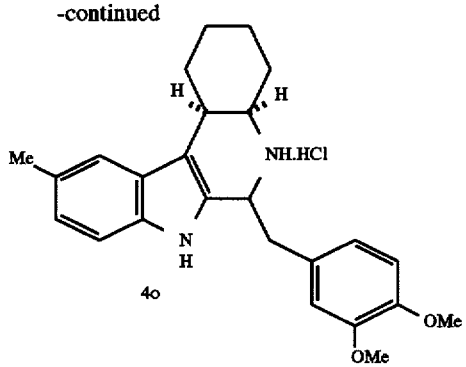

Mp: 167°–171° C. ¹H NMR (DMSO-d₆), δ: >11.0 (s, 1H), 8.87 (broad s, 2H), 7.29–7.20 (m, 3H), 7.12–6.85 (m, 3H), 4.95–4.80 (broad s, 1H), 3.76 (s, 3H), 3.75 (s, 3H), 3.70–3.60 (m), 3.25–3.00 (m, 1H), 2.36 (s, 3H), 2.40–2.00 (m), 1.95–1.20 (m, 6H). ¹³C NMR (DMSO-d₆), δ: 148.67 147.87, 134.80, 128.71, 128.43, 127.63, 125.45, 123.32, 121.75, 117.82, 113.59, 111.91, 111.30, 111.34, 56.99, 55.46, 55.12, 36.12, 36.65, 28.42, 27.49, 24.94, 24.39, 21.23, 19.17. IR (KBr): 3439, 2934, 1516, 1263 cm⁻¹. MS (EI): 390 (M⁺-ClH, 100).

As noted above, the compounds of the present invention are useful in blocking the effect of serotonin or other agonists at 5-HT$_{2A}$, 5-HT$_{2B}$ and/or 5-HT$_{1c}$ receptors. Thus, the present invention also provides a method for blocking 5-HT$_{2A}$, 5-HT$_{2B}$ or 5-HT$_{1c}$ receptors in mammals comprising administering to a mammal requiring blocking of a 5-HT$_{2A}$, 5-HT$_{2B}$, or 5-HT$_{1c}$ receptor, respectively, a receptor blocking dose of a compound of the invention.

One particularly useful embodiment of this invention is that it provides selective ligands for the 5-HT$_{2B}$ receptor. Compounds with a high affinity for the 5-HT$_{2B}$ receptor generally are cross-reactive with the 5-HT$_{2C}$ receptor as well. Now 5-HT$_{2B}$ receptors can be selectively modulated using compounds of this invention at rates set forth above for blocking the effects of agonists at 5-HT$_{2B}$ receptors. The selective affinity may provide treatments with fewer side effects and will facilitate the development of additional therapeutic agents.

Compounds exhibiting activity at the 5HT$_{2B}$ receptor are useful for treating disorders related to the modulation of the 5HT$_{2B}$ receptor. For example, compounds having 5HT$_{2B}$ antagonist activity reduce the spasticity of the colon. Thus, these compounds are useful for the treatment of functional bowel disorders including irritable bowel syndrome and irritable bowel syndrome-related symptoms. The antispasmodic effect of such compounds can reduce abdominal pain associated with functional bowel disorders. Additionally, the 5HT$_{2B}$ receptor is localized in other organs such as the brain, bladder, blood vessels, stomach, and uterus, indicating that additional conditions are 5HT$_{2B}$ mediated.

Compounds demonstrating activity at the 5HT$_{2A}$ receptor can be utilized in the treatment or prevention of conditions related to modulation of the 5HT$_{2A}$ receptor. Examples of such conditions include hypertension, sleep disorders, hallucinogenic activity, psychosis, anxiety, depression, thermoregulation, feeding disorders, and hypotension. Leonard, B. E., *International Clinical Psychopharmacology*, 7, 13–21 (1992).

The term "receptor blocking dose", means an amount of compound necessary to block a targeted receptor, selected from the group consisting of 5-HT$_{2A}$, 5-HT$_{2B}$, and 5-HT$_{1c}$ receptor in a mammal. The active compounds are effective over a wide dosage range. For example, dosages per day will normally fall within the range of about 0.05 to about 250 mg/kg of body weight. In the treatment of adult humans, the range of about 0.5 to 100 mg/kg, in single or divided doses, is preferred. The ranges of about 5 mg/kg to about 60 mg/kg and about 10 mg/kg to about 50 mg/kg are especially preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as oral, transdermal, subcutaneous, intranasal, intramuscular, and intravenous routes.

While it is possible to administer a compound of the invention directly without any formulation, the compounds are preferably employed in the form of a pharmaceutical formulation comprising a pharmaceutically acceptable excipient and at least one compound of the invention. Such compositions contain from about 0.1 percent by weight to about 90.0 percent by weight of a present compound. As such, the present invention also provides pharmaceutical formulations comprising a compound of the invention and a pharmaceutically acceptable excipient therefor.

In making the compositions of the present invention, the active ingredient is usually mixed with an excipient which can be a carrier, or a diluent or be diluted by a carrier, or enclosed within a carrier which can be in the form of a capsule, sachet, paper or other container. When the carrier serves as a diluent, it can be a solid, semi-solid, or liquid material which acts as a vehicle, excipient, or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

The compounds of the invention may be delivered transdermally, if desired. Transdermal permeation enhancers and delivery systems, including patches and the like, are well known to the skilled artisan.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxy-benzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The compounds of this invention may be delivered transdermally using known transdermal delivery systems and excipients. Most preferrably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier.

The active compounds are effective over a wide dosage range. For example, dosages per day will normally fall within the range of about 0.05 to about 250 mg/kg of body weight. In the treatment of adult humans, the range of about 0.5 to 100 mg/kg, in single or divided doses, is preferred. The ranges of about 5 mg/kg to about 60 mg/kg and about 10 mg/kg to about 50 mg/kg are especially preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as oral, transdermal, subcutaneous, intranasal, intramuscular, rectally, and intravenous routes.

Pharmaceutical compositions of a compound of the present invention or its salts or solvates are most preferrably produced by formulating an active compound in unit dosage form with a pharmaceutical carrier. Some examples of unit dosage forms are tablets, pills, powders, aqueous and non-aqueous oral solutions and suspensions, transdermal delivery devices and patches, and parenteral solutions packaged in containers containing either one or more unit dosages and may be capable of being subdivided into individual doses. Some examples of suitable pharmaceutical carriers and/or diluents include gelatin capsules, sugars including lactose and sucrose, starches such as corn starch and potato starch, cellulose derivatives such as sodium carboxymethyl cellulose, ethyl cellulose, methyl cellulose, and cellulose acetate phthalate, gelatin, talc, stearic acid, magnesium stearate, vegetable oils such as peanut oil, cottonseed oil, sesame oil, olive oil, corn oil, and oil of theobroma, propylene glycol, glycerin, sorbitol, polyethylene glycol, water, agar, alginic acid, isotonic saline, phosphate buffer solutions, lactic acid, glycolic acid, microcrystalline cellulose, kaolin, mannitol, dicalcium phosphate, sodium chloride, magnesium stearate, croscarmellose, alginic acid, sodium starch glycolate, lauryl sulfate, as well as other compatible substances used in pharmaceutical formulations. The active compound may be prepared as a microparticle using biodegradable polymers or other known methods. The composition may be prepared using known formulation technology to provide a rapidly dissolving, sustained release, or targeted delivery compositions. The compositions of this invnetion may contain other components such as coloring agents, flavoring, and/or preservatives. The compositions may contain other therapeutic agents, for example an antacid or analgesic.

The article of manufacture will include packaging material. Packaging material will preferably include a container. The preferred container and packaging material can be selected using the characteristics of the compound to be packaged. For example, the preferred container may be glass, plastic, foil, sealed bubble packaging, clear, amber, and may incorporate other known pharmaceutical packaging technology. The packaging may include features such as cotton, silica or other drying agents, and/or a measuring device. The article of manufacture shall include a label indicating that the composition is useful for the treatment of an a condition associated with 5-$HT_{2B}$ receptor stimulation malfunction. Most preferably, the condition is selected from the group consisting of urinary incontinence, bladder dysfunction, uterine dysfunction, cardiovascular disorder, and respiratory disorder.

In order to illustrate more fully the operation of this invention, the following formulation examples are provided. The examples are illustrative only, and are not intended to limit the scope of the invention. The formulations may employ as active compounds any of the compounds of the present invention.

Formulation 1

Hard gelatin capsules are prepared using the following ingredients:

| | Amount Per Capsule | Concentration by Weight (percent) |
|---|---|---|
| (+/−)6-ethyl-8-chloro-1-[(3,4-dimethoxyphenyl)methyl]-1,2,3,4-tetrahydro-9H-pyrido[3,4-b]indole hydrochloride | 250 mg | 55.0 |
| starch dried | 200 mg | 43.0 |
| magnesium stearate | 10 mg | 2.0 |
| | 460 mg | 100.0 |

The above ingredients are mixed and filled into hard gelatin capsules in 460 mg quantities.

Formulation 2

Capsules each containing 20 mg of medicament are made as follows:

|  | Amount Per Capsule | Concentration by Weight (percent) |
|---|---|---|
| 6-methyl-8-ethyl-1-[(3-bromo-4-chloro-phenyl)-methyl]-1,2,3,4-tetrahydro-9H-pyrido[3,4b]indole (Z)-2-butenedioate | 20 mg | 10.0 |
| starch | 89 mg | 44.5 |
| microcrystalline cellulose | 89 mg | 44.5 |
| magnesium stearate | 2 mg | 1.0 |
|  | 200 mg | 100.0 |

The active ingredient, cellulose, starch, and magnesium stearate are blended, passed through a No. 45 mesh U.S. sieve and filled into a hard gelatin capsule.

Formulation 3

Capsules each containing 100 mg of medicament are made as follows:

|  | Amount Per Capsule | Concentration by Weight (percent) |
|---|---|---|
| 5-fluoro-6-methyl-1-(1-(3-methylaminophenyl)-methyl)-1,2,3,4-tetrahydro-9H-pyrido-[3,4-b]indole(Z)-2-butenedioate | 100 mg | 30.00 |
| polyoxyethylene sorbitan monooleate | 50 mg | 0.02 |
| starch powder | 250 mg | 69.98 |
|  | 400 mg | 100.00 |

The above ingredients are thoroughly mixed and placed in an empty gelatin capsule.

Formulation 4

Tablets containing 10 mg of active ingredient are made as follows:

|  | Amount Per Capsule | Concentration by Weight (percent) |
|---|---|---|
| 6-fluoro-8-phenoxy-1-(1-(4-ethoxy-phenyl)-methyl)-1,2,3,4-tetrahydro-9H-pyrido-[3,4-b]indole(Z)-2-butenedioate | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |

|  | Amount Per Capsule | Concentration by Weight (percent) |
|---|---|---|
| magnesium stearate | 0.5 mg | 0.5 |
| talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formulation may be prepared using the ingredients below:

|  | Amount Per Capsule | Concentration by Weight (percent) |
|---|---|---|
| 5,6-difluoro-1-(1-(3-dimethylamino-phenyl)-methyl)-1,2,3,4-tetrahydro-9H-pyrido-[3,4-b]indole(Z)-2-butenedioate | 250 mg | 38.0 |
| microcrystalline cellulose | 400 mg | 60.0 |
| silicon dioxide fumed | 10 mg | 1.5 |
| stearic acid | 5 mg | 0.5 |
|  | 665 mg | 100.0 |

The components are blended and compressed to form tablets each weighing 665 mg.

Formulation 6

Suspensions each containing 5 mg of medicament per 5 ml dose are as follows:

|  | per 5 ml of suspension |
|---|---|
| 3-methyl-5-chloro-6-methyl-1-(1-(3-dimethylamino-phenyl)-methyl)-1,2,3,4-tetrahydro-9H-pyrido-[3,4-b]indole(Z)-2-butenedioate | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| | Concentration by Weight (percent) |
|---|---|
| 5-propyl-6-ethyl-1-[(3,4-dimethoxy-phenyl)-methyl]-1,2,3,4-tetrahydro-9H-pyrido-[3,4-b]indole hydrochloride | 0.25 |
| ethanol | 29.75 |
| Propellant 22 | 70.00 |
| (chlorodifluoromethane) | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

Formulation 8

Injectables may be prepared as follows:

| | Amount Per Batch |
|---|---|
| 6-(1-methylethyl)-1,2,3,4-tetrahydro-1-(1-(4-dimethylaminophthalenyl)-methyl)-9H-pyrido[3,4b]indole (Z)-2-butenedioate | 50 mg |
| Devazepide for Injection | q.s. |

The compound or a suitable salt thereof is dissolved in, for example, ethanol, and passed through a 0.2 micron filter. Aliquots of filtered solution are added to ampoules or vials, sealed and sterilized.

Formulation 9

Tablets containing 10 mg of active ingredient are made as follows:

| | Amount Per Tablet | Concentration by Weight (percent) |
|---|---|---|
| 7,8,9,10-tetrahydro-10-(1-(2-dimethyl-aminonaphthyleneyl)-methyl)-11H-benzo[g]-pyrido[3,4-b]indole (Z)-2-butenedioate | 6 g | 2.0 |
| corn starch | 200 g | 78.0 |
| microcrystalline cellulose | 46 g | 18.0 |
| Sterotex Powder HM | 4 g | 1.5 |
| Purified Water | 300 mL | |
| | 100 mg | 100.0 |

The active ingredient, starch and cellulose are combined together in a planetary mixer and mixed for 2 minutes. Water is added to the combination and mixed for 1 minute. The resulting mix is spread on trays and dried in a hot air oven at 50° C. until a moisture level of 1 to 2 percent is obtained. The dried mix then milled with a Fitzmill through a #RH2B screen, and added back to the milling mixture. The mixture is drum rolled for 5 minutes. Compressed tablets of 50 mg, 150 mg, and 200 mg are formed with appropriate sized punches.

Formulation 10

Capsules are prepared using the following ingredients:

| | Amount Per Capsule | Concentration by Weight (percent) |
|---|---|---|
| (+/−)6-methyl-1-(1-(3-ethylamino naphthalenyl)-1-ethyl)-1,2,3,4-tetrahydro-9H-pyrido[3,4-b]indole(Z) 2-butenedioate | 200 mg | 49.0 |
| lactose USP | 200 mg | 49.0 |
| Serotex Powder | 10 mg | 2.0 |
| | 410 mg | 100.0 |

The above ingredients are mixed and filled into hard gelatin capsules in 410 mg quantities.

Formulation 11

Hard gelatin capsules are prepared using the following ingredients:

| | Amount Per Capsule | Concentration by Weight (percent) |
|---|---|---|
| Trans-9-methyl-5-(1-naphthylmethyl)-1,2,3,4-4a,5,6,10c,octahydrocyclo-penta[a]pyrido[3,4-b]indole, hydrochloride | 250 mg | 55.0 |
| starch dried | 200 mg | 43.0 |
| magnesium stearate | 10 mg | 2.0 |
| | 460 mg | 100.0 |

The above ingredients are mixed and filled into hard gelatin capsules in 460 mg quantities.

Formulation 12

Capsules each containing 20 mg of medicament are made as follows:

| | Amount Per Capsule | Concentration by Weight (percent) |
|---|---|---|
| spiro-6,6[2-(3,5-dimethoxy)-1,2,3,4-tetrahydronaphthyl]-10-methyl-2,3,4,4a,5,6,7,11a-octahydro-1H-indolo[2,3-c]-quinuclidine, hydrochloride | 20 mg | 10.0 |
| starch | 89 mg | 44.5 |
| microcrystalline cellulose | 89 mg | 44.5 |
| magnesium stearate | 2 mg | 1.0 |
| | 200 mg | 100.0 |

The active ingredient, cellulose, starch, and magnesium stearate are blended, passed through a No. 45 mesh U.S. sieve and filled into a hard gelatin capsule.

Formulation 13

Capsules each containing 100 mg of medicament are made as follows:

|  | Amount Per Capsule | Concentration by Weight (percent) |
|---|---|---|
| spiro-6,6[2-(3-fluoro-4-methoxy)-1,2,3,4-tetrahydronaphthyl]-10-methyl-2,3,4,4a,5,6,7,11a-octahydro-1H-indolo[2,3-c]-quinuclidine, hydrochloride | 100 mg | 30.00 |
| polyoxyethylene sorbitan monooleate | 50 mg | 0.02 |
| starch powder | 250 mg | 69.98 |
|  | 350 mg | 100.00 |

The above ingredients are thoroughly mixed and placed in an empty gelatin capsule.

Formulation 14

Tablets containing 10 mg of active ingredient are made as follows:

|  | Amount Per Tablet | Concentration by Weight (percent) |
|---|---|---|
| 8-fluoro-10-phenoxy-6-(1-naphthylmethyl)-2,3,4,4a,5,6,7,11c-octahydro-1H-indolo-[2,3-c]quinoline, tartrate | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 15

A tablet formulation may be prepared using the ingredients below:

|  | Amount Per Tablet | Concentration by Weight (percent) |
|---|---|---|
| 8-methyl-10-methoxy-6-(1-naphthylethyl)-2,3,4,4a,5,6,7,11c-octahydro-1H-indolo-[2,3-c]quinoline | 250 mg | 38.0 |
| microcrystalline cellulose | 400 mg | 60.0 |
| silicon dioxide fumed | 10 mg | 1.5 |
| stearic acid | 5 mg | 0.5 |
|  | 665 mg | 100.0 |

The components are blended and compressed to form tablets each weighing 665 mg.

Formulation 16

Suspensions each containing 5 mg of medicament per 5 ml dose are as follows:

|  | per 5 ml of suspension |
|---|---|
| 8-chloro-10-cyclopropyl-6-(1-naphthylethyl)-2,3,4,4a,5,6,7,11c-octahydro-1H-indolo-[2,3-c]quinoline | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 17

An aerosol solution is prepared containing the following components:

|  | Concentration by Weight (percent) |
|---|---|
| spiro-6,6[2-(3-ethyl-4-ethoxy)-1,2,3,4-tetrahydronaphthyl]-10-methyl-2,3,4,4a,5,6,7,11a-octahydro-1H-indolo[2,3-c]-quinuclidine, maleate | 0.25 |
| ethanol | 29.75 |
| Propellant 22 | 70.00 |
| (chlorodifluoromethane) | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

115

Formulation 18

A tablet formulation may be prepared using the ingredients below:

| | Amount Per Tablet | Concentration by Weight (percent) |
|---|---|---|
| spiro-6,6[2-(3-ethyl-4-ethoxy)-1,2,3,4-tetrahydro-6-methyl-naphthyl]-10-methyl-2,3,4,4a,5,6,7,11a-octahydro-1H-indolo[2,3-c]-quinuclidine, maleate | 250 mg | 38.0 |
| microcrystalline cellulose | 400 mg | 60.0 |
| silicon dioxide fumed | 10 mg | 1.5 |
| stearic acid | 5 mg | 0.5 |
| | 665 mg | 100.0 |

The components are blended and compressed to form tablets each weighing 665 mg.

Compounds of the present invention were tested for 5-HT$_{1C}$ receptor affinity using the following procedure:

IA. Biological Reagent Preparation.

Beef brain was removed immediately after slaughter, and choroid plexus were dissected over ice. Male Sprague-Dawley rats weighing 125–150 g (Harlan Industries, Cumberland, Ind.) were killed by decapitation. The brain of each was immediately removed and the cerebral cortex was dissected over ice. Tissues were homogenized in 9 volumes of 0.32 mol/L sucrose and centrifuged at 1,000×g for 10 minutes. The supernatant was centrifuged at 17,000×g for 20 minutes. The pellet was suspended in 100 volumes of 50 mM Tris-HCl (pH7.4), incubated at 37° C. for 10 minutes and centrifuged at 50,000×g for 10 minutes, and the process was repeated three times. The final pellets were frozen at −70° C. and used within 2 weeks. Pellets were rehydrated with physiological buffer prior to use.

II. Assay Procedure.

Radioligand binding assays for 5-HT$_{1C}$ and 5-HT$_2$ receptors were conducted according to described methods. The assays can be conducted as described by Hoyer D., Functional correlates of serotonin 5-HT$_1$ recognition sites, *J. Receptor Res* 8, 59–81 (1988) and Hoyer D., Engel G., Kalkman H. O. *Molecular pharmacology* of 5-HT$_1$ and 5-HT$_2$ recognition sites in rat and pig brain membranes: Radio-ligand binding studies with [$^3$H]5-HT, [$^3$H]8-OH-DPAT, (−)[$^{125}$I]iodocyanopindolol, [$^3$H]mesulergine and [$^3$H]ketanserin, *Eur. J. Pharmacol.* 118, 13–23 (1985).

For 5-HT$_{1C}$ receptor assays increasing concentrations of experimental compound, 50 mM Tris HCl buffer pH 7.4, and tritiated mesulergine (2.0 nM) ($^3$H ligand) were combined in polystyrene tubes at room temperature. The reaction was initiated by the addition of the resuspended choroid plexus tissue which had been preincubated at 37° C. for 20 minutes. The reaction mixture was incubated in a 37° C. water bath for 15 minutes.

The reactions were terminated by rapid filtration, (Brandel Cell Harvestor), through Whatman GF/B glass filters that had been presoaked in Tris buffer pH 7.4. The filters were then washed 2 times with 5 ml of ice cold Tris buffer pH 7.4. Washed filters were placed in scintillation vials and 10 ml RedySolv, (Brandel), was added and samples were counted in a Searle D-300 beta counter. Means and standard error statistics were calculated for triplicate experimental determinations in certain cases. Mean values were obtained from three or more separate determinations. The incubation time for the reaction mixture was 15 minutes at 37° C.

Concentrations that caused a 50% inhibition of radioligand binding (IC$_{50}$) and Hill coefficient were obtained by computer-assisted regression analysis.

Radioligand Binding Studies:

Membrane preparation from transformed cells. Suspension cells expressing the cloned rat 5-HT$_{2B}$ receptor were harvested by centrifugation at 2,200×g for 15 min at 4° C. Kursar, J. D., D. L. Nelson, D. B. Wainscott, M. L. Cohen, and M. Baez, *Mol. Pharmacol.* 42: 549–557 (1992). Membranes for the binding assays were prepared by vortexing the pellet in 50 mM Tris-HCl, pH 7.4 (0.5×10$^9$ cells/30 ml). The tissue suspension was then centrifuged at 39,800×g for 10 min at 4° C. This procedure was repeated for a total of three washes, with a 10 minute incubation at 37° C. between the first and second wash. The final pellet was homogenized in 67 mM Tris-HCl, pH 7.4 (at 20–40 and 12.5 million cells/ml, original cell number, for cells expressing low and relatively high levels of the 5-HT$_{2B}$ receptor, respectively) using a Tissumizer (Tekmar, Cincinnati, Ohio), setting 65 for 15 seconds.

[$^3$H]5-HT binding studies. Binding assays were automated using a Biomek 1000 (Beckman Instruments, Fullerton, Calif.) and were performed in triplicate in 0.8 ml total volume. Membrane suspension, 200 µl, (0.04–0.27 mg protein) and 200 µl of drug dilution in water were added to 400 µl of 67 mM Tris-HCl, pH 7.4, containing [$^3$H]5-HT, pargyline, CaCl$_2$, and L-ascorbic acid. Final concentrations of pargyline, CaCl$_2$ and L-ascorbic acid were 10 µM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and pre-cooled with ice-cold 50 mM Tris-HCl, pH 7.4. The filters were then washed rapidly four times with one ml ice-cold 50 mM Tris-HCl, pH 7.4. The amount of [$^3$H]5-HT trapped on the filters was determined by liquid scintillation spectrometry (Ready Protein) and automated using a Biomek 1000 (Beckman Instruments, Fullerton, Calif.) and were performed in triplicate in 0.8 ml total volume. Membrane suspension, 200 µl, (0.04–0.27 mg protein) and 200 µl of drug dilution in water were added to 400 µl of 67 mM Tris-HCl, pH 7.4, containing [$^3$H]5-HT, pargyline, CaCl$_2$, and L-ascorbic acid. Final concentrations of pargyline, CaCl$_2$ and L-ascorbic acid were 10 µM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and precooled with ice-cold 50 mM Tris-HCl, pH 7.4. The filters were then washed rapidly four times with one ml ice-cold 50 mM Tris-HCl, pH 7.4. The amount of [$^3$H]5-HT trapped on the filters was determined by liquid scintillation spectrometry (Ready Protein and Beckman) and determined for best fit to a one-site or a two-site binding model using a partial F-test. De Lean, A., A. A. Hancock, and R. J. Lefkowitz, *Mol. Pharmacol.* 21: 5–16 (1981). The following equation was used for a one-site binding model, $$\text{Bound} = \frac{B_{max} \times [L]}{K_d + [L]}$$

where Bound=amount of [³H]5-HT specifically bound, $B_{max}$=maximum number of binding sites, $K_d$=equilibrium dissociation constant and [L]=free concentration of [³H]5-HT, or a two-site binding model, $$\text{Bound} = \frac{B_{max1} \times [L]}{K_{d1} + [L]} + \frac{B_{max2} \times [L]}{K_{d2} + [L]}$$

where Bound=amount of [³H]5-HT specifically bound, $B_{max1}$=maximum number of high affinity binding sites, $B_{max2}$=maximum number of low affinity binding sites, $K_{d1}$=equilibrium dissociation constant for the high affinity site, $K_{d2}$=equilibrium dissociation constant for the low affinity site and [L]=free concentration of [³H]5-HT. The $IC_{50}$ values from the competition assays, the binding parameters for the $IP_3$ standard curve and the $EC_{50}$ and $E_{max}$ values from the $IP_3$ assays were determined by nonlinear regression analysis of four parameter logistic equations (Systat, Systat Inc, Evanston, Ill.). De Lean, A., A. A. Hancock, and R. J. Lefkowitz, *Mol. Pharmacol.* 21: 5–16 (1981). The $IC_{50}$ values were converted to $K_i$ values using the Cheng-Prusoff equation. Cheng, Y., and W. H. Prusoff, *Biochem. Pharmacol.* 22: 3099–3108 (1973).

Compounds of this invention were tested using substantially the procedure describe in the Radioligand assay supra, and are summarized in Table I infra. The values in Table I are expressed as $K_i$ values calculated as described supra. The blank values in Table I indicate that the compound was not tested in the corresponding assay.

TABLE 1

| STRUCTURE | 5-HT$_{2B}$ Cells [3H]Serotonin | | 5-HT$_{2A}$ [125I]DOI | |
|---|---|---|---|---|
| | K$_i$ Rat 5-HT$_{2B}$ | K$_i$ Human 5-HT$_{2B}$ | K$_i$ Human 5-HT$_{2A}$ | K$_i$ Rat 5-HT$_{2A}$ |
| [structure] | AVG. = 6.62 SEM = 0.09 N = 4 | | | |
| [structure] | AVG. = 6.28 SEM = 0.91 N = 4 | | | |

TABLE 1-continued
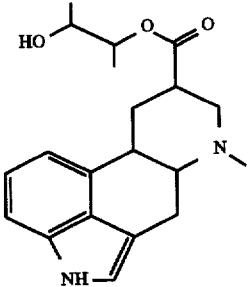
AVG. = 12.20
SEM = 1.54
N = 3
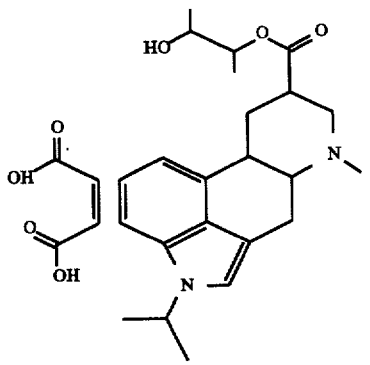
AVG. = 6.87
SEM = 0.55
N = 3
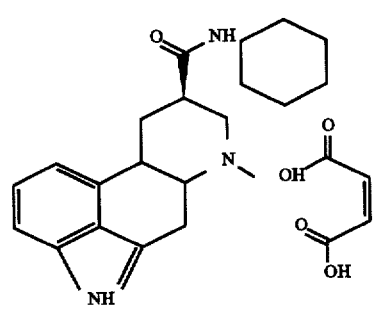
| AVG. = 18.98 | = 0.90 | = 5.12 |
| SEM = 7.56 | = 0.32 | = 1.21 |
| N = 6 | = 5 | = 5 |
193525
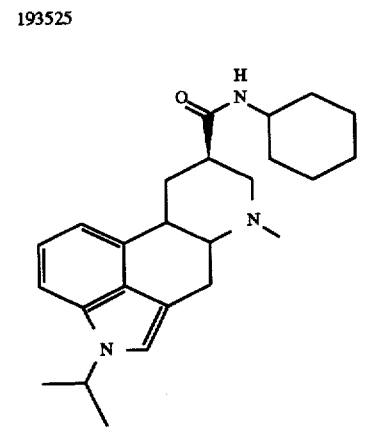
| AVG. = 15.11 | = 15.09 | = 2.05 |
| SEM = 2.43 | = 2.26 | = 0.29 |
| N = 6 | = 5 | = 5 |
237733

TABLE 1-continued
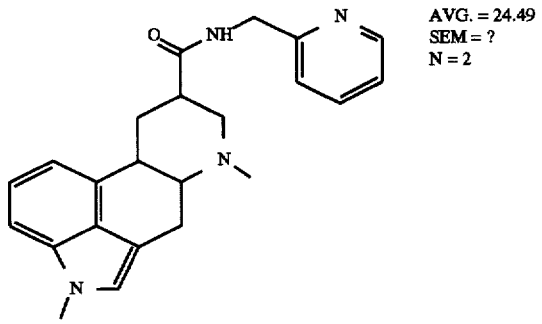
AVG. = 24.49
SEM = ?
N = 2
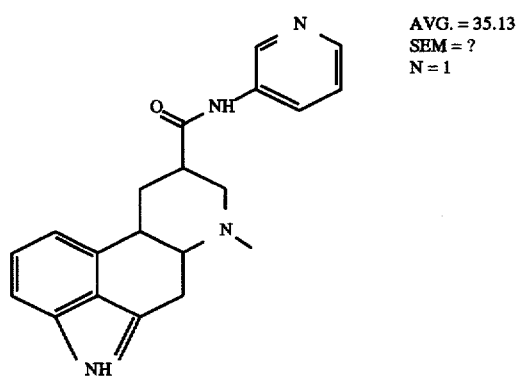
AVG. = 35.13
SEM = ?
N = 1
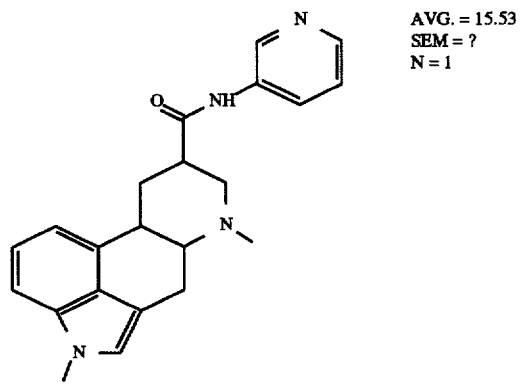
AVG. = 15.53
SEM = ?
N = 1
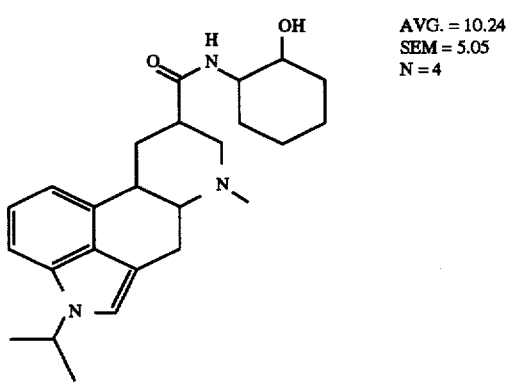
| AVG. = 10.24 | = 74.49 | = 8.91 |
| SEM = 5.05 | = 6.34 | = 0.64 |
| N = 4 | = 3 | = 3 |
215403 CIS ISOMER L TABLE 1-continued
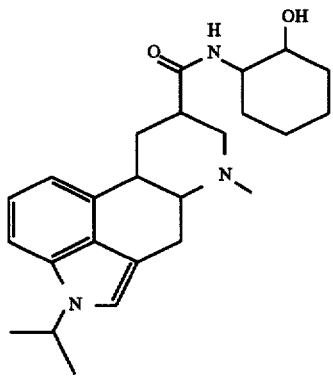
215047 ISOMER L
AVG. = 11.36  = 107.74  = 12.44
SEM = 4.21   = 16.32   = 2.29
N = 4        = 3       = 3
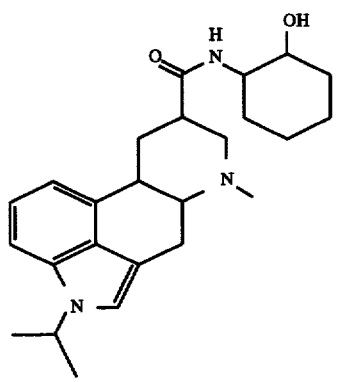
215046 ISOMER U
AVG. = 8.61  = 15.80  = 2.39
SEM = 4.21   = 3.03   = 0.26
N = 4        = 3      = 3
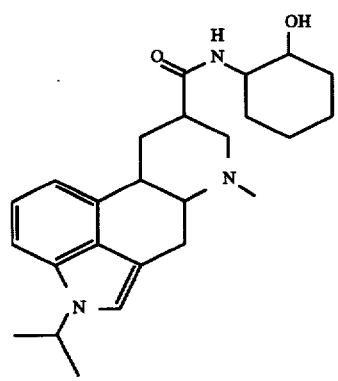
215404 CIS ISOMER U
AVG. = 9.35  = 18.60  = 2.44
SEM = 4.36   = 2.42   = 0.35
N = 4        = 3      = 3

TABLE 1-continued
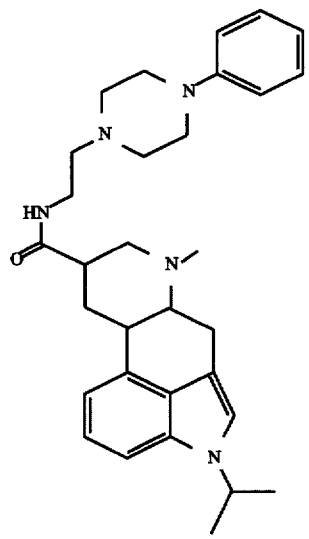
AVG. = 11.87
SEM = 1.93
N = 2
= 32.71
= 0.84
= 2
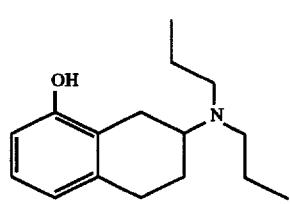
8-OH-DPAT      HBr
AVG. = 4115.29
SEM = 311.55
N = 3
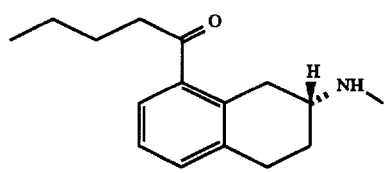
HCl
AVG. = 5153.15
SEM = ?
N = 1
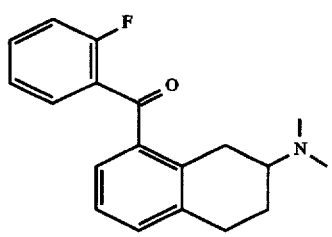
HCl
AVG. = 3019.67
SEM = ?
N = 1
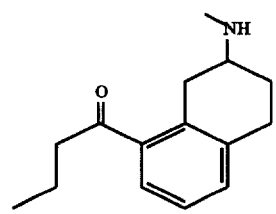
HCl
AVG. = 1501.95
SEM = ?
N = 1

TABLE 1-continued
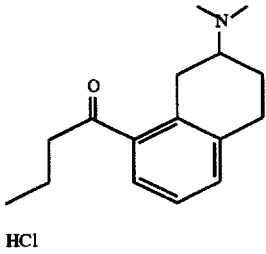
HCl
AVG. = 862.41
SEM = ?
N = 1
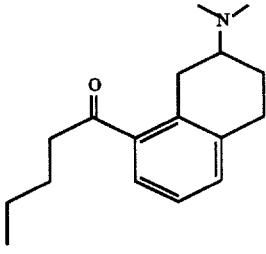
HCl
AVG. = 936.34
SEM = ?
N = 1
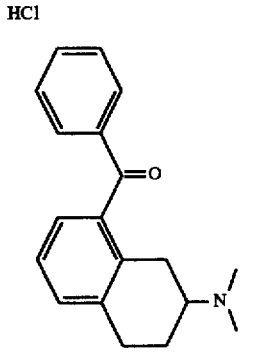
HCl
AVG. = 1752.56
SEM = ?
N = 1
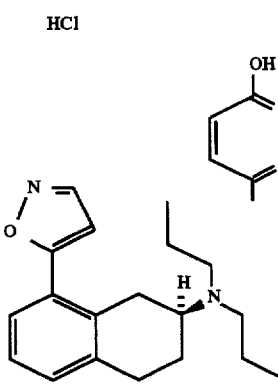
| AVG. = 79.27 | = 215.15 | = 6158.98 |
|---|---|---|
| SEM = 5.39 | = 4.97 | = 2084.19 |
| N = 6 | = 2 | = 2 |
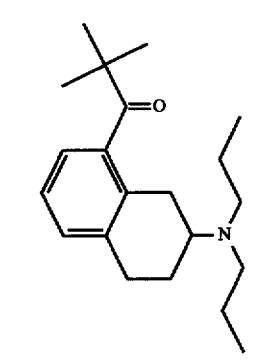
Isomer 1  HBr
| AVG. = 0.00 | = 4749.52 | = 2229.48 |
|---|---|---|
| SEM = ? | = ? | = ? |
| N = 1 | = 1 | = 1 |

TABLE 1-continued
| Structure | | | |
|---|---|---|---|
| 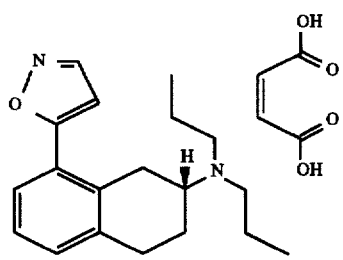 | AVG. =<br>SEM =<br>N = | = 508.94<br>= 45.08<br>= 3 | = 354.03<br>= 41.34<br>= 3 |
| 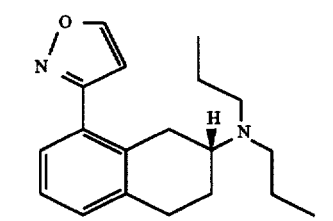<br>HCl | AVG. =<br>SEM =<br>N = | = 784.17<br>= 32.35<br>= 3 | = 127.21<br>= 28.34<br>= 3 |
| 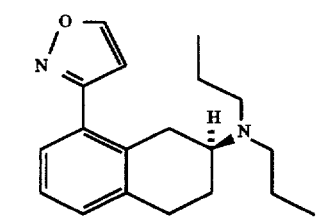<br>HCl | AVG. =<br>SEM =<br>N = | = 256.63<br>= 9.56<br>= 3 | = 5690.86<br>= 560.80<br>= 3 |
| 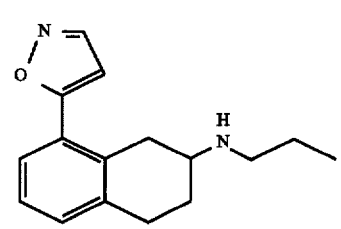<br>HCl | AVG. =<br>SEM =<br>N = | = 1018.01<br>= ?<br>= 1 | = 6028.85<br>= ?<br>= 1 |
| 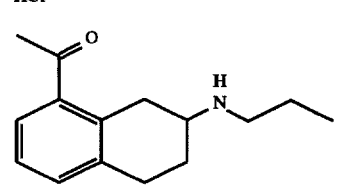<br>HCl | AVG. =<br>SEM =<br>N = | = 1789.87<br>= ?<br>= 1 | = 0.00<br>= ?<br>= 1 |
| 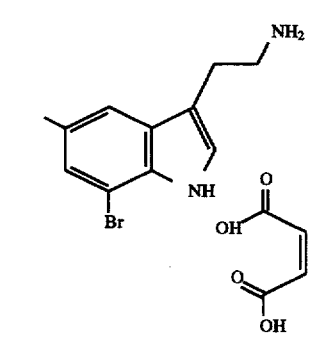 | AVG. = 37.58<br>SEM = 4.76<br>N = 3 | | |

TABLE 1-continued
| Structure | Data |
|---|---|
| 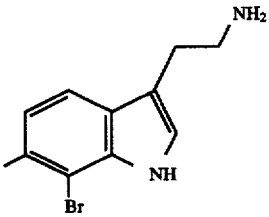 HCl | AVG. = 11.34  = 33.67  = 14.22<br>SEM = 2.24  = 2.01  = 2.36<br>N = 3  = 3  = 3 |
| 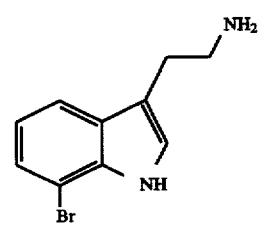 HCl | AVG. = 32.03<br>SEM = 3.49<br>N = 4 |
| 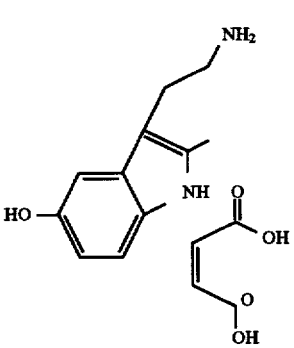 | AVG. = 283.84<br>SEM = 13.48<br>N = 3 |
| 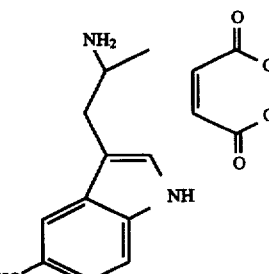 | AVG. = 10.47  = 11.91<br>SEM = 1.46  = 1.09<br>N = 4  = 3 |
| 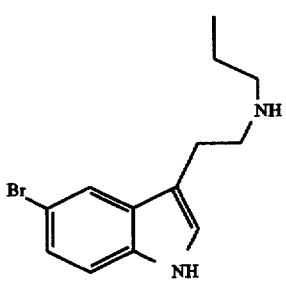 HCl | AVG. = 130.79<br>SEM = 18.70<br>N = 4 |

TABLE 1-continued
| | | | | |
|---|---|---|---|---|
| 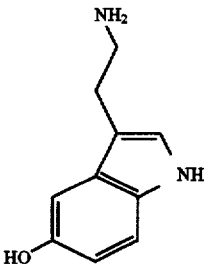 | AVG. = 10.19<br>SEM = 1.99<br>N = 6 | = 9.84<br>= 2.33<br>= 5 | = 7.77<br>= 0.59<br>= 3 | = 15.80<br>= 1.90<br>= 3 |
| 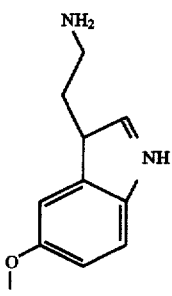 | AVG. = 9.15<br>SEM = 1.47<br>N = 3 | | | |
| 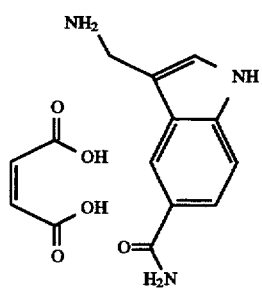 | AVG. = 146.84<br>SEM = 13.49<br>N = 7 | = 127.84<br>= 15.96<br>= 3 | = 120.16<br>= ?<br>= 1 | |
| 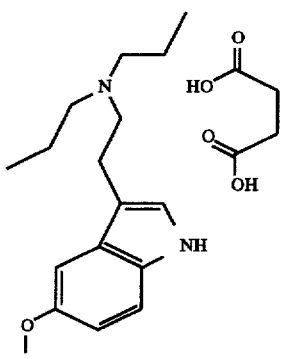 | AVG. = 169.22<br>SEM = 50.27<br>N = 4 | | | |
| 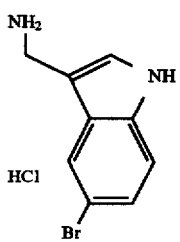 | AVG. = 39.28<br>SEM = 14.04<br>N = 4 | | | |

TABLE 1-continued

| Structure | Data |
|---|---|
| Tryptamine, HCl | AVG. = 112.90<br>SEM = 5.61<br>N = 3 |
| 5-Bromo-1-isopropyl tryptamine, HCl | AVG. = 474.74<br>SEM = 80.54<br>N = 5 |
| 5-Hydroxy-N,N-dipropyltryptamine, HCl | AVG. = 60.96<br>SEM = 16.54<br>N = 5 |
| 5-Methyltryptamine, HCl | AVG. = 32.78<br>SEM = 4.99<br>N = 3 |
| 5-Fluorotryptamine, HCl | AVG. = 5.65<br>SEM = 0.55<br>N = 3 |

TABLE 1-continued
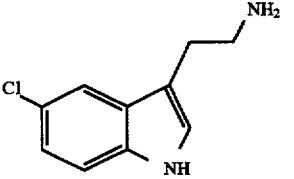
HCl
AVG. = 6.21
SEM = 0.55
N = 6
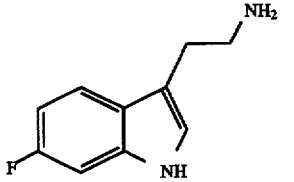
HCl
AVG. = 40.64
SEM = 4.45
N = 3
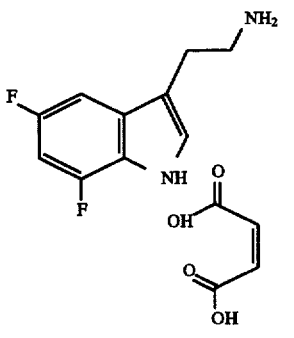
AVG. = 15.37
SEM = 1.67
N = 3
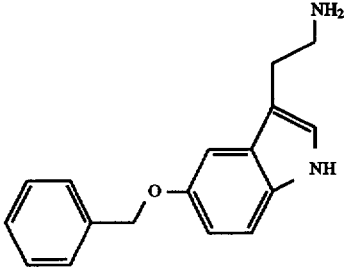
HCl
AVG. = 30.18
SEM = 0.90
N = 3
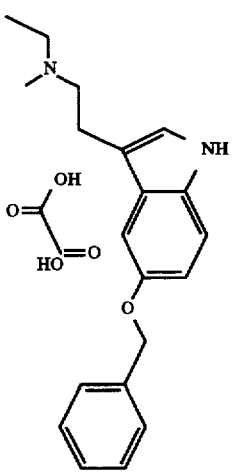
AVG. = 84.49
SEM = 8.44
N = 3

TABLE 1-continued
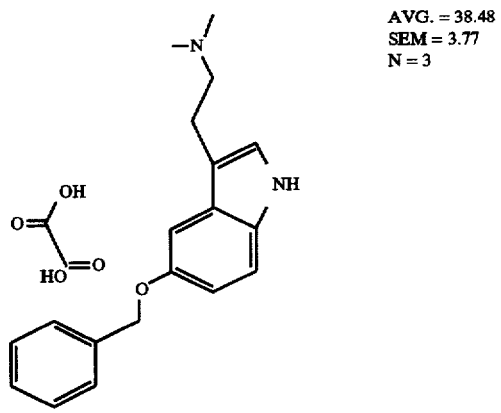
AVG. = 38.48
SEM = 3.77
N = 3
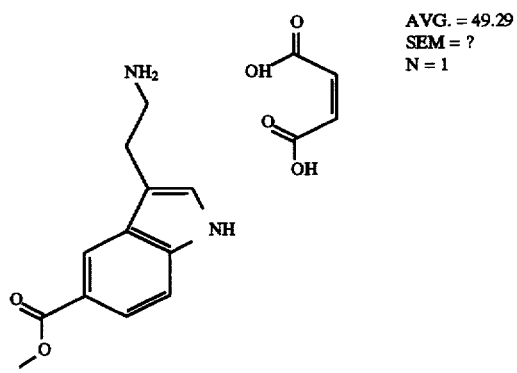
AVG. = 49.29
SEM = ?
N = 1
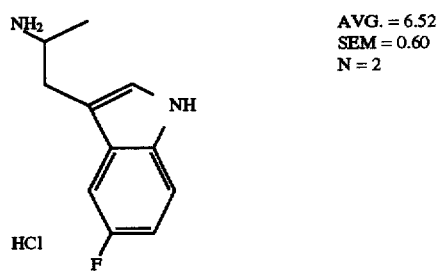
AVG. = 6.52
SEM = 0.60
N = 2
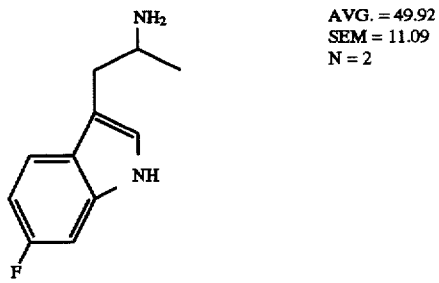
AVG. = 49.92
SEM = 11.09
N = 2

TABLE 1-continued
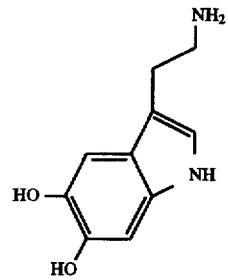
creatinine sulfate salt
AVG. = 41.62
SEM = 10.13
N = 2
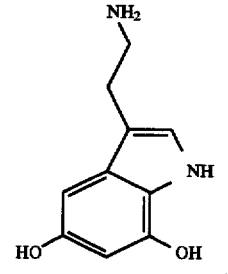
creatinine sulfate salt
AVG. = 4571.89
SEM = 499.67
N = 2
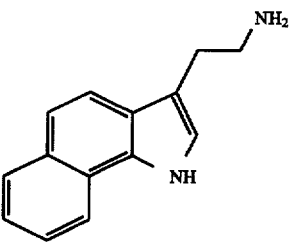
HCl
AVG. = 154.84
SEM = ?
N = 1
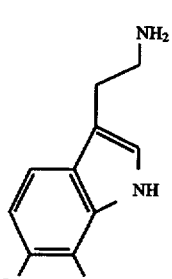
HCl
AVG. = 20.85
SEM = 5.29
N = 2
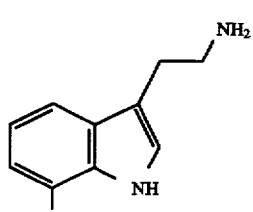
HCl
AVG. = 62.43
SEM = 7.52
N = 3

TABLE 1-continued
| Structure | Data |
|---|---|
| 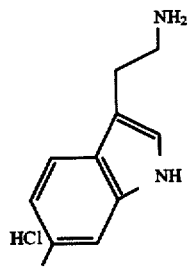 | AVG. = 102.06<br>SEM = 1.62<br>N = 2 |
| 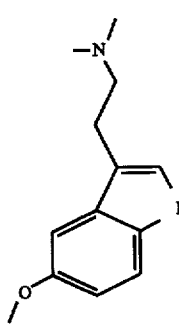 | AVG. = 14.78<br>SEM = ?<br>N = 1 |
| 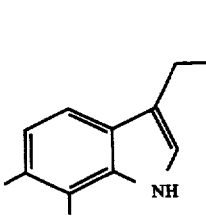 | AVG. = 7.94   = 11.21   = 27.55   = 20.70<br>SEM = 0.52   = ?       = 0.62   = 3.48<br>N = 6        = 1       = 3      = 3 |
| 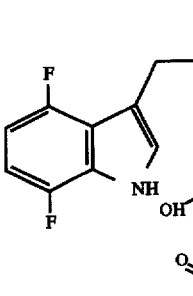 | AVG. = 336.55<br>SEM = ?<br>N = 1 |
| 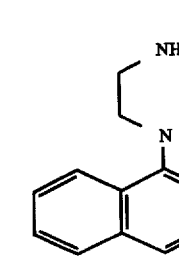 | AVG. = 4.50   = 3.79<br>SEM = 0.47   = 0.80<br>N = 12       = 8 |

TABLE 1-continued
| Structure | | | |
|---|---|---|---|
| 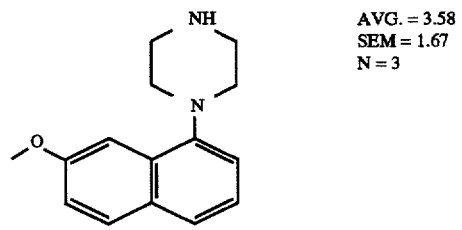 | AVG. = 3.58<br>SEM = 1.67<br>N = 3 | | |
| 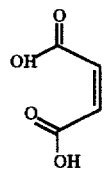<br>HCl | AVG. = 3.17<br>SEM = 0.36<br>N = 3 | = 21.74<br>= 0.74<br>= 3 | = 15.74<br>= 1.41<br>= 3 |
| 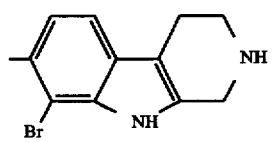 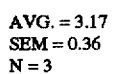 | AVG. = 34.49<br>SEM = 2.85<br>N = 4 | | |
| 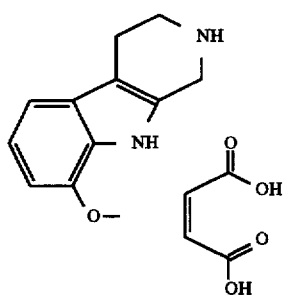 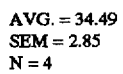<br>ISOMER A | AVG. = 5.61<br>SEM = 0.91<br>N = 5 | = 1.40<br>= 0.08<br>= 5 | = 44.46<br>= 0.75<br>= 3 |
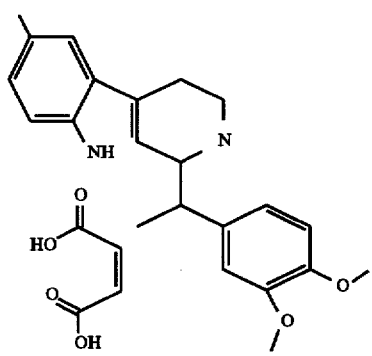

TABLE 1-continued
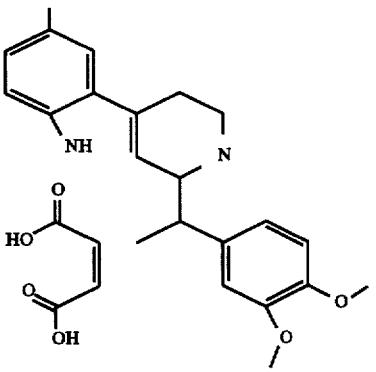
ISOMER B
AVG. = 30.07  = 5.55   = 372.81
SEM = 8.51    = 0.40   = 23.51
N = 5         = 4      = 3
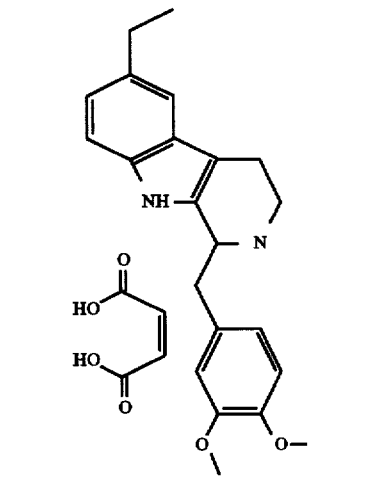
AVG. = 8.16   = 1.50   = 23.39
SEM = 2.16    = 0.35   = 3.81
N = 4         = 4      = 3
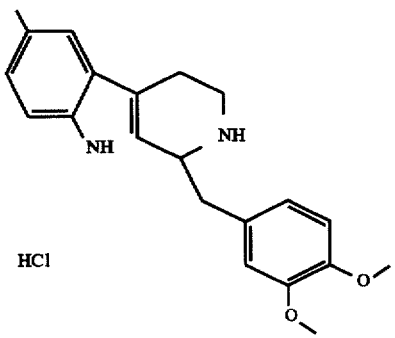
HCl
AVG. = 3.10   = 0.79   = 28.07
SEM = 0.20    = 0.06   = 2.30
N = 3         = 7      = 3
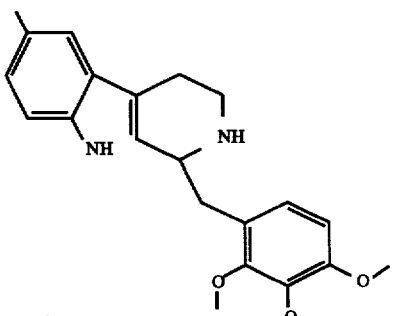
HCl
AVG. = 5.39
SEM = 0.68
N = 3

TABLE 1-continued
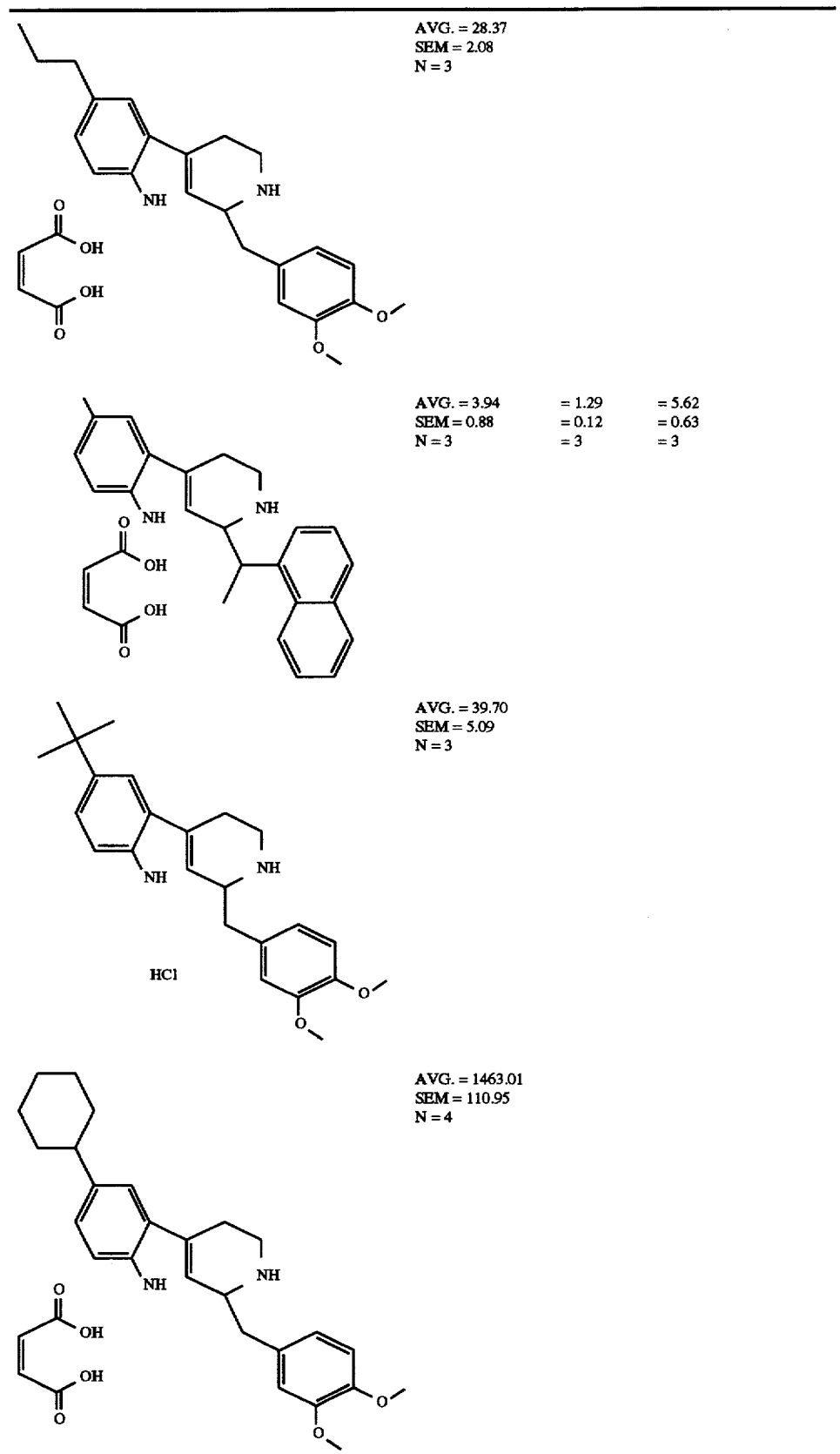

TABLE 1-continued
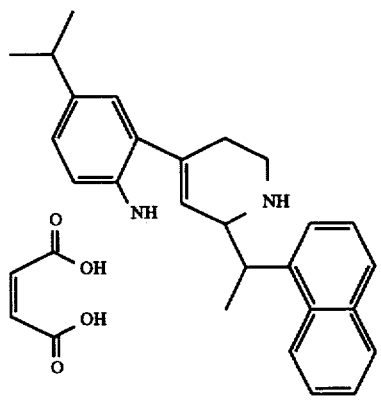
AVG. = 14.18
SEM = 1.74
N = 4
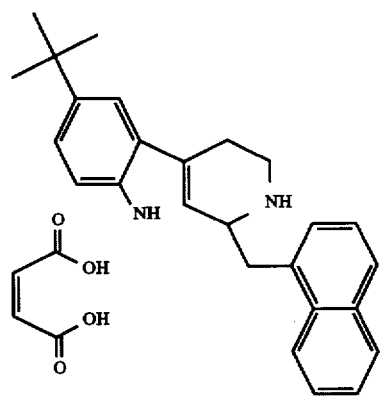
AVG. = 44.91
SEM = 1.48
N = 3
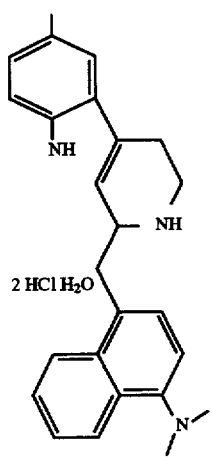
| AVG. = 5.02 | = 1.64 | = 0.83 |
| SEM = 0.51 | = 0.23 | = 0.10 |
| N = 3 | = 4 | = 3 |

TABLE 1-continued
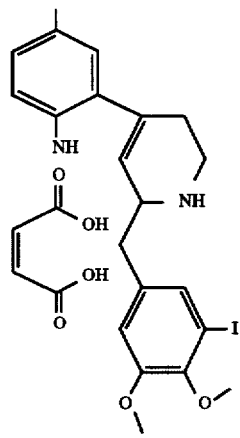
AVG. = 4.82
SEM = 0.23
N = 3
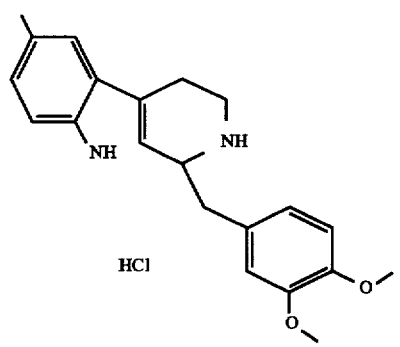
AVG. = 2.16
SEM = 0.33
N = 3
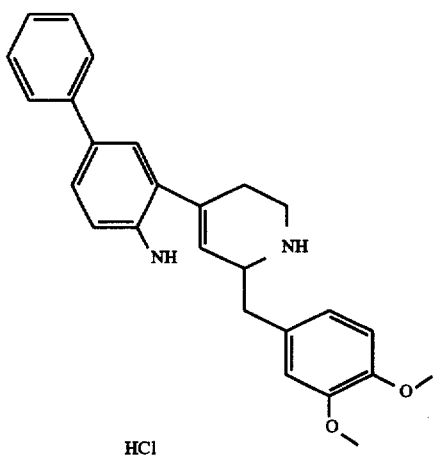
AVG. = 228.87
SEM = 18.34
N = 3

TABLE 1-continued
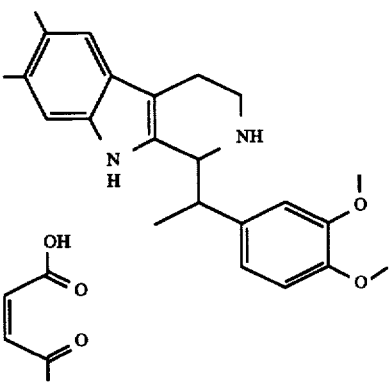
AVG. = 6.42    = 2.01    = 23.08
SEM = 0.78    = ?    = ?
N = 3    = 1    = 1
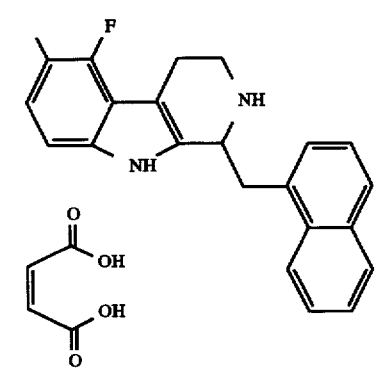
AVG. = 4.38
SEM = 1.25
N = 3
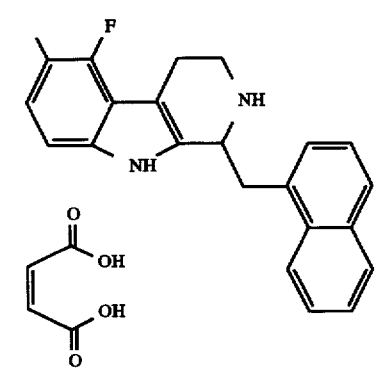
AVG. = 3.31    = 0.74    = 4.63
SEM = 0.31    = 0.04    = 0.26
N = 3    = 3    = 3
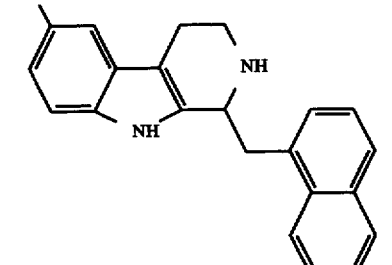
AVG. = 219.79
SEM = 20.68
N = 3

TABLE 1-continued
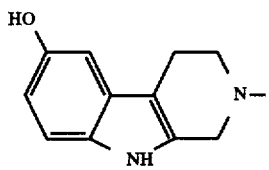
HCl
AVG. = 4609.36
SEM = 316.40
N = 3
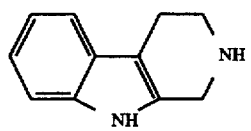
AVG. = 379.15
SEM = 16.72
N = 3
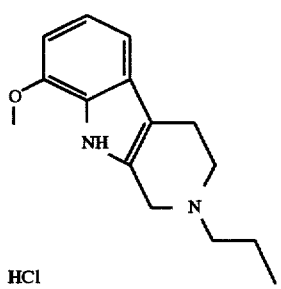
HCl
AVG. = 114.16
SEM = 7.17
N = 3
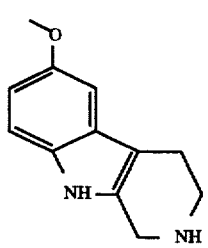
AVG. = 404.85
SEM = 51.64
N = 3
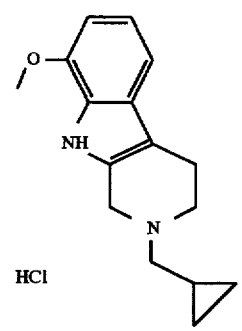
HCl
AVG. = 97.53
SEM = ?
N = 1
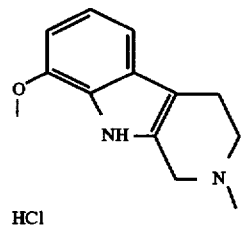
HCl
AVG. = 71.75
SEM = ?
N = 1

TABLE 1-continued
| Structure | | | | |
|---|---|---|---|---|
| 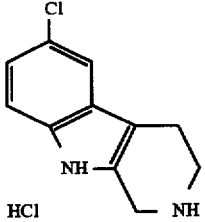 HCl | AVG. = 70.71<br>SEM = 10.08<br>N = 3 | | | |
| 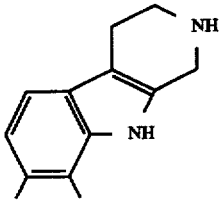 HCl | AVG. = 15.83<br>SEM = 1.73<br>N = 3 | | | |
| 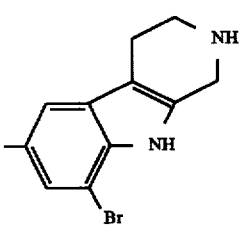 HCl | AVG. = 13.98<br>SEM = 1.00<br>N = 3 | = 16.43<br>= ?<br>= 1 | = 41.71<br>= 7.42<br>= 4 | = 47.00<br>= 5.15<br>= 3 |
| 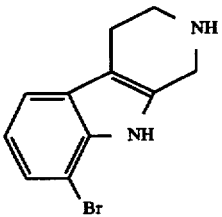 HCl | AVG. = 6.20<br>SEM = 0.62<br>N = 3 | = 9.68<br>= 1.12<br>= 3 | = 22.72<br>= 2.15<br>= 6 | = 25.61<br>= 3.43<br>= 3 |
| 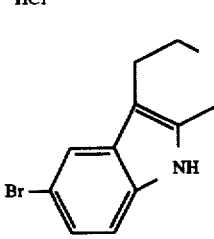 HCl | AVG. = 62.09<br>SEM = 1.76<br>N = 3 | | | |
| 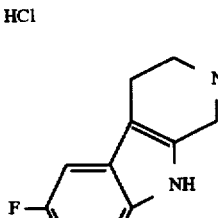 HCl | AVG. = 57.89<br>SEM = 7.60<br>N = 3 | | | |

TABLE 1-continued
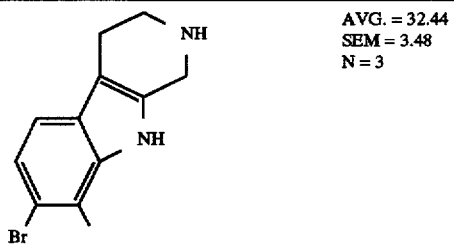
HCl
AVG. = 32.44
SEM = 3.48
N = 3
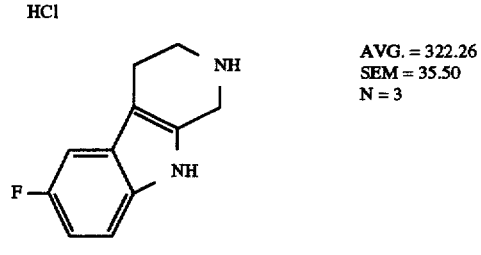
HCl
AVG. = 322.26
SEM = 35.50
N = 3
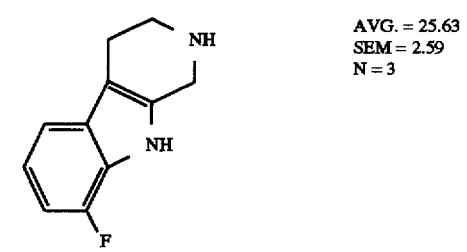
HCl
AVG. = 25.63
SEM = 2.59
N = 3
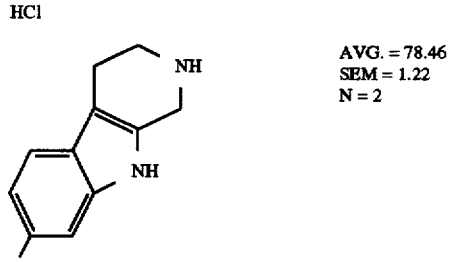
HCl
AVG. = 78.46
SEM = 1.22
N = 2
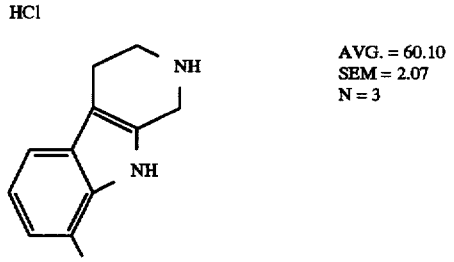
HCl
AVG. = 60.10
SEM = 2.07
N = 3
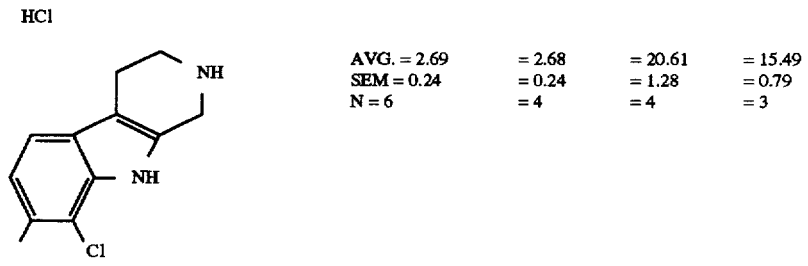
HCl
| AVG. = 2.69 | = 2.68 | = 20.61 | = 15.49 |
| SEM = 0.24 | = 0.24 | = 1.28 | = 0.79 |
| N = 6 | = 4 | = 4 | = 3 |

TABLE 1-continued
| Structure | | | |
|---|---|---|---|
| 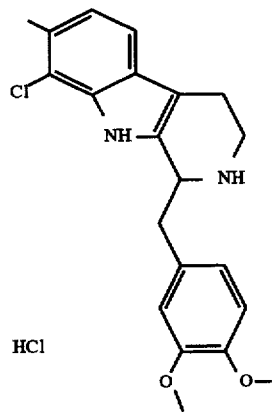 HCl | AVG. = 3.19<br>SEM = 0.33<br>N = 3 | = 0.84<br>= 0.15<br>= 4 | = 0.93<br>= 0.07<br>= 3 |
| 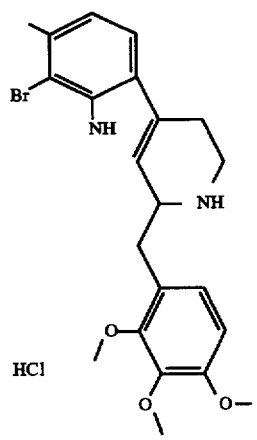 HCl | AVG. = 8.77<br>SEM = ?<br>N = 1 | | |
| 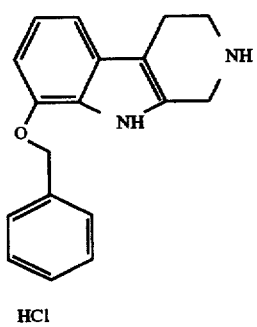 HCl | AVG. = 5652.17<br>SEM = ?<br>N = 1 | | |
| 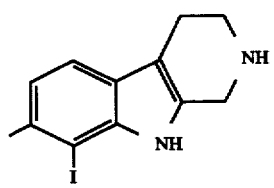 HCl | AVG. = 15.26<br>SEM = ?<br>N = 1 | = 10.15<br>= 2.19<br>= 4 | = 17.76<br>= 0.68<br>= 3 |

TABLE 1-continued
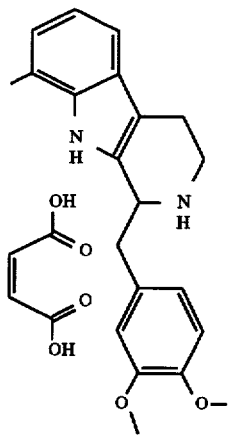
AVG. = = 1.69 = 49.70
SEM = = ? = ?
N = = 1 = 1
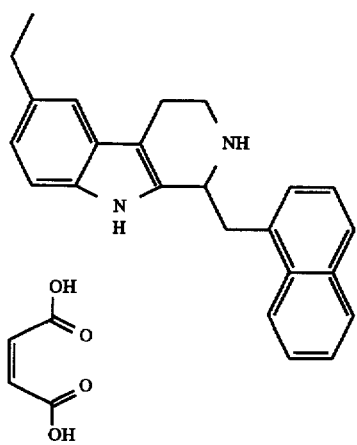
AVG. = = 2.08 = 6.71
SEM = = ? = ?
N = = 1 = 1
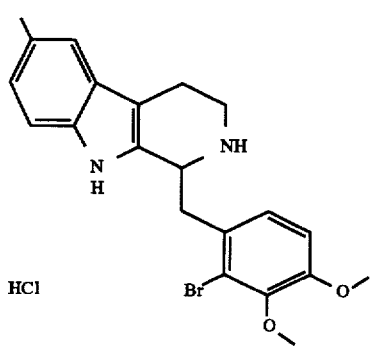
AVG. = = 0.37 = 12.23
SEM = = ? = ?
N = = 1 = 1

TABLE 1-continued
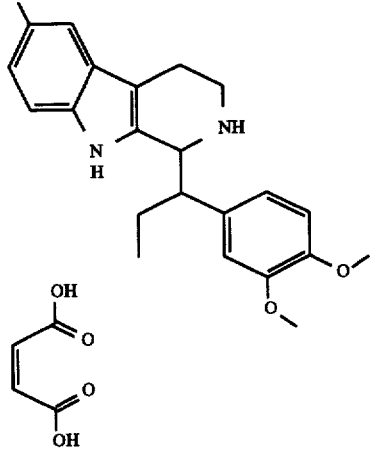
| | | |
|---|---|---|
| AVG. = | = 0.87 | = 17.48 |
| SEM = | = ? | = ? |
| N = | = 1 | = 1 |
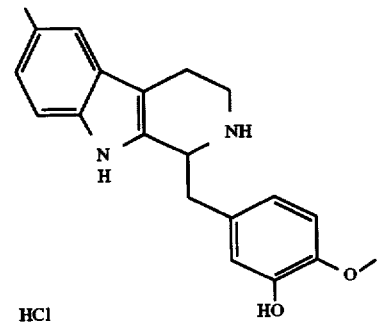
| | | |
|---|---|---|
| AVG. = | = 1.47 | = 54.85 |
| SEM = | = ? | = ? |
| N = | = 1 | = 1 |
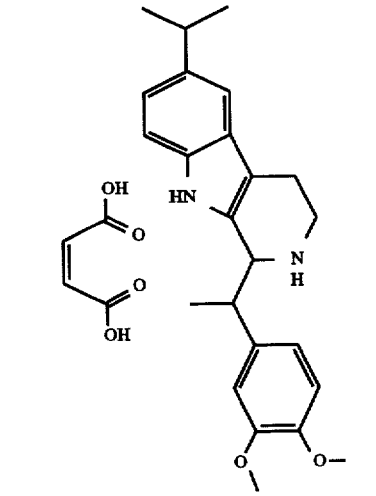
| | | |
|---|---|---|
| AVG. = | = 3.46 | = 201.26 |
| SEM = | = ? | = ? |
| N = | = 1 | = 1 |

TABLE 1-continued
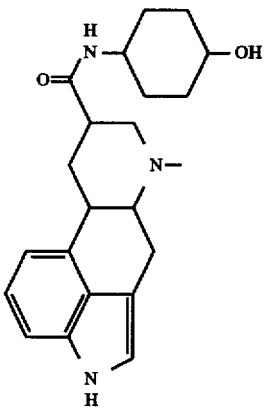
255747, Trans
AVG. = 44.65    = 12.44    = 1.25    = 5.36
SEM = 25.15    = 1.70    = 0.56    = 1.85
N = 5    = 3    = 5    = 5
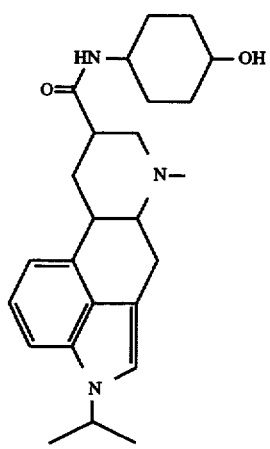
278458, CIS
AVG. = 22.29    = 4.30    = 11.33    = 1.57
SEM = 6.65    = 0.30    = 3.26    = 0.49
N = 5    = 3    = 5    = 5
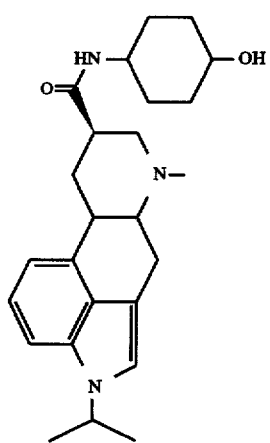
253535 (TRANS)
AVG. = 30.90    = 6.24    = 21.18    = 2.82
SEM = 4.52    = 0.29    = 3.78    = 0.40
N = 3    = 3    = 3    = 3

TABLE 1-continued

| Structure | | | |
|---|---|---|---|
| 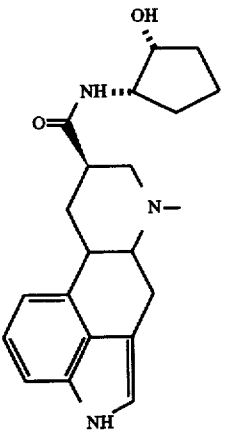 | AVG. =<br>SEM =<br>N = | = 7.87<br>= —<br>= 1 | = 0.60<br>= —<br>= 1 |
| 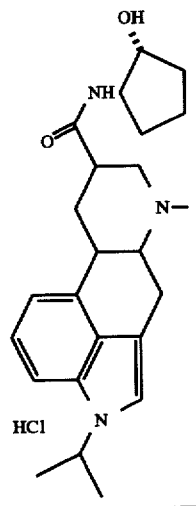 | AVG. =<br>SEM =<br>N = | = 2.24<br>= —<br>= 1 | = 21.92<br>= —<br>= 1 |

| The following Cell assays use Human Cells | | | |
|---|---|---|---|
| Compound | 5HT$_{2B}$ Cells | 5HT$_{2A}$ Cells | 5HT$_{2C}$ Cells |
| Example 100 | 16.44 | 292.58 | 351.96 |
| Example 105 | 22.07 | 86.48 | 195.44 |
| Example 102 | 168.49 | 917.16 | 2172.86 |
| Example 106 | 367.41 | 263.94 | 1108.87 |
| Example 104 | 11.35 | 32.99 | 52.06 |
| Example 97 | 9.56 | 123.93 | 220.51 |
| Example 99 | 106.17 | 556.40 | 1117.00 |
| Example 107 | 177.89 | 362.79 | 325.10 |
| Isomer 107(1) | 142.80 | 152.65 | 137.76 |
| Isomer 107(2) | 2894.33 | 1967.05 | 6211.80 |
| Example 101 | 121.19 | 172.03 | 783.35 |
| Example 98 | 52.54 | 53.65 | 202.60 |
| Example 96 | 667.82 | 277.62 | 976.73 |
| Example 95 | 839.63 | 3443.51 | 2641.21 |
| Example 103 | 3520.31 | 1447.65 | 9247.06 |

Assay Methods 5-HT$_{2B}$ receptor in tissue in vitro:

Male Wistar rats (150–375 g; Laboratory Supply, Indianapolis, Ind.) were sacrificed by cervical dislocation, and longitudinal section of the stomach fundus were prepared for in vitro examination. Four preparations were obtained from one rat fundus. Cohen, M. L. and J. Pharmacol. Exp. Ther. 233:75–79 (1985). Tissues were mounted in organ baths containing 10 mL of modified Krebs' solution of the following composition (millimolar concentrations): NaCl, 118.2, KCl, 4.6; CaCl$_2$.H$_2$O, 1.6; KH$_2$PO$_4$, 1.2; MgSO$_4$, 1.2; dextrose, 10.0; and NaHCO$_3$, 24.8. Tissue bath solutions were maintained at 37° C. and equilibrated with 95% O$_2$ and 5% CO$_2$. Tissues were placed under optimum resting force (4 g) and were allowed to eguilibrate for approximately 1 hour before exposure to the test compound. Isometric contractions were recorded as changes in grams of force on a Beckman Dynograph with Statham UC-3 transducers.

Determination of Apparent Antagonist Dissociation Constant:

Noncumulative contractile concentration-response curves for serotonin and other agonists in the fundus were obtained by a stepwise increase in concentration after washing out the preceding concentrations every 15–20 minutes. Each agonist concentration remained in contact with the tissue for approximately 2 minutes and maximum response to each compound concentration was measured $ED_{50}$ values were taken as the concentration of agonist that produced half-maximal contraction. After control responses were obtained, tissues were incubated with an appropriate concentration of buffer or antagonist for 1 hour. Responses to serotonin were then repeated in the presence of an antagonist. Concentration responses utilized only one agonist and one antagonist concentration per tissue. In general, successive agonist responses in the presence of buffer treatment were unaltered (average dose ratio was 1.28±0.21).

Apparent antagonist dissociation constants ($K_B$) were determined for each concentration of antagonist according to the following equation:

$$K_B = [B]/(\text{dose ratio}-1)$$

where [B] is the concentration of the antagonist and dose ratio is the $ED_{50}$ of the agonist in the presence of the antagonist divided by the control $ED_{50}$. Generally, parallel shifts in the concentration-response curves occurred in the presence of antagonists. The results were expressed as the negative logarithm of the $K_B$ (i.e., $-\log K_B$). Calculations were completed using known methods.

The results of the in vitro assay for certain compounds of this invention are presented in Table II. The values in Table II are expressed as $-\log K_B \pm$ standard error (number of data points). The 5-$HT_{2B}$ value represents the negative log of the concentration of an antagonist that will produce a two fold dextral shift in the concentration response curve to serotonin in the rat stomach fundus which is mediated by 5-$HT_{2B}$ receptors. Likewise, the 5-$HT_{2A}$ value represents the negative log of the concentration of an antagonist that will produce a two fold dextral shift in the concentration response curve to serotonin in the rat jugular vein which is mediated by 5-$HT_{2A}$ receptors. The blank values in Table II indicate that the compound was not tested in the indicated assay.

TABLE II

| Example # | 5-$HT_{2B}$ (Fundus) | 5-$HT_{2A}$ (Jugular) |
|---|---|---|
| 1 | 9.00 ± 0.07 (3) | |
| 2 | | |
| 3 | 8.78 ± 0.24 (4) | |
| 4 | 8.92 ± 0.29 (4) | |
| 5 | | |
| 6 | 9.60 ± 0.13 (7) | |
| 7 | 9.02 ± 0.35 (3) | |
| 8 | 8.45 ± 0.24 (3) | |
| 9 | 9.30 ± 0.12 (7) | |
| 10 | 9.22 ± 0.05 (3) | |
| 11 | <7.52 (4) | |
| 12 | 9.29 ± 0.18 (4) | |
| 13 | 8.50 ± 0.13 (4) | |
| 14 | 9.61 ± 0.22 (5) | |
| 15 | 9.34 ± 0.12 (3) | |
| 16 | 9.71 ± 0.14 (6) | 8.15 ± 0.28 (3) |
| 17 | 9.46 ± 0.11 (6) | 7.66 ± 0.13 (4) |
| 18 | 8.80 ± 0.17 (3) | |
| 19 | 10.12 ± 0.18 (3) | |
| 20 | 9.48 ± 0.30 (4) | 7.21 ± 0.20 (4) |
| 21 | | |
| 22 | 8.21 ± 0.43 (3) | |
| 23 | | |
| 24 | | |
| 25 | | |
| 26 | | |
| 27 | | |
| 28 | 8.55 ± 0.10 (4) | |
| 29 | 8.12 ± 0.16 (7) | |
| 30 | 8.89 ± 0.12 (4) | |
| 31 | 8.95 ± 0.17 (3) | 7.29 ± 0.09 (4) |
| 32 | | |
| 33 | | |
| 34 | 9.42 ± 0.18 (5) | |
| 35 | *9.06 ± 0.27 (3) | |
| 36 | 9.80 ± 0.15 (4) | 8.14 ± 0.10 (6) |
| 37 | 9.19 ± 0.14 (4) | |
| 38 | | |
| 39 | 8.32 ± 0.17 (3) | |
| 40 | 9.75 ± 0.11 (6) | |
| 41 | 9.81 ± 0.18 (3) | 7.94 ± 0.15 (6) |
| 42 | 9.56 ± 0.22 (3) | |
| 43 | 9.44 ± 0.16 (6) | |
| 44 | 8.40 ± 0.40 (3) | |
| 45 | 8.14 ± 0.32 (3) | |
| 46 | 9.37 ± 0.11 (8) | 8.22 ± 0.07 (12) |
| 47 | | |
| 48 | ** | |
| 49 | *10.41 ± 0.22 (5) | |
| 50 | 8.40 ± 0.28 (3) | |
| 51 | 9.75 ± 0.11 (8) | 8.07 ± 0.10 (8) |
| 52 | *9.10 ± 0.28 (3) | |
| 53 | ** | |
| 54 | ** | |
| 55 | 8.95 ± 0.07 (4) | |
| 56 | *7.53 ± 1.08 (4) | |
| 57 | <8.0 (3) | |
| 58 | <7.52 (4) | |
| 59 | 9.69 ± 0.21 (7) | |
| 60 | 8.92 ± 0.04 (4) | |
| 61 | 8.44 ± 0.22 (4) | |
| 62 | 8.58 ± 0.23 (3) | |
| 63 | 9.09 ± 0.23 (3) | |
| 64 | 9.73 ± 0.05 (3) | |

*Approximate value
**Non-competitive inhibitors at 30 nM

Functional In vitro assay:

Sprague-Dawley rats (200–250 g; Laboratory Supply, Indianapolis, Ind.) were sacrificed by cervical dislocation and 8 cm segment of distal colon was removed and washed in ice cold modified Kreb's solution of the following composition (millimolar): NaCl, 118.2; KCl, 4.6; $CaCl_2$, $H_2O$, 1.6; $KH_2PO_4$, 1.2; $MgSO_4$, 1.2; dextrose, 10.0; and $NaHCO_3$, 24.8. The colon was mounted on a glass rod and the longitudinal muscle layer with attached myenteric plexi was removed and mounted in organ baths, containing above described Kreb's solution maintained at 37° C. and equilibrated with 95% $O_2$ and 5% $CO_2$. Tissues were placed under 2 g tension and allowed to stabilize for 1 hour. Isometric contractions were recorded as changes in grams of force using grass FT03 transducers and $MI^2$-computerized dynograph system. Cumulative concentration-response curves for serotonin were obtained by a stepwise increase in concentration after washing out the preceding concentration for 10–15 minutes. Each agonist concentration remained in contact with the tissue for 5 minutes. Maximum response to each concentration was determined and digitized. $EC_{50}$ values were taken as the concentration of agonist that produced half maximal contraction. After control responses were obtained, tissues were incubated with an appropriate concentration of antagonist for 15 minutes. Response to serotonin were then repeated in the presence of an antagonist. Concentration-response utilized only one concentration of antagonist per tissue. Apparent antagonist dissociation constants ($K_B$) were determined for each concentration of antagonist according to the following equation:

$$K_B = [B]/(\text{dose ratio} - 1),$$

where [B] is the concentration of the antagonist and dose ratio is the $ED_{50}$ of the agonist in the presence of antagonist divided by the control $ED_{50}$. The results were expressed as the negative logarithm of the $K_B$ (i.e., $-\log K_B$) (Br. J. Pharmacol. Methods 4:4165, (1980).

The functional in vitro method described supra, was used to test compounds of this invention. Results obtained using the functional in vitro assay are presented in Table III. Values are expressed as $pK_i$ and $pA_2$ ($-\log K_B$). The following table illustrates the results obtained when the compounds were tested using the Radioligand assay supra. (pKi) and the functional in vitro method described supra. (pA$_2$)

TABLE III

| Compound | pKi | pA$_2$ |
|---|---|---|
| Example 73 | 7.85 | 8.9 |
| Example 49 | 8.4 | 8.2 |
| Example 20 | 8.51 | 7.8 |
| Example 72 | 7.8 | 7.5 |
| Example 41 | 8.19 | 7.2 |
| Example 17 | 8.09 | 6.2 |
| Example 22 | 8.27 | 4.8 |
| 7-methyl-8-chloro-1,2,3,4-tetrahydro-9H-pyrido[3,4b]-indole | 8.57 | 8.3 |
| 6-bromo-1,2,3,4-tetrahydro-9H-pyrido[3,4b]-indole | 7.21 | 8.2 |
| 6-chloro-1,2,3,4-tetrahydro-9H-pyrido[3,4b]-indole | 7.15 | 7.2 |

In vivo Studies:

Sprague-Dawley Rats (250–300 g) were fasted overnight. The rats were anesthetized with urethane (250 mg) delivered intraperitoneally. The abdominal cavity was opened and strain guage transducers were sewn on the antimesenteric border of the colon. The transducers were oriented to record circular muscle contractions. The animal body temperature was maintained by a heating pad. An intravenous catheter was inserted into the jugular vein for drug administration. The carotid blood pressure was also monitored. Output of the strain guage transducers was graphed on a Beckman Dynograph. Baseline motility was monitored for 30 minutes. At the end of the 30 minute period, a vehicle control dose was administered and motility was recorded for an additional 15 minutes. A serotonin dose response was developed. Successively higher doses of serotonin were administered at 15 minute intervals. An $ED_{50}$ dose was calculated, which was the dose producing half maximal contraction. In antagonist experiments, historical $ED_{50}$ dose was administered to validate the experimental set up. Next, a dose of antagonist was given. The motility was monitored for 15 minutes. After the 15 minute monitoring, an $ED_{50}$ dose was administered. Motility was evaluated by measuring the number of contractions and multiplying them by the amplitude of contractions over a set time period to provide a Motility Index. The percent inhibition was calculated from the vehicle (no antagonist) treated group. A minimum of three rats were used for each concentration and data from different animals was pooled to determine $ED_{50}$ values.

Compounds of this invention proved to be active using the in vivo method described supra. For example, the compound of Example 73 produced an $ED_{50}$ value of 3.2 mg/kg, i.v.

We claim:

1. A method for treating a mammal suffering from or susceptible to a condition associated with abnormal or dysfunctional 5-HT$_{2B}$ receptor stimulation, comprising administering to the mammal an effective amount of a compound of the Formula

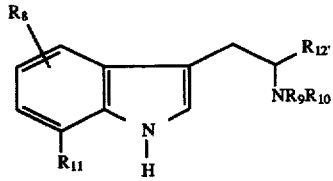

wherein

R$_8$ is hydrogen, C$_1$–C$_6$ alkyl, C$_2$–C$_6$ alkenyl, halo, halo(C$_2$–C$_6$)alkyl, halo(C$_2$–C$_6$)alkenyl, COR$_5$, C$_1$–C$_{10}$ alkanoyl, CO$_2$R$_5$, (C$_1$–C$_6$ alkyl)$_m$amino, NO$_2$, —SR$_5$, OR$_5$, C$_3$–C$_8$ cycloalkyl, substituted C$_3$–C$_8$ cycloalkyl, C$_3$–C$_8$ cycloalkyl-(C$_1$–C$_3$)alkyl, C$_5$–C$_8$ cycloalkenyl, substituted C$_5$–C$_8$ cycloalkenyl, C$_5$–C$_8$ cycloalkenyl-(C$_1$–C$_3$)alkyl, or C$_7$–C$_{20}$ arylalkyl;

R$_5$ is hydrogen or C$_1$–C$_4$ alkyl;

R$_{5'}$ is C$_1$–C$_4$ alkyl;

m is 1 or 2;

R$_9$ and R$_{10}$ independently are hydrogen, C$_1$–C$_6$ alkyl, C$_3$–C$_8$ cycloalkyl, substituted C$_3$–C$_8$ cycloalkyl, C$_3$–C$_8$ cycloalkyl-(C$_1$–C$_3$)alkyl, C$_5$–C$_8$ cycloalkenyl-(C$_1$–C$_3$) alkyl, or C$_7$–C$_{20}$ arylalkyl;

R$_{11}$ is C$_1$–C$_4$ alkyl, OR$_{5'}$, fluoro, bromo, iodo, or chloro; and

R$_{12'}$ is hydrogen or C$_1$–C$_4$ alkyl; or a pharmaceutically acceptable salt or solvate thereof.

2. The method of claim 1 wherein the compound is a 5-HT$_{2B}$ receptor antagonist.

3. A method of claim 1 wherein the condition is urinary incontinence, bladder dysfunction, uterine dysfunction, a cardiovascular disorder, or a respiratory disorder.

4. A method of claim 3 wherein the condition is a cardiovascular disorder.

5. A method of claim 3 wherein the condition is a bladder dysfunction or urinary incontinence.

6. A method of claim 3 wherein the condition is a respiratory disorder.

7. The method of claim 1 wherein the condition is migraine headache.

8. A method for treating a mammal suffering from or susceptible to a Functional Bowel Disorder associated with abnormal or dysfunctional 5-HT$_{2B}$ receptor stimulation, comprising administering to the mammal an effective amount of a compound of the Formula

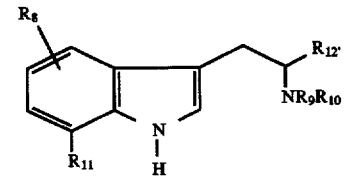

wherein

R$_8$ is hydrogen, C$_1$–C$_6$ alkyl, C$_2$–C$_6$ alkenyl, halo, halo(C$_2$–C$_6$)alkyl, halo(C$_2$–C$_6$)alkenyl, COR$_5$, C$_1$–C$_{10}$ alkanoyl, CO$_2$R$_5$, (C$_1$–C$_6$ alkyl)$_m$amino, NO$_2$, —SR$_5$, OR$_5$, C$_3$–C$_8$ cycloalkyl, substituted C$_3$–C$_8$ cycloalkyl, $C_3-C_8$ cycloalkyl-($C_1-C_3$)alkyl, $C_5-C_8$ cycloalkenyl, substituted $C_5-C_8$ cycloalkenyl, $C_5-C_8$ cycloalkenyl-($C_1-C_3$)alkyl, or $C_7-C_{20}$ arylalkyl;

$R_5$ is hydrogen or $C_1-C_4$ alkyl;

$R_{5'}$ is $C_1-C_4$ alkyl;

m is 1 or 2;

$R_9$ and $R_{10}$ independently are hydrogen, $C_1-C_6$ alkyl, $C_3-C_8$ cycloalkyl, substituted $C_3-C_8$ cycloalkyl, $C_3-C_8$ cycloalkyl-($C_1-C_3$)alkyl, $C_5-C_8$ cycloalkenyl-($C_1-C_3$) alkyl, or $C_7-C_{20}$ arylalkyl;

$R_{11}$ is $C_1-C_4$ alkyl, $OR_{5'}$, fluoro, bromo, iodo, or chloro; and $R_{12'}$ is hydrogen or $C_1-C_4$ alkyl; or a pharmaceutically acceptable salt or solvate thereof.

9. The method of claim 8 wherein the Functional Bowel Disorder is Irritable Bowel Syndrome, ichlasia, hypertonic lower esophpageal sphincter, tachygastria, hypermotility associated with irritable bowel syndrome, or constipation.

10. A method for blocking a 5-$HT_{2B}$ receptor in a mammal comprising administering to the mammal a 5-$HT_{2B}$ receptor-blocking dose of a compound of the Formula

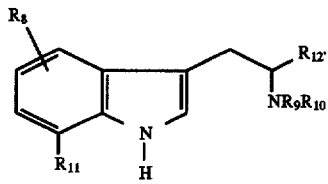

wherein $R_8$ is hydrogen, $C_1-C_6$ alkyl, $C_2-C_6$ alkenyl, halo, halo ($C_2-C_6$)alkyl, halo($C_2-C_6$)alkenyl, $COR_5$, $C_1-C_{10}$ alkanoyl, $CO_2R_{5'}$, ($C_1-C_6$ alkyl)$_m$amino, $NO_2$, —$SR_5$, $OR_5$, $C_3-C_8$ cycloalkyl, substituted $C_3-C_8$ cycloalkyl, $C_3-C_8$ cycloalkyl-($C_1-C_3$)alkyl, $C_5-C_8$ cycloalkenyl, substituted $C_5-C_8$ cycloalkenyl, $C_5-C_8$ cycloalkenyl-($C_1-C_3$)alkyl, or $C_7-C_{20}$ arylalkyl;

$R_5$ is hydrogen or $C_1-C_4$ alkyl;

$R_{5'}$ is $C_1-C_4$ alkyl;

m is 1 or 2;

$R_9$ and $R_{10}$ independently are hydrogen, $C_1-C_6$ alkyl, $C_3-C_8$ cycloalkyl, substituted $C_3-C_8$ cycloalkyl, $C_3-C_8$ cycloalkyl-($C_1-C_3$)alkyl, $C_5-C_8$ cycloalkenyl-($C_1-C_3$) alkyl, or $C_7-C_{20}$ arylalkyl;

$R_{11}$ is $C_1-C_4$ alkyl, $OR_{5'}$, fluoro, bromo, iodo, or chloro; and $R_{12'}$ is hydrogen or $C_1-C_4$ alkyl; or a pharmaceutically acceptable salt or solvate thereof.

11. The method of claim 10 wherein the mammal is a human.

12. A method for selectively blocking a 5-$HT_{2B}$ receptor in a mammal comprising administering to the mammal a 5-$HT_{2B}$ selective compound of the Formula

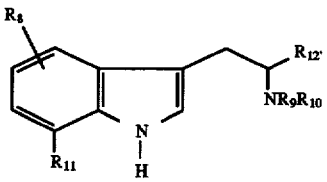

wherein $R_8$ is hydrogen, $C_1-C_6$ alkyl, $C_2-C_6$ alkenyl, halo, halo ($C_2-C_6$)alkyl, halo($C_2-C_6$)alkenyl, $COR_5$, $C_1-C_{10}$ alkanoyl, $CO_2R_{5'}$, ($C_1-C_6$ alkyl)$_m$amino, $NO_2$, —$SR_5$, $OR_5$, $C_3-C_8$ cycloalkyl, substituted $C_3-C_8$ cycloalkyl, $C_3-C_8$ cycloalkyl-($C_1-C_3$)alkyl, $C_5-C_8$ cycloalkenyl, substituted $C_5-C_8$ cycloalkenyl, $C_5-C_8$ cycloalkenyl-($C_1-C_3$)alkyl, or $C_7-C_{20}$ arylalkyl;

$R_5$ is hydrogen or $C_1-C_4$ alkyl;

$R_{5'}$ is $C_1-C_4$ alkyl;

m is 1 or 2;

$R_9$ and $R_{10}$ independently are hydrogen, $C_1-C_6$ alkyl, $C_3-C_8$ cycloalkyl, substituted $C_3-C_8$ cycloalkyl, $C_3-C_8$ cycloalkyl-($C_1-C_3$)alkyl, $C_5-C_8$ cycloalkenyl-($C_1-C_3$) alkyl, or $C_7-C_{20}$ arylalkyl;

$R_{11}$ is $C_1-C_4$ alkyl, $OR_{5'}$, fluoro, bromo, iodo, or chloro; and $R_{12'}$ is hydrogen or $C_1-C_4$ alkyl;

a pharmaceutically acceptable salt or solvate thereof.

13. An article of manufacture comprising a pharmaceutical agent of the Formula

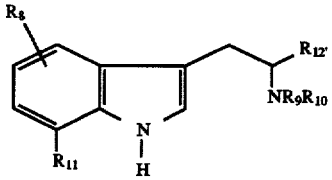

wherein $R_8$ is hydrogen, $C_1-C_6$ alkyl, $C_2-C_6$ alkenyl, halo, halo ($C_2-C_6$)alkyl, halo($C_2-C_6$)alkenyl, $COR_5$, $C_1-C_{10}$ alkanoyl, $CO_2R_{5'}$, ($C_1-C_6$ alkyl)$_m$amino, $NO_2$, —$SR_5$, $OR_5$, $C_3-C_8$ cycloalkyl, substituted $C_3-C_8$ cycloalkyl, $C_3-C_8$ cycloalkyl-($C_1-C_3$)alkyl, $C_5-C_8$ cycloalkenyl, substituted $C_5-C_8$ cycloalkenyl, $C_5-C_8$ cycloalkenyl-($C_1-C_3$)alkyl, or $C_7-C_{20}$ arylalkyl;

$R_5$ is hydrogen or $C_1-C_4$ alkyl;

$R_{5'}$ is $C_1-C_4$ alkyl;

m is 1 or 2;

$R_9$ and $R_{10}$ independently are hydrogen, $C_1-C_6$ alkyl, $C_3-C_8$ cycloalkyl, substituted $C_3-C_8$ cycloalkyl, $C_3-C_8$ cycloalkyl-($C_1-C_3$)alkyl, $C_5-C_8$ cycloalkenyl-($C_1-C_3$) alkyl, or $C_7-C_{20}$ arylalkyl;

$R_{11}$ is $C_1-C_4$ alkyl, $OR_{5'}$, fluoro, bromo, iodo, or chloro; and $R_{12'}$ is hydrogen or $C_1-C_4$ alkyl;

or a pharmaceutically acceptable salt or solvate thereof, contained within a packaging material that has a label indicating that the pharmaceutical agent can be used for treating a condition associated with dysfunctional or abnormal 5-$HT_{2B}$ receptor stimulation.

* * * * *

UNITED STATES PATENT AND TRADEMARK OFFICE
CERTIFICATE OF CORRECTION

PATENT NO. : 5,705,519

DATED : January 6, 1998

INVENTOR(S) : James E. Audia, et al.

It is certified that error appears in the above-identified patent and that said Letters Patent is hereby corrected as shown below:

Column 43, line 66 reads "...7-bromotryptamine ..." replace with -- ...5,7-difluorotryptamine... --

Signed and Sealed this

Twenty-ninth Day of May, 2001

Attest:

NICHOLAS P. GODICI

*Attesting Officer*  *Acting Director of the United States Patent and Trademark Office*